(12) United States Patent
Bewick-Sonntag et al.

(10) Patent No.: US 10,849,795 B2
(45) Date of Patent: Dec. 1, 2020

(54) TOPSHEETS INTEGRATED WITH HETEROGENOUS MASS LAYER

(71) Applicant: The Procter & Gamble Company, Cincinnati, OH (US)

(72) Inventors: Christopher Philip Bewick-Sonntag, Cincinnati, OH (US); Kelyn Anne Arora, Cincinnati, OH (US); John Lee Hammons, Hamilton, OH (US); Callida Williams Ludher, Cincinnati, OH (US); Tana Marie Kirkbride, Cincinnati, OH (US); Clint Adam Morrow, Union, KY (US); Timothy Ian Mullane, Union, KY (US); Dean Larry DuVal, Lebanon, OH (US); Stephanie Niezgoda Moss, Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 649 days.

(21) Appl. No.: 15/587,455

(22) Filed: May 5, 2017

(65) Prior Publication Data
US 2018/0110660 A1 Apr. 26, 2018

Related U.S. Application Data

(60) Provisional application No. 62/332,549, filed on May 6, 2016, provisional application No. 62/332,472, filed on May 5, 2016.

(51) Int. Cl.
*A61F 13/15* (2006.01)
*A61F 13/532* (2006.01)
(Continued)

(52) U.S. Cl.
CPC ........ *A61F 13/15* (2013.01); *A61F 13/00038* (2013.01); *A61F 13/00042* (2013.01);
(Continued)

(58) Field of Classification Search
CPC ............... A61F 13/15; A61F 13/00038; A61F 13/00042; A61F 13/00098;
(Continued)

(56) References Cited

U.S. PATENT DOCUMENTS 5,387,207 A * 2/1995 Dyer .................... A61F 5/4401
604/369
6,063,981 A * 5/2000 Wehner ............. A61F 13/51462
604/358

(Continued)

OTHER PUBLICATIONS

PCT Search Report dated Jul. 21, 2017, International Application No. PCT/US2017/031291, 14 pages.

*Primary Examiner* — Ariana Zimbouski
(74) *Attorney, Agent, or Firm* — William E. Gallagher

(57) ABSTRACT

An absorbent article and method of making the absorbent article are disclosed. The absorbent article having a topsheet, a backsheet, and an absorbent core structure having one or more layers wherein at least one layer is a heterogeneous mass layer, wherein the topsheet and the heterogeneous mass are integrated such that they reside in the same X-Y plane.

7 Claims, 39 Drawing Sheets

(51) Int. Cl.

| | |
|---|---|
| *A61F 13/534* | (2006.01) |
| *A61F 13/511* | (2006.01) |
| *A61F 13/47* | (2006.01) |
| *A61F 13/535* | (2006.01) |
| *A61F 13/537* | (2006.01) |
| *A61F 13/00* | (2006.01) |
| *B29C 43/22* | (2006.01) |
| *B29C 59/04* | (2006.01) |
| *A61F 13/53* | (2006.01) |
| *B29K 105/04* | (2006.01) |
| *B29L 31/48* | (2006.01) |

(52) U.S. Cl.
CPC .. *A61F 13/00987* (2013.01); *A61F 13/15203* (2013.01); *A61F 13/15634* (2013.01); *A61F 13/15699* (2013.01); *A61F 13/15707* (2013.01); *A61F 13/47* (2013.01); *A61F 13/51104* (2013.01); *A61F 13/532* (2013.01); *A61F 13/534* (2013.01); *A61F 13/535* (2013.01); *A61F 13/53708* (2013.01); *B29C 43/222* (2013.01); *B29C 59/046* (2013.01); *A61F 2013/15406* (2013.01); *A61F 2013/15536* (2013.01); *A61F 2013/530481* (2013.01); *A61F 2013/53721* (2013.01); *A61F 2013/530802* (2013.01); *B29K 2105/04* (2013.01); *B29K 2313/00* (2013.01); *B29L 2031/4878* (2013.01)

(58) Field of Classification Search
CPC .......... A61F 13/15203; A61F 13/15634; A61F 13/15699; A61F 13/15707; A61F 13/47; A61F 13/51104; A61F 13/532; A61F 13/534; A61F 13/535; A61F 13/53708; B29C 43/222; B29C 59/046
See application file for complete search history.

(56) References Cited

U.S. PATENT DOCUMENTS

| | | | |
|---|---|---|---|
| 2005/0266230 A1* | 12/2005 | Hill | A47L 13/16 428/317.9 |
| 2007/0142803 A1* | 6/2007 | Soerens | A61L 15/60 604/368 |
| 2007/0225669 A1* | 9/2007 | Dyer | A61F 13/2065 604/369 |
| 2008/0217809 A1* | 9/2008 | Zhao | B29C 59/046 264/229 |
| 2010/0222759 A1* | 9/2010 | Hammons | B29C 48/00 604/367 |
| 2010/0247844 A1* | 9/2010 | Curro | A61F 13/512 428/96 |
| 2013/0018341 A1* | 1/2013 | Carlucci | A61F 13/532 604/365 |
| 2014/0366293 A1* | 12/2014 | Roe | A47L 13/17 15/104.93 |
| 2015/0335498 A1 | 11/2015 | Hubbard, Jr. et al. | |
| 2017/0119598 A1 | 5/2017 | Bewick-Sonntag et al. | |

\* cited by examiner

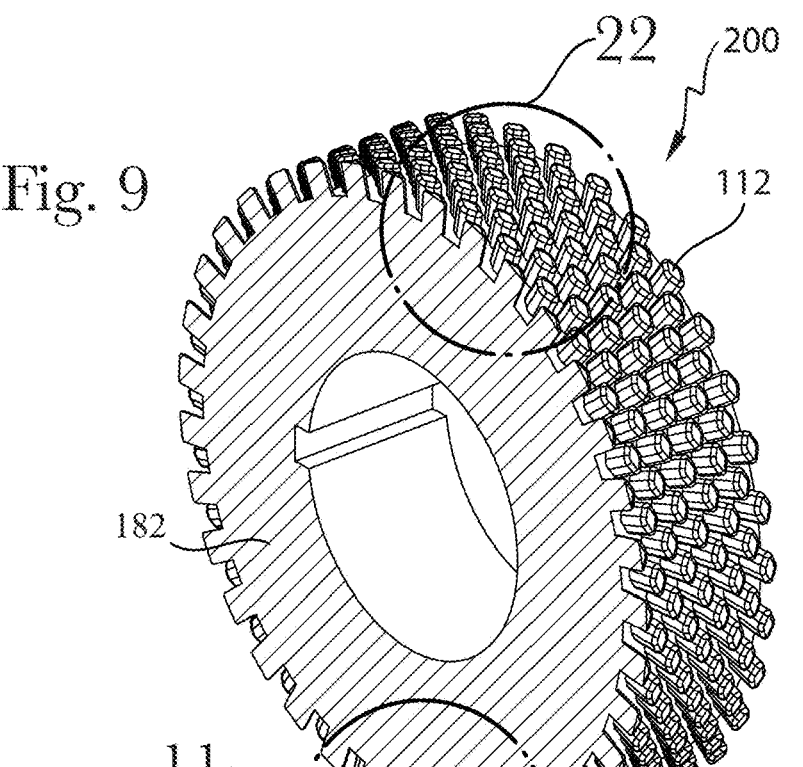
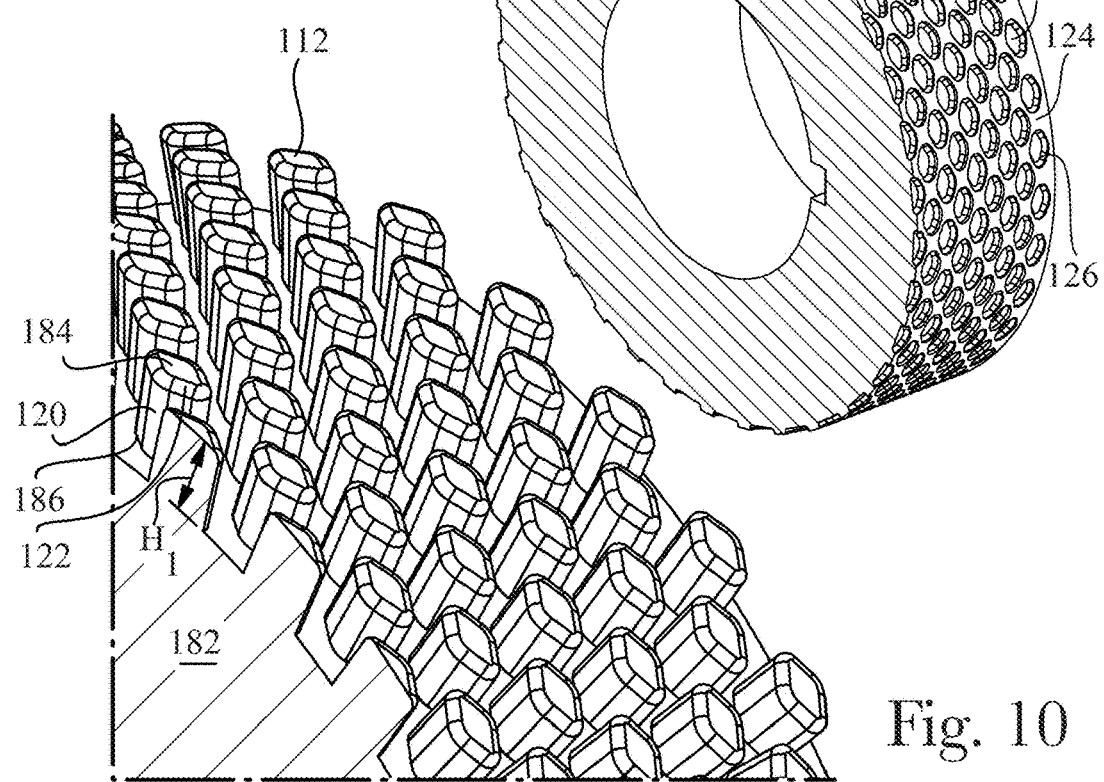
Fig. 9
Fig. 10

TOPSHEETS INTEGRATED WITH HETEROGENOUS MASS LAYER

FIELD OF THE INVENTION

The present invention relates to an absorbent structure utilizing a plurality of absorbent core layers that are integrated together in a manner that leads to beneficial physical and performance properties. The absorbent core structure is useful in absorbent articles such as diapers, incontinent briefs, training pants, diaper holders and liners, sanitary hygiene garments, and the like.

BACKGROUND OF THE INVENTION

One of the goals of an absorbent article is to absorb fluid without being noticeable to the user or others. Ideally, an article would be created that has the flexibility of a cloth undergarment while being capable of absorbing fluid rapidly into the core. However, there is often a tradeoff between comfort and rate of absorption. Further, there is often a tradeoff between the permeability of the absorbent article and the suction provided by the absorbent article. In essence, as a core becomes more permeable, it traditionally loses some of the ability to create suction within the absorbent core.

Further, there is a tradeoff made regarding flexibility and comfort inclusive of fit to body. For example, traditional cellulose based thick products focuses on high initial stiffness, recognizing that they will deform, bunch and degrade while wearing but they nevertheless offer high bulk volume in an effort to attempt to ensure sufficient body coverage is available throughout pad wear. Traditional in market products often composed of airlaid absorbent materials are thinner and more comfortable, with less initial stiffness, but are designed to better retain their shape and fit to body during wear by the use of binders such as bi-component fibers and latex to attempt to reduce structural collapse as the products are worn and loaded by the wearer.

Yet another approach for improved fit to body has been to create specific humps and valleys, so specific 3 dimensional topographies on a product to better macroscopically conform to the intimate geometries. The drawback of such approaches is such topography is 'macroscopic' in dimensions compared to the scale and complex topography present in the intimate area and at the same time, with the wide range of anatomies and body sizes, shapes the ability to deliver a preferred product geometry to the body is limited.

Another historical tradeoff that is well known is the need to provide a close to body fit in order to remove complex liquids such as menstrual fluid closer to the source and yet preserve sufficient panty coverage in case fluid is not captured at the source and the panty is exposed to fluid moving on the body or in body folds that often leads to leakage.

A variety of approaches have been leveraged to balance this competing set of mechanical requirements. On the one end typical approaches have included discrete absorbent elements contained in a tube or highly fragmented, deformable and stretchable absorbent materials able to conform to a wide variety of complex body shapes. The main limitation of such discrete or decoupled absorbent components is a fundamental inability to sustain a preferred product to body shape and, or to dynamically conform back to a preferred shape following bodily deformation. The ability to overcome the severe bunching, product bending and buckling of these discrete or decoupled approaches has not been demonstrated.

Another series of approaches to solve this complex mechanical-structural set of requirements has been to design an absorbent system with a series of preferred bending locations to force a specific bending mode in the product or to leveraging a small number of discrete core pieces or core cutouts to drive specific product shapes. The fundamental challenge that limits such approaches (including the one listed above) is three fold, first, breaking the absorbent core into pieces, however small, breaks the fluid continuity thereby limiting the ability to wick fluid and reduce saturation at the loading point. Second, women's intimate anatomy and body shapes are extremely varied and while creating specific bending or fold lines and core segments can help create a specific shape, there is no guarantee that this 'programmed shape' can fit such a wide range of intimate topography and body shapes. So its effectiveness is limited. A third limitation is that in programming specific bending or folding modes the struggle is to sustain these programmed shapes during dynamic body movements in a way that is both comfortable and resilient.

One possible material that has improved comfort are absorbent cores that utilize absorbent foams. However, because absorbent products that use foam traditionally have the foam in layers, it cannot be integrated by mechanical means with other layers because the foam will fracture and break.

Prior fibrous topsheets require a trade-off between capillarity, permeability, wetting, and rewet or fluid retention properties. If you want high permeability, you can either make the topsheet philic so that fluid passes through it fast, but then you are left with a wet topsheet with either poor rewet values or retention of fluid in the topsheet that the wearer (or care giver) can be sensitive to.

Alternatively, you can use a phobic topsheet which may give good rewet values but poor wettability or permeability. The poor wettability or permeability can partially be overcome by using apertures. However, with viscous liquids the apertures may still drain poorly due to the Bond viscosity void gap, i.e., the fluid bridges the aperture rather than draining through the aperture.

Another alternative to address skin wetness issues is a topsheet with a higher density, thus yielding higher capillarity pressures to better compete for complex and viscous liquids trapped or remaining on the body. However, unless the secondary topsheet and core layers below the topsheet have even higher capillarity, the product cannot generate enough capillary suction to properly drain the topsheet. Further, attempts to create a capillarity gradient via densification of the topsheet through embossing, channels, etc. are also problematic as the denser topsheet is stiffer to the consumer (comfort issues) and does not drain efficiently due to the disruption of a capillarity cascade, i.e. each sub layer needs to have higher capillarity that the layer above it.

As such, there exists the need to develop an absorbent structure that can, conform to a wide range of intimate topographies and overall body shapes and sizes, both statically and dynamically, that is able to follow her complex body geometry during motion and nevertheless recover to a preferred geometric shape following motion and be ready to capture fluid closer to the source in a sustained way. Further there remains the need to be able to deliver this dynamic conforming shape resiliently and comfortably all without disrupting the critical need to ensure fluid connectivity so that the primary loading area is adequately drained and suction at the primary or other loading area(s) is regenerated.

SUMMARY OF THE INVENTION

An absorbent article is disclosed. The absorbent article has a topsheet, a backsheet, and an absorbent core structure comprising one or more layers wherein at least one layer is a heterogeneous mass layer. A portion of both the topsheet and a portion of the heterogeneous mass are integrated such that they reside in an X-Y plane.

An absorbent article is disclosed. The absorbent article has a topsheet, a secondary topsheet, a backsheet, and an absorbent core structure comprising one or more layers wherein at least one layer is a heterogeneous mass layer. A portion of the topsheet, a portion of the secondary topsheet, and the heterogeneous mass are integrated such that they reside in the same X-Y plane.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

FIG. 9 is a perspective view of one example of an apparatus for forming the nonwoven material described herein.

FIG. 10 is an enlarged perspective view of a portion of the male roll shown in FIG. 9.

FIG. 10A is a schematic side view of a male element with tapered side walls.

DETAILED DESCRIPTION OF THE INVENTION

Figure 1:
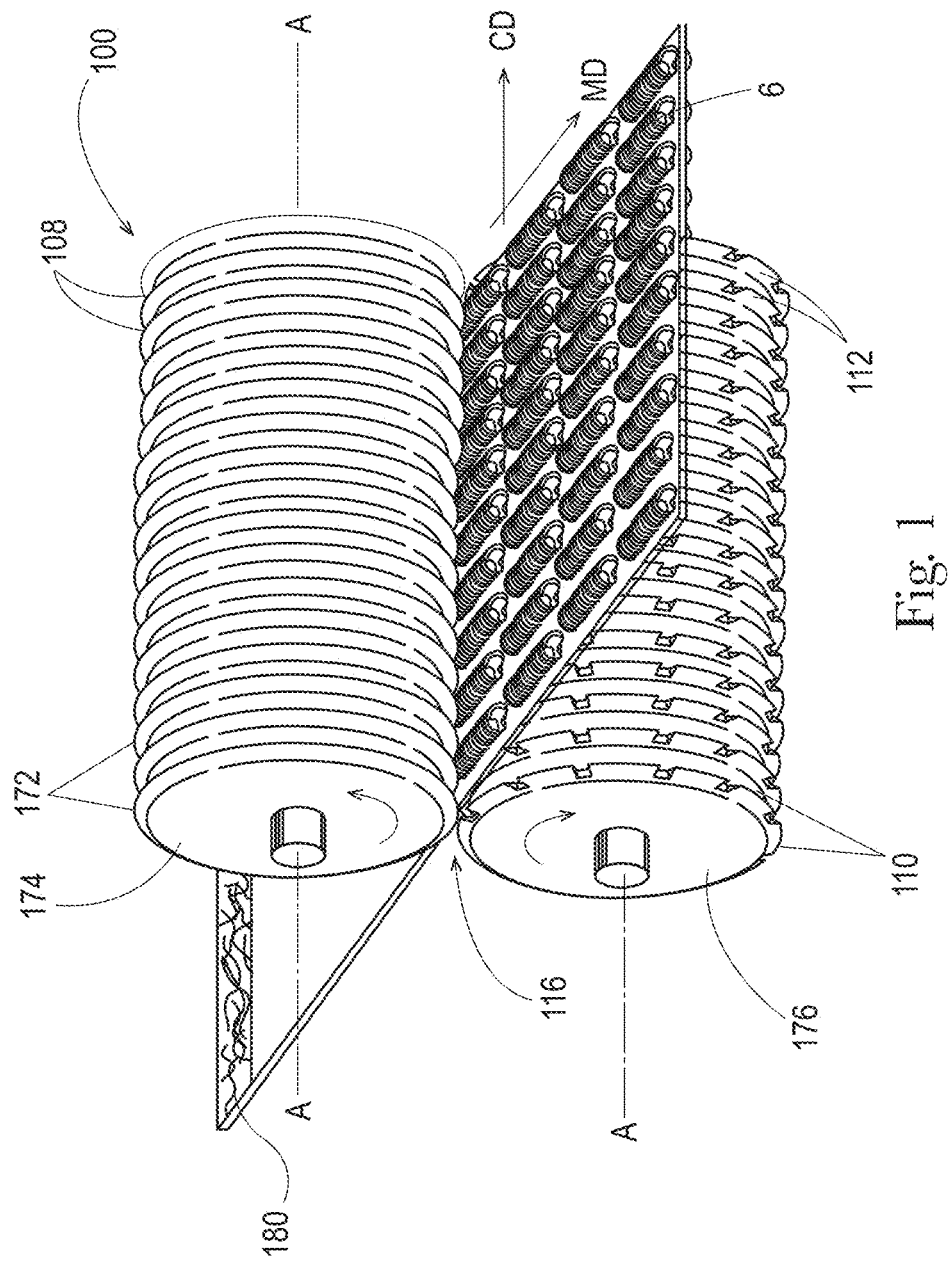
FIG. 1 is a perspective view of an apparatus for forming the web for use in the present invention.

As used herein, the term "absorbent core structure" refers to an absorbent core that is has two or more absorbent core layers. Each absorbent core layer is capable acquiring and transporting or retaining fluid.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, "complex liquids" are defined as fluids that are non-Newtonian, whose rheological properties are complex that change with shear and commonly shear thin. Such liquids commonly contain more than one phase (red blood cells plus vaginal mucous) that may phase separate on contact with topsheets and absorbent materials. In addition, complex liquids such as menstrual fluid may contain long chain proteins exhibiting stringy properties, high cohesive force within a droplet allowing for droplet elongation without breaking. Complex liquids may have solids (menstrual and runny feces).

The term "disposable" is used herein to describe articles, which are not intended to be laundered or otherwise restored or reused as an article (i.e. they are intended to be discarded after a single use and possibly to be recycled, composted or otherwise disposed of in an environmentally compatible manner). The absorbent article comprising an absorbent structure according to the present invention can be for example a sanitary napkin or a panty liner or an adult incontinence article or a baby diaper or a wound dressing. The absorbent structure of the present invention will be herein described in the context of a typical absorbent article, such as, for example, a sanitary napkin. Typically, such articles can comprise a liquid pervious topsheet, a backsheet and an absorbent core intermediate the topsheet and the backsheet.

As used herein, an "enrobeable element" refers to an element that may be enrobed by the foam. The enrobeable element may be, for example, a fiber, a group of fibers, a tuft, or a section of a film between two apertures. It is understood that other elements are contemplated by the present invention.

A "fiber" as used herein, refers to any material that can be part of a fibrous structure. Fibers can be natural or synthetic. Fibers can be absorbent or non-absorbent.

A "fibrous structure" as used herein, refers to materials which can be broken into one or more fibers. A fibrous structure can be absorbent or adsorbent. A fibrous structure can exhibit capillary action as well as porosity and permeability.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter. Thereafter, the meltblown fibers are carried by the high velocity gas stream and are deposited on a collecting surface, often while still tacky, to form a web of randomly dispersed meltblown fibers.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "non-round fibers" describes fibers having a non-round cross-section, and includes "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, spunlacing processes, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier, which is a unit of weight per length of fiber. The basis weight of laminate webs suitable for use in an article of the present invention can range from 10 gsm to 100 gsm, depending on the ultimate use of the web.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample size of at least 10 fibers) larger than 7 microns, and more particularly, between about 10 and 40 microns.

As used herein, a "strata" or "stratum" relates to one or more layers wherein the components within the stratum are intimately combined without the necessity of an adhesive, pressure bonds, heat welds, a combination of pressure and heat bonding, hydro-entangling, needlepunching, ultrasonic bonding, or similar methods of bonding known in the art such that individual components may not be wholly separated from the stratum without affecting the physical structure of the other components. The skilled artisan should understand that while separate bonding is unnecessary between the strata, bonding techniques could be employed to provide additional integrity depending on the intended use.

As used herein, a "tuft" or chad relates to discrete integral extensions of the fibers of a nonwoven web. Each tuft can comprise a plurality of looped, aligned fibers extending outwardly from the surface of the web. In another embodiment each tuft can comprise a plurality of non-looped fibers that extend outwardly from the surface of the web. In another embodiment, each tuft can comprise a plurality of fibers which are integral extensions of the fibers of two or more integrated nonwoven webs.

As used herein, a "well" or "wells" relates to one or more funnel shaped volumetric spaces wherein a portion of a fibrous layer has been integrated into a second fibrous layer without creating a higher density zone. The wells may be circular or elongated circular patterns where there is a smooth transition from a horizontal plane to a vertical plane along the surface of the well. Wells are further defined in that one or more fibers from the first fibrous layer and one or more fibers from the second fibrous layer create the outer surface of the well within the same x-y plane. The second fibrous layer is either a fluid transfer or a fluid storage layer. A well may exhibit variations in the density of the side wall or the distal end, however the density of the distal end is not greater than the average density of the original first fibrous layer. Additionally, a well may be defined as a point of discontinuity in the topsheet wherein one or more fibers of the topsheet or one or more portions of the topsheet have been changed in orientation from an X-Y plane to a Z direction plane entering an X-Y plane of the absorbent core structure.

While particular embodiments of the present invention have been illustrated and described, it would be obvious to those skilled in the art that various other changes and modifications can be made without departing from the spirit and scope of the invention.

GENERAL SUMMARY

An absorbent article structure is disclosed. The absorbent article has one of a topsheet, a secondary topsheet, or both combined with a fibrous web having a high capacity absorbent.

The fibrous web may be a heterogeneous mass comprising a fibrous web and one or more pieces of open cell foam intermixed within the fibrous web and/or enrobing one or more fibers within the fibrous web.

The fibrous web may be the upper layer of an absorbent core. The absorbent core may be a two layer system wherein the upper layer is heterogeneous mass layer comprising one or more enrobeable elements and one or more discrete open-cell foam pieces. The upper layer heterogeneous mass layer may be a stratum as defined above. The lower layer may be an absorbent layer that comprises superabsorbent polymer. The absorbent core structure may comprise additional layers below the absorbent layer that comprises superabsorbent polymer. The upper layer heterogeneous mass layer may be integrated with a topsheet using formation means.

The absorbent core structure may comprise a heterogeneous mass layer or may utilize methods or parameters such as those described in US Patent Publication No. 2015-0335498, filed May 19, 2015; US Patent Publication No. 2015-0374560, Jun. 25, 2015; US Patent Publication No. 2015-0374561 filed Jun. 26, 2015; US Patent Publication No. 2016-0346805 filed Mar. 23, 2016; US Patent Publication No. 2015-0374561 filed Jun. 25, 2015; US Patent Publication No. 2016-0287452 filed Mar. 30, 2016; US Patent Publication No. 2017-0071795 filed Nov. 4, 2016; U.S. patent application Ser. No. 15/344,273 filed Nov. 4, 2016; U.S. patent application Ser. No. 15/344,294 filed Nov. 4, 2016; US Patent Publication No. 2015-0313770 filed May 5, 2015; US Patent Publication No. 2016-0375458 filed Jun. 28, 2016; U.S. patent application Ser. No. 15/344,050 filed Nov. 4, 2016; U.S. patent application Ser. No. 15/344,117 filed Nov. 4, 2016; U.S. patent application Ser. No. 15/344,177 filed Nov. 4, 2016; U.S. patent application Ser. No. 15/344,198 filed Nov. 4, 2016; U.S. patent application Ser. No. 15/344,221 filed Nov. 4, 2016; U.S. patent application Ser. No. 15/344,239 filed Nov. 4, 2016; U.S. patent application Ser. No. 15/344,255 filed Nov. 4, 2016; U.S. patent application Ser. No. 15/464,733 filed Nov. 4, 2016; U.S. Provisional Patent Application No. 62/332,549 filed May 6, 2016; U.S. Provisional Patent Application No. 62/332,472 filed May 5, 2016; U.S. Provisional Patent Application No. 62/437,208 filed Dec. 21, 2016; U.S. Provisional Patent Application No. 62/437,225 filed Dec. 21, 2016; U.S. Provisional Patent Application No. 62/437,241 filed Dec. 21, 2016; U.S. Provisional Patent Application No. 62/437,259 filed Dec. 21, 2016, or U.S. Provisional Patent Application No. 62/500,920 filed May 3, 2017. The heterogeneous mass layer has a depth, a width, and a height.

The absorbent core structure may comprise a substrate and superabsorbent polymer layer as those described in U.S. Pat. No. 8,124,827 filed on Dec. 2, 2008 (Tamburro); U.S. application Ser. No. 12/718,244 published on Sep. 9, 2010; US application Ser. No. 12/754,935 published on Oct. 14, 2010; or U.S. Pat. No. 8,674,169 issued on Mar. 18, 2014.

The one or more discrete portions of foam pieces enrobe the enrobeable elements. The discrete portions of foam pieces are open-celled foam. In an embodiment, the foam is a High Internal Phase Emulsion (HIPE) foam. In an embodiment, one continuous piece of open cell foam may enrobe multiple enrobeable elements, such as, for example, the fibers that make up the upper layer of a nonwoven web.

In the following description of the invention, the surface of the article, or of each component thereof, which in use faces in the direction of the wearer is called wearer-facing surface. Conversely, the surface facing in use in the direction of the garment is called garment-facing surface. The absorbent article of the present invention, as well as any element thereof, such as, for example the absorbent core, has therefore a wearer-facing surface and a garment-facing surface.

The heterogeneous mass layer contains one or more discrete open-cell foam pieces foams that are integrated into the heterogeneous mass comprising one or more enrobeable elements integrated into the one or more open-cell foams such that the two may be intertwined.

The open-cell foam pieces may comprise between 1% of the heterogeneous mass by volume to 99% of the heterogeneous mass by volume, such as, for example, 5% by volume, 10% by volume, 15% by volume, 20% by volume, 25% by volume, 30% by volume, 35% by volume, 40% by volume, 45% by volume, 50% by volume, 55% by volume, 60% by volume, 65% by volume, 70% by volume, 75% by volume, 80% by volume, 85% by volume, 90% by volume, or 95% by volume.

The heterogeneous mass layer may have void space found between the enrobeable elements (e.g. fibers), between the enrobeable elements and the enrobed enrobeable elements (e.g. fibers enrobed by open cell foam), and between enrobed enrobeable elements. The void space may contain gas. The void space may represent between 1% and 95% of the total volume for a fixed amount of volume of the heterogeneous mass, such as, for example, 5%, 10%, 15%, 20%, 25%, 30%, 35%, 40%, 45%, 50%, 55%, 60%, 65%, 70%, 75%, 80%, 85%, 90% of the total volume for a fixed amount of volume of the heterogeneous mass.

The combination of open-cell foam pieces and void space within the heterogeneous mass may exhibit an absorbency of between 10 g/g to 200 g/g of the heterogeneous mass, such as for example, 40 g/g, 60 g/g, 80 g/g, 100 g/g, 120 g/g, 140 g/g 160 g/g 180 g/g or 190 g/g of the heterogeneous mass. Absorbency may be quantified according to the EDANA Nonwoven Absorption method 10.4-02.

The open-cell foam pieces are discrete foam pieces intertwined within and throughout a heterogeneous mass such that the open-cell foam enrobes one or more of the enrobeable elements such as, for example, fibers within the mass. The open-cell foam may be polymerized around the enrobeable elements.

In an embodiment, a discrete open-cell foam piece may enrobe more than one enrobeable element. The enrobeable elements may be enrobed together as a bunch. Alternatively, more than one enrobeable element may be enrobed by the discrete open-cell foam piece without contacting another enrobeable element.

In an embodiment, the open-cell foam pieces may enrobe an enrobeable element such that the enrobeable element is enrobed along the enrobeable elements axis for between 5% and 95% of the length along the enrobeable element's axis. For example, a single fiber may be enrobed along the length of the fiber for a distance greater than 50% of the entire length of the fiber. In an embodiment, an enrobeable element may have between 5% and 100% of its surface area enrobed by one or more open-cell foam pieces.

In an embodiment, two or more open-cell foam pieces may enrobe the same enrobeable element such that the enrobeable element is enrobed along the enrobeable elements axis for between 5% and 100% of the length along the enrobeable element's axis.

The open-cell foam pieces enrobe the enrobeable elements such that a layer surrounds the enrobeable element at a given cross section. The layer surrounding the enrobeable element at a given cross section may be between 0.01 mm to 100 mm such as, for example, 0.1 mm, 0.2 mm, 0.3 mm, 0.4 mm, 0.5 mm, 0.6 mm, 0.7 mm, 0.8 mm, 0.9 mm, 1.0 mm, 1.2 mm, 1.4 mm, 1.6 mm, 1.8 mm, 2.0 mm, 2.2 mm, 2.4 mm, 2.6 mm, 2.8 mm, or 3 mm. The layer may not be equivalent in dimension at all points along the cross section of the enrobeable element. For example, in an embodiment, an enrobeable element may be enrobed by 0.5 mm at one point along the cross section and by 1.0 mm at a different point along the same cross section.

The open-cell foam pieces are considered discrete in that they are not continuous throughout the entire heterogeneous mass layer. Not continuous throughout the entire heterogeneous mass layer represents that at any given point in the heterogeneous mass layer, the open-cell absorbent foam is not continuous in at least one of the cross sections of a longitudinal, a vertical, and a lateral plane of the heterogeneous mass layer. In a non-limiting embodiment, the absorbent foam is not continuous in the lateral and the vertical planes of the cross section for a given point in the heterogeneous mass layer. In a non-limiting embodiment, the absorbent foam is not continuous in the longitudinal and the vertical planes of the cross section for a given point in the heterogeneous mass layer. In a non-limiting embodiment, the absorbent foam is not continuous in the longitudinal and the lateral planes of the cross section for a given point in the heterogeneous mass layer.

In an embodiment wherein the open-cell foam is not continuous in at least one of the cross sections of the longitudinal, the vertical, and the lateral plane of the heterogeneous mass, one or both of either the enrobeable elements or the open-cell foam pieces may be bi-continuous throughout the heterogeneous mass.

The open-cell foam pieces may be located at any point in the heterogeneous mass. In a non-limiting embodiment, a foam piece may be surrounded by the elements that make up the enrobeable elements. In a non-limiting embodiment a foam piece may be located on the outer perimeter of the heterogeneous mass such that only a portion of the foam piece is entangled with the elements of the heterogeneous mass.

In a non-limiting embodiment, the open-cell foam pieces may expand upon being contacted by a fluid to form a channel of discrete open-cell foam pieces. The open-cell foam pieces may or may not be in contact prior to being expanded by a fluid.

An open-celled foam may be integrated onto the enrobeable elements prior to being polymerized. In a non-limiting embodiment the open-cell foam pieces may be partially polymerized prior to being impregnated into or onto the enrobeable elements such that they become intertwined. After being impregnated into or onto the enrobeable elements, the open-celled foam in either a liquid or solid state are polymerized to form one or more open-cell foam pieces.

The open cell foam pieces may be impregnated prior to polymerization into or onto two or more different enrobeable elements that are combined to create a heterogeneous mixture of enrobeable elements. The two or more different enrobeable elements may be intertwined such that one enrobeable element may be surrounded by multiples of the second enrobeable element, such as, for example by using more than one type of fiber in a mixture of fibers or by coating one or more fibers with surfactant. The two or more different enrobeable elements may be layered within the heterogeneous mass along any of the vertical, longitudinal, and/or lateral planes such that the enrobeable elements are profiled within the heterogeneous mass for an enrobeable element inherent property or physical property, such as, for example, hydrophobicity, fiber diameter, fiber or composition. It is understood that any inherent property or physical property of the enrobeable elements listed is contemplated herein.

The open-celled foam may be polymerized using any known method including, for example, heat, UV, and infrared. Following the polymerization of a water in oil open-cell foam emulsion, the resulting open-cell foam is saturated with aqueous phase that needs to be removed to obtain a substantially dry open-cell foam. Removal of the saturated aqueous phase or dewatering may occur using nip rollers, and vacuum. Utilizing a nip roller may also reduce the thickness of the heterogeneous mass such that the heterogeneous mass will remain thin until the open-cell foam pieces entwined in the heterogeneous mass are exposed to fluid.

Dependent upon the desired foam density, polymer composition, specific surface area, or pore size (also referred to as cell size), the open-celled foam may be made with different chemical composition, physical properties, or both. For instance, dependent upon the chemical composition, an open-celled foam may have a density of 0.0010 g/cc to about 0.25 g/cc. Preferred 0.04 g/cc.

Open-cell foam pore sizes may range in average diameter of from 1 to 800 such as, for example, between 50 and 700 between 100 and 600 between 200 and 500 between 300 and 400 μm.

In some embodiments, the foam pieces have a relatively uniform cell size. For example, the average cell size on one major surface may be about the same or vary by no greater than 10% as compared to the opposing major surface. In other embodiments, the average cell size of one major surface of the foam may differ from the opposing surface. For example, in the foaming of a thermosetting material it is not uncommon for a portion of the cells at the bottom of the cell structure to collapse resulting in a lower average cell size on one surface.

The foams produced from the present invention are relatively open-celled. This refers to the individual cells or pores of the foam being in substantially unobstructed communication with adjoining cells. The cells in such substantially open-celled foam structures have intercellular openings or windows that are large enough to permit ready fluid transfer from one cell to another within the foam structure. For purpose of the present invention, a foam is considered "open-celled" if at least about 80% of the cells in the foam that are at least 1 µm in average diameter size are in fluid communication with at least one adjoining cell.

In addition to being open-celled, in certain embodiments foams are sufficiently hydrophilic to permit the foam to absorb aqueous fluids, for example the internal surfaces of a foam may be rendered hydrophilic by residual hydrophilizing surfactants or salts left in the foam following polymerization, by selected post-polymerization foam treatment procedures (as described hereafter), or combinations of both.

In certain embodiments, for example when used in certain absorbent articles, an open-cell foam may be flexible and exhibit an appropriate glass transition temperature (Tg). The Tg represents the midpoint of the transition between the glassy and rubbery states of the polymer.

In certain embodiments, the Tg of this region will be less than about 200° C. for foams used at about ambient temperature conditions, in certain other embodiments less than about 90° C. The Tg may be less than 50° C.

The open-cell foam pieces may be distributed in any suitable manner throughout the heterogeneous mass. In an embodiment, the open-cell foam pieces may be profiled along the vertical axis such that smaller pieces are located above larger pieces. Alternatively, the pieces may be profiled such that smaller pieces are below larger pieces. In another embodiment, the open-cell pieces may be profiled along a vertical axis such that they alternate in size along the axis.

In an embodiment the open-cell foam pieces may be profiled along any one of the longitudinal, lateral, or vertical axis based on one or more characteristics of the open-cell foam pieces. Characteristics by which the open-cell foam pieces may be profiled within the heterogeneous mass may include, for example, absorbency, density, cell size, and combinations thereof.

In an embodiment, the open-cell foam pieces may be profiled along any one of the longitudinal, lateral, or vertical axis based on the composition of the open-cell foam. The open-cell foam pieces may have one composition exhibiting desirable characteristics in the front of the heterogeneous mass and a different composition in the back of the heterogeneous mass designed to exhibit different characteristics. The profiling of the open-cell foam pieces may be either symmetric or asymmetric about any of the prior mentioned axes or orientations.

The open-cell foam pieces may be distributed along the longitudinal and lateral axis of the heterogeneous mass in any suitable form. In an embodiment, the open-cell foam pieces may be distributed in a manner that forms a design or shape when viewed from a top planar view. The open-cell foam pieces may be distributed in a manner that forms stripes, ellipticals, squares, or any other known shape or pattern.

In an embodiment, different types of foams may be used in one heterogeneous mass. For example, some of the foam pieces may be polymerized HIPE while other pieces may be made from polyurethane. The pieces may be located at specific locations within the mass based on their properties to optimize the performance of the heterogeneous mass.

In an embodiment, the open-celled foam is a thermoset polymeric foam made from the polymerization of a High Internal Phase Emulsion (HIPE), also referred to as a polyHIPE. To form a HIPE, an aqueous phase and an oil phase are combined in a ratio between about 8:1 and 140:1. In certain embodiments, the aqueous phase to oil phase ratio is between about 10:1 and about 75:1, and in certain other embodiments the aqueous phase to oil phase ratio is between about 13:1 and about 65:1. This is termed the "water-to-oil" or W:O ratio and can be used to determine the density of the resulting polyHIPE foam. As discussed, the oil phase may contain one or more of monomers, co-monomers, photo-initiators, cross-linkers, and emulsifiers, as well as optional components. The water phase will contain water and in certain embodiments one or more components such as electrolyte, initiator, or optional components.

The open-cell foam can be formed from the combined aqueous and oil phases by subjecting these combined phases to shear agitation in a mixing chamber or mixing zone. The combined aqueous and oil phases are subjected to shear agitation to produce a stable HIPE having aqueous droplets of the desired size. An initiator may be present in the aqueous phase, or an initiator may be introduced during the foam making process, and in certain embodiments, after the HIPE has been formed. The emulsion making process produces a HIPE where the aqueous phase droplets are dispersed to such an extent that the resulting HIPE foam will have the desired structural characteristics. Emulsification of the aqueous and oil phase combination in the mixing zone may involve the use of a mixing or agitation device such as an impeller, by passing the combined aqueous and oil phases through a series of static mixers at a rate necessary to impart the requisite shear, or combinations of both. Once formed, the HIPE can then be withdrawn or pumped from the mixing zone. One method for forming HIPEs using a continuous process is described in U.S. Pat. No. 5,149,720 (DesMarais et al), issued Sep. 22, 1992; U.S. Pat. No. 5,827,909 (Des-Marais) issued Oct. 27, 1998; and U.S. Pat. No. 6,369,121 (Catalfamo et al.) issued Apr. 9, 2002.

The emulsion can be withdrawn or pumped from the mixing zone and impregnated into or onto a mass prior to being fully polymerized. Once fully polymerized, the foam pieces and the elements are intertwined such that discrete foam pieces are bisected by the elements comprising the mass and such that parts of discrete foam pieces enrobe portions of one or more of the elements comprising the heterogeneous mass.

Following polymerization, the resulting foam pieces are saturated with aqueous phase that needs to be removed to obtain substantially dry foam pieces. In certain embodiments, foam pieces can be squeezed free of most of the aqueous phase by using compression, for example by running the heterogeneous mass comprising the foam pieces through one or more pairs of nip rollers. The nip rollers can be positioned such that they squeeze the aqueous phase out of the foam pieces. The nip rollers can be porous and have a vacuum applied from the inside such that they assist in drawing aqueous phase out of the foam pieces. In certain embodiments, nip rollers can be positioned in pairs, such that a first nip roller is located above a liquid permeable belt, such as a belt having pores or composed of a mesh-like material and a second opposing nip roller facing the first nip roller and located below the liquid permeable belt. One of the pair, for example the first nip roller can be pressurized while the other, for example the second nip roller, can be evacuated, so as to both blow and draw the aqueous phase out the of the foam. The nip rollers may also be heated to assist in removing the aqueous phase. In certain embodiments, nip rollers are only applied to non-rigid foams, that is, foams whose walls would not be destroyed by compressing the foam pieces.

In certain embodiments, in place of or in combination with nip rollers, the aqueous phase may be removed by sending the foam pieces through a drying zone where it is heated, exposed to a vacuum, or a combination of heat and vacuum exposure. Heat can be applied, for example, by running the foam though a forced air oven, IR oven, microwave oven or radiowave oven. The extent to which a foam is dried depends on the application. In certain embodiments, greater than 50% of the aqueous phase is removed. In certain other embodiments greater than 90%, and in still other embodiments greater than 95% of the aqueous phase is removed during the drying process.

In an embodiment, open-cell foam is produced from the polymerization of the monomers having a continuous oil phase of a High Internal Phase Emulsion (HIPE). The HIPE may have two phases. One phase is a continuous oil phase having monomers that are polymerized to form a HIPE foam and an emulsifier to help stabilize the HIPE. The oil phase may also include one or more photo-initiators. The monomer component may be present in an amount of from about 80% to about 99%, and in certain embodiments from about 85% to about 95% by weight of the oil phase. The emulsifier component, which is soluble in the oil phase and suitable for forming a stable water-in-oil emulsion may be present in the oil phase in an amount of from about 1% to about 20% by weight of the oil phase. The emulsion may be formed at an emulsification temperature of from about 10° C. to about 130° C. and in certain embodiments from about 50° C. to about 100° C.

In general, the monomers will include from about 20% to about 97% by weight of the oil phase at least one substantially water-insoluble monofunctional alkyl acrylate or alkyl methacrylate. For example, monomers of this type may include $C_4$-$C_{18}$ alkyl acrylates and $C_2$-$C_{18}$ methacrylates, such as ethylhexyl acrylate, butyl acrylate, hexyl acrylate, octyl acrylate, nonyl acrylate, decyl acrylate, isodecyl acrylate, tetradecyl acrylate, benzyl acrylate, nonyl phenyl acrylate, hexyl methacrylate, 2-ethylhexyl methacrylate, octyl methacrylate, nonyl methacrylate, decyl methacrylate, isodecyl methacrylate, dodecyl methacrylate, tetradecyl methacrylate, and octadecyl methacrylate.

The oil phase may also have from about 2% to about 40%, and in certain embodiments from about 10% to about 30%, by weight of the oil phase, a substantially water-insoluble, polyfunctional crosslinking alkyl acrylate or methacrylate. This crosslinking co-monomer, or cross-linker, is added to confer strength and resilience to the resulting HIPE foam. Examples of crosslinking monomers of this type may have monomers containing two or more activated acrylate, methacrylate groups, or combinations thereof. Nonlimiting examples of this group include 1,6-hexanedioldiacrylate, 1,4-butanedioldimethacrylate, trimethylolpropane triacrylate, trimethylolpropane trimethacrylate, 1,12-dodecyldimethacrylate, 1,14-tetradecanedioldimethacrylate, ethylene glycol dimethacrylate, neopentyl glycol diacrylate (2,2-dimethylpropanediol diacrylate), hexanediol acrylate methacrylate, glucose pentaacrylate, sorbitan pentaacrylate, and the like. Other examples of cross-linkers contain a mixture of acrylate and methacrylate moieties, such as ethylene glycol acrylate-methacrylate and neopentyl glycol acrylate-methacrylate. The ratio of methacrylate:acrylate group in the mixed cross-linker may be varied from 50:50 to any other ratio as needed.

Any third substantially water-insoluble co-monomer may be added to the oil phase in weight percentages of from about 0% to about 15% by weight of the oil phase, in certain embodiments from about 2% to about 8%, to modify properties of the HIPE foams. In certain embodiments, "toughening" monomers may be desired which impart toughness to the resulting HIPE foam. These include monomers such as styrene, vinyl chloride, vinylidene chloride, isoprene, and chloroprene. Without being bound by theory, it is believed that such monomers aid in stabilizing the HIPE during polymerization (also known as "curing") to provide a more homogeneous and better formed HIPE foam which results in better toughness, tensile strength, abrasion resistance, and the like. Monomers may also be added to confer flame retardancy as disclosed in U.S. Pat. No. 6,160,028 (Dyer) issued Dec. 12, 2000. Monomers may be added to confer color, for example vinyl ferrocene, fluorescent properties, radiation resistance, opacity to radiation, for example lead tetraacrylate, to disperse charge, to reflect incident infrared light, to absorb radio waves, to form a wettable surface on the HIPE foam struts, or for any other desired property in a HIPE foam. In some cases, these additional monomers may slow the overall process of conversion of HIPE to HIPE foam, the tradeoff being necessary if the desired property is to be conferred. Thus, such monomers can be used to slow down the polymerization rate of a HIPE. Examples of monomers of this type can have styrene and vinyl chloride.

The oil phase may further contain an emulsifier used for stabilizing the HIPE. Emulsifiers used in a HIPE can include: (a) sorbitan monoesters of branched $C_{16}$-$C_{24}$ fatty acids; linear unsaturated $C_{16}$-$C_{22}$ fatty acids; and linear saturated $C_{12}$-$C_{14}$ fatty acids, such as sorbitan monooleate, sorbitan monomyristate, and sorbitan monoesters, sorbitan monolaurate diglycerol monooleate (DGMO), polyglycerol monoisostearate (PGMIS), and polyglycerol monomyristate (PGMM); (b) polyglycerol monoesters of -branched $C_{16}$-$C_{24}$ fatty acids, linear unsaturated $C_{16}$-$C_{22}$ fatty acids, or linear saturated $C_{12}$-$C_{14}$ fatty acids, such as diglycerol monooleate (for example diglycerol monoesters of C18:1 fatty acids), diglycerol monomyristate, diglycerol monoisostearate, and diglycerol monoesters; (c) diglycerol monoaliphatic ethers of -branched $C_{16}$-$C_{24}$ alcohols, linear unsaturated $C_{16}$-$C_{22}$ alcohols, and linear saturated $C_{12}$-$C_{14}$ alcohols, and mixtures of these emulsifiers. See U.S. Pat. No. 5,287,207 (Dyer et al.), issued Feb. 7, 1995 and U.S. Pat. No. 5,500,451 (Goldman et al.) issued Mar. 19, 1996. Another emulsifier that may be used is polyglycerol succinate (PGS), which is formed from an alkyl succinate, glycerol, and triglycerol.

Such emulsifiers, and combinations thereof, may be added to the oil phase so that they can have between about 1% and about 20%, in certain embodiments from about 2% to about 15%, and in certain other embodiments from about 3% to about 12% by weight of the oil phase. In certain embodiments, co-emulsifiers may also be used to provide additional control of cell size, cell size distribution, and emulsion stability, particularly at higher temperatures, for example greater than about 65° C. Examples of co-emulsifiers include phosphatidyl cholines and phosphatidyl choline-containing compositions, aliphatic betaines, long chain $C_{12}$-$C_{22}$ dialiphatic quaternary ammonium salts, short chain $C_1$-$C_4$ dialiphatic quaternary ammonium salts, long chain $C_{12}$-$C_{22}$ dialkoyl(alkenoyl)-2-hydroxyethyl, short chain $C_1$-$C_4$ dialiphatic quaternary ammonium salts, long chain $C_{12}$-$C_{22}$ dialiphatic imidazolinium quaternary ammonium salts, short chain $C_1$-$C_4$ dialiphatic imidazolinium quaternary ammonium salts, long chain $C_{12}$-$C_{22}$ monoaliphatic benzyl quaternary ammonium salts, long chain $C_{12}$-$C_{22}$ dialkoyl(alkenoyl)-2-aminoethyl, short chain $C_1$-$C_4$ monoaliphatic benzyl quaternary ammonium salts, short chain $C_1$-$C_4$ monohydroxyaliphatic quaternary ammonium salts.

In certain embodiments, ditallow dimethyl ammonium methyl sulfate (DTDMAMS) may be used as a co-emulsifier.

The oil phase may comprise a photo-initiator at between about 0.05% and about 10%, and in certain embodiments between about 0.2% and about 10% by weight of the oil phase. Lower amounts of photo-initiator allow light to better penetrate the HIPE foam, which can provide for polymerization deeper into the HIPE foam. However, if polymerization is done in an oxygen-containing environment, there should be enough photo-initiator to initiate the polymerization and overcome oxygen inhibition. Photo-initiators can respond rapidly and efficiently to a light source with the production of radicals, cations, and other species that are capable of initiating a polymerization reaction. The photo-initiators used in the present invention may absorb UV light at wavelengths of about 200 nanometers (nm) to about 800 nm, in certain embodiments about 200 nm to about 350 nm. If the photo-initiator is in the oil phase, suitable types of oil-soluble photo-initiators include benzyl ketals, α-hydroxyalkyl phenones, α-amino alkyl phenones, and acylphospine oxides. Examples of photo-initiators include 2,4,6-[trimethylbenzoyldiphosphine]oxide in combination with 2-hydroxy-2-methyl-1-phenylpropan-1-one (50:50 blend of the two is sold by Ciba Speciality Chemicals, Ludwigshafen, Germany as DAROCUR® 4265); benzyl dimethyl ketal (sold by Ciba Geigy as IRGACURE 651); α-,α-dimethoxy-α-hydroxy acetophenone (sold by Ciba Speciality Chemicals as DAROCUR® 1173); 2-methyl-1-[4-(methylthio)phenyl]-2-morpholino-propan-1-one (sold by Ciba Speciality Chemicals as IRGACURE® 907); 1-hydroxycyclohexyl-phenyl ketone (sold by Ciba Speciality Chemicals as IRGACURE® 184); bis(2,4,6-trimethylbenzoyl)-phenylphosphineoxide (sold by Ciba Speciality Chemicals as IRGACURE 819); diethoxyacetophenone, and 4-(2-hydroxyethoxy)phenyl-(2-hydroxy-2-methylpropyl) ketone (sold by Ciba Speciality Chemicals as IRGACURE® 2959); and Oligo [2-hydroxy-2-methyl-1-[4-(1-methylvinyl)phenyl]propanone] (sold by Lambeth spa, Gallarate, Italy as ESACURE® KIP EM.

The dispersed aqueous phase of a HIPE can have water, and may also have one or more components, such as initiator, photo-initiator, or electrolyte, wherein in certain embodiments, the one or more components are at least partially water soluble.

One component of the aqueous phase may be a water-soluble electrolyte. The water phase may contain from about 0.2% to about 40%, in certain embodiments from about 2% to about 20%, by weight of the aqueous phase of a water-soluble electrolyte. The electrolyte minimizes the tendency of monomers, co-monomers, and cross-linkers that are primarily oil soluble to also dissolve in the aqueous phase. Examples of electrolytes include chlorides or sulfates of alkaline earth metals such as calcium or magnesium and chlorides or sulfates of alkali earth metals such as sodium. Such electrolyte can include a buffering agent for the control of pH during the polymerization, including such inorganic counter-ions as phosphate, borate, and carbonate, and mixtures thereof. Water soluble monomers may also be used in the aqueous phase, examples being acrylic acid and vinyl acetate.

Another component that may be present in the aqueous phase is a water-soluble free-radical initiator. The initiator can be present at up to about 20 mole percent based on the total moles of polymerizable monomers present in the oil phase. In certain embodiments, the initiator is present in an amount of from about 0.001 to about 10 mole percent based on the total moles of polymerizable monomers in the oil phase. Suitable initiators include ammonium persulfate, sodium persulfate, potassium persulfate, 2,2'-azobis(N,N'-dimethyleneisobutyramidine) dihydrochloride, and other suitable azo initiators. In certain embodiments, to reduce the potential for premature polymerization which may clog the emulsification system, addition of the initiator to the monomer phase may be just after or near the end of emulsification.

Photo-initiators present in the aqueous phase may be at least partially water soluble and can have between about 0.05% and about 10%, and in certain embodiments between about 0.2% and about 10% by weight of the aqueous phase. Lower amounts of photo-initiator allow light to better penetrate the HIPE foam, which can provide for polymerization deeper into the HIPE foam. However, if polymerization is done in an oxygen-containing environment, there should be enough photo-initiator to initiate the polymerization and overcome oxygen inhibition. Photo-initiators can respond rapidly and efficiently to a light source with the production of radicals, cations, and other species that are capable of initiating a polymerization reaction. The photo-initiators used in the present invention may absorb UV light at wavelengths of from about 200 nanometers (nm) to about 800 nm, in certain embodiments from about 200 nm to about 350 nm, and in certain embodiments from about 350 nm to about 450 nm. If the photo-initiator is in the aqueous phase, suitable types of water-soluble photo-initiators include benzophenones, benzils, and thioxanthones. Examples of photo-initiators include 2,2'-Azobis[2-(2-imidazolin-2-yl)propane] dihydrochloride; 2,2'-Azobis[2-(2-imidazolin-2-yl)propane] disulfate dehydrate; 2,2'-Azobis(1-imino-1-pyrrolidino-2-ethylpropane) dihydrochloride; 2,2'-Azobis[2-methyl-N-(2-hydroxyethyl)propionamide]; 2,2'-Azobis(2-methylpropionamidine) dihydrochloride; 2,2'-dicarboxymethoxydibenzalacetone, 4,4'-dicarboxymethoxydibenzalacetone, 4,4'-dicarboxymethoxydibenzalcyclohexanone,4-dimethylamino-4'-carboxymethoxydibenzalacetone; and 4,4'-disulphoxymethoxydibenzalacetone. Other suitable photo-initiators that can be used in the present invention are listed in U.S. Pat. No. 4,824,765 (Sperry et al.) issued Apr. 25, 1989.

In addition to the previously described components other components may be included in either the aqueous or oil phase of a HIPE. Examples include antioxidants, for example hindered phenolics, hindered amine light stabilizers; plasticizers, for example dioctyl phthalate, dinonyl sebacate; flame retardants, for example halogenated hydrocarbons, phosphates, borates, inorganic salts such as antimony trioxide or ammonium phosphate or magnesium hydroxide; dyes and pigments; fluorescers; filler pieces, for example starch, titanium dioxide, carbon black, or calcium carbonate; fibers; chain transfer agents; odor absorbers, for example activated carbon particulates; dissolved polymers; dissolved oligomers; and the like.

The heterogeneous mass comprises enrobeable elements and discrete pieces of foam. The enrobeable elements may be a web or a portion of a web such as, for example, nonwoven, a fibrous structure, an air-laid web, a wet laid web, a high loft nonwoven, a needlepunched web, a hydroentangled web, a fiber tow, a woven web, a knitted web, a flocked web, a spunbond web, a layered spunbond/melt blown web, a carded fiber web, a coform web of cellulose fiber and melt blown fibers, a coform web of staple fibers and melt blown fibers, and layered webs that are layered combinations thereof.

The enrobeable elements may be, for example, conventional absorbent materials such as creped cellulose wadding, fluffed cellulose fibers, wood pulp fibers also known as airfelt, and textile fibers. The enrobeable elements may also be fibers such as, for example, synthetic fibers, thermoplastic particulates or fibers, tricomponent fibers, and bicomponent fibers such as, for example, sheath/core fibers having the following polymer combinations: polyethylene/polypropylene, polyethylvinyl acetate/polypropylene, polyethylene/polyester, polypropylene/polyester, copolyester/polyester, and the like. The enrobeable elements may be any combination of the materials listed above and/or a plurality of the materials listed above, alone or in combination.

The enrobeable elements may be hydrophobic or hydrophilic. In an embodiment, the enrobeable elements may be treated to be made hydrophobic. In an embodiment, the enrobeable elements may be treated to become hydrophilic.

The constituent fibers of the heterogeneous mass can be comprised of polymers such as polyethylene, polypropylene, polyester, and blends thereof. The fibers can be spunbond fibers. The fibers can be meltblown fibers. The fibers can comprise cellulose, rayon, cotton, or other natural materials or blends of polymer and natural materials. The fibers can also comprise a super absorbent material such as polyacrylate or any combination of suitable materials. The fibers can be monocomponent, bicomponent, and/or biconstituent, non-round (e.g., capillary channel fibers), and can have major cross-sectional dimensions (e.g., diameter for round fibers) ranging from 0.1-500 microns. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers can range from about 0.1 denier to about 100 denier.

The heterogeneous mass can be comprised of more than one nonwoven precursor web. For example, the high internal phase emulsion is applied to the top surface of the first nonwoven web by means of an extrusion die in a horizontal configuration. A second nonwoven web can be applied to the top surface of the previously extruded high internal phase emulsion while in a horizontal configuration prior to the onset of solidification of the HIPE into a HIPE foam.

The above described structure creates a two nonwoven structure with HIPE foam in between the nonwovens and enrobed elements at the interface of HIPE foam and nonwoven, e.g. an absorbent stratum that is a heterogeneous mass comprising a first nonwoven having a first surface and a second surface and a second nonwoven. An open cell foam piece enrobes a portion of the first nonwoven and a portion of the second nonwoven. Alternatively, the second precursor web may be glued to the stratum heterogeneous mass after polymerization of the stratum.

It has been surprisingly found that by creating a heterogenous mass layer comprising open cell foam wherein at least a portion of one or more open cell foam pieces is in contact with a substrate or layer of enrobeable elements such as nonwoven fibers at both the top and bottom surface of the piece along a vertical axis allows for the heterogeneous mass to be submitted through a formation means while maintaining the fluid connectivity of the heterogeneous mass layer and without leaving a meaningful buildup or residue on the formation means.

In one aspect, known absorbent web materials in an as-made state can be considered as being homogeneous throughout. Being homogeneous, the fluid handling properties of the absorbent web material are not location dependent, but are substantially uniform at any area of the web. Homogeneity can be characterized by density, basis weight, for example, such that the density or basis weight of any particular part of the web is substantially the same as an average density or basis weight for the web. By the apparatus and method of the present invention, homogeneous fibrous absorbent web materials are modified such that they are no longer homogeneous, but are heterogeneous, such that the fluid handling and or mechanical properties of the web material are location dependent. Therefore, for the heterogeneous absorbent materials of the present invention, at discrete locations the density or basis weight of the web may be substantially different than the average density or basis weight for the web. The heterogeneous nature of the absorbent web of the present invention permits the negative aspects of either of permeability or capillarity to be minimized by rendering discrete portions highly permeable and other discrete portions to have high capillarity. Likewise, the tradeoff between permeability and capillarity is managed such that delivering relatively higher permeability can be accomplished without a decrease in capillarity. Likewise the heterogeneous nature of the absorbent web may also enable discrete bending, compression or stretch zones within the web.

In an embodiment, the heterogeneous mass may also include superabsorbent material that imbibe fluids and form hydrogels. These materials are typically capable of absorbing large quantities of body fluids and retaining them under moderate pressures and can be in either a fibrous, particulate or other physical form. The heterogeneous mass can include such materials dispersed in a suitable carrier such as cellulose fibers in the form of fluff or stiffened fibers or integrated within an AGM containing laminate.

The heterogeneous mass may include one or more types of fibers. Fibers included in the fibrous web may be thermoplastic particulates or fibers. The materials, and in particular thermoplastic fibers, can be made from a variety of thermoplastic polymers including polyolefins such as polyethylene (e.g., PULPEX®) and polypropylene, polyesters, copolyesters, and copolymers of any of the foregoing.

Depending upon the desired characteristics, suitable thermoplastic materials include hydrophobic fibers that have been made hydrophilic, such as surfactant-treated or silica-treated thermoplastic fibers derived from, for example, polyolefins such as polyethylene or polypropylene, polyacrylics, polyamides, polystyrenes, and the like. The surface of the hydrophobic thermoplastic fiber can be rendered hydrophilic by treatment with a surfactant, such as a nonionic or anionic surfactant, e.g., by spraying the fiber with a surfactant, by dipping the fiber into a surfactant or by including the surfactant as part of the polymer melt in producing the thermoplastic fiber. Upon melting and resolidification, the surfactant will tend to remain at the surfaces of the thermoplastic fiber. Suitable surfactants include nonionic surfactants such as Brij 76 manufactured by ICI Americas, Inc. of Wilmington, Del., and various surfactants sold under the Pegosperse® trademark by Glyco Chemical, Inc. of Greenwich, Conn. Besides nonionic surfactants, anionic surfactants can also be used. These surfactants can be applied to the thermoplastic fibers at levels of, for example, from about 0.2 to about 1 g. per sq. of centimeter of thermoplastic fiber.

Suitable thermoplastic fibers can be made from a single polymer (monocomponent fibers), or can be made from more than one polymer (e.g., bicomponent fibers). The polymer comprising the sheath often melts at a different, typically lower, temperature than the polymer comprising the core. As a result, these bicomponent fibers provide thermal bonding due to melting of the sheath polymer, while retaining the desirable strength characteristics of the core polymer.

Suitable bicomponent fibers for use in the present invention can include sheath/core fibers having the following polymer combinations: polyethylene/polypropylene, polyethylvinyl acetate/polypropylene, polyethylene/polyester, polypropylene/polyester, copolyester/polyester, and the like. Particularly suitable bicomponent thermoplastic fibers for use herein are those having a polypropylene or polyester core, and a lower melting copolyester, polyethylvinyl acetate or polyethylene sheath (e.g., DANAKLON®, CELBOND® or CHISSO® bicomponent fibers). These bicomponent fibers can be concentric or eccentric. As used herein, the terms "concentric" and "eccentric" refer to whether the sheath has a thickness that is even, or uneven, through the cross-sectional area of the bicomponent fiber. Eccentric bicomponent fibers can be desirable in providing more compressive strength at lower fiber thicknesses. Suitable bicomponent fibers for use herein can be either uncrimped (i.e. unbent) or crimped (i.e. bent). Bicomponent fibers can be crimped by typical textile means such as, for example, a stuffer box method or the gear crimp method to achieve a predominantly two-dimensional or "flat" crimp.

The length of bicomponent fibers can vary depending upon the particular properties desired for the fibers and the web formation process. Typically, in an airlaid web, these thermoplastic fibers have a length from about 2 mm to about 12 mm long, preferably from about 2.5 mm to about 7.5 mm long, and most preferably from about 3.0 mm to about 6.0 mm long. The properties—of these thermoplastic fibers can also be adjusted by varying the diameter (caliper) of the fibers. The diameter of these thermoplastic fibers is typically defined in terms of either denier (grams per 9000 meters) or decitex (grams per 10,000 meters). Suitable bicomponent thermoplastic fibers as used in an airlaid making machine can have a decitex in the range from about 1.0 to about 20, preferably from about 1.4 to about 10, and most preferably from about 1.7 to about 7 decitex.

The compressive modulus of these thermoplastic materials, and especially that of the thermoplastic fibers, can also be important. The compressive modulus of thermoplastic fibers is affected not only by their length and diameter, but also by the composition and properties of the polymer or polymers from which they are made, the shape and configuration of the fibers (e.g., concentric or eccentric, crimped or uncrimped), and like factors. Differences in the compressive modulus of these thermoplastic fibers can be used to alter the properties, and especially the density characteristics, of the respective thermally bonded fibrous matrix.

The heterogeneous mass can also include synthetic fibers that typically do not function as binder fibers but alter the mechanical properties of the fibrous webs. Synthetic fibers include cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. These might include, for example, polyester fibers such as polyethylene terephthalate (e.g., DACRON® and KODEL®), high melting crimped polyester fibers (e.g., KODEL® 431 made by Eastman Chemical Co.) hydrophilic nylon (HYDROFIL®), and the like. Suitable fibers can also hydrophilized hydrophobic fibers, such as surfactant-treated or silica-treated thermoplastic fibers derived from, for example, polyolefins such as polyethylene or polypropylene, polyacrylics, polyamides, polystyrenes, polyurethanes and the like. In the case of nonbonding thermoplastic fibers, their length can vary depending upon the particular properties desired for these fibers. Typically they have a length from about 0.3 to 7.5 cm, preferably from about 0.9 to about 1.5 cm. Suitable nonbonding thermoplastic fibers can have a decitex in the range of about 1.5 to about 35 decitex, more preferably from about 14 to about 20 decitex.

However structured, the total absorbent capacity of the absorbent core should be compatible with the design loading and the intended use of the mass. For example, when used in an absorbent article, the size and absorbent capacity of the heterogeneous mass may be varied to accommodate different uses such as incontinence pads, pantiliners, regular sanitary napkins, or overnight sanitary napkins.

The heterogeneous mass can also include other optional components sometimes used in absorbent webs. For example, a reinforcing scrim can be positioned within the respective layers, or between the respective layers, of the heterogeneous mass.

The heterogeneous mass comprising open-cell foam pieces produced from the present invention may be used as an absorbent core or a portion of an absorbent core in absorbent articles, such as feminine hygiene articles, for example pads, pantiliners, and tampons; wound dressing; disposable diapers; incontinence articles, for example pads, adult diapers; homecare articles, for example wipes, pads, towels; and beauty care articles, for example pads, wipes, and skin care articles, such as used for pore cleaning. The absorbent structure having a topsheet and/or a secondary topsheet integrated into a heterogeneous mass layer having open-cell foam pieces may be used in absorbent articles such as feminine hygiene articles, for example pads, pantiliners, and tampons; wound dressings; disposable diapers; incontinence articles, for example pads, adult diapers; homecare articles, for example wipes, pads, towels; and beauty care articles, for example pads, wipes, and skin care articles, such as used for pore cleaning. A diaper may be an absorbent article as disclosed in U.S. patent application Ser. No. 13/428,404, filed on Mar. 23, 2012.

The absorbent core structure may be used as an absorbent core for an absorbent article. In such an embodiment, the absorbent core can be relatively thin, less than about 5 mm in thickness, or less than about 3 mm, or less than about 1 mm in thickness. Cores having a thickness of greater than 5 mm are also contemplated herein. Thickness can be determined by measuring the thickness at the midpoint along the longitudinal centerline of the pad by any means known in the art for doing while under a uniform pressure of 0.25 psi. The absorbent core can comprise absorbent gelling materials (AGM), including AGM fibers, blood gelling agents (e.g. chitosan), quaternary salts or combinations thereof as is known in the art.

The heterogeneous mass layer may be formed or cut to a shape, the outer edges of which define a periphery.

In an embodiment, the heterogeneous mass may be used as a topsheet for an absorbent article. The heterogeneous mass may be combined with an absorbent core or may only be combined with a backsheet.

In an embodiment, the heterogeneous mass may be combined with any other type of absorbent layer or non-absorbent layer such as, for example, a layer of cellulose, a layer comprising superabsorbent gelling materials, a layer of absorbent airlaid fibers, a nonwoven layer, or a layer of absorbent foam, or combinations thereof. Other absorbent layers not listed are contemplated herein.

In an embodiment, the open-cell foam pieces are in the form of stripes. The stripes may be formed during the formation of the heterogeneous mass or by formation means after polymerization. The stripes may run along the longitudinal length of the heterogeneous mass layer, along the lateral length of the heterogeneous mass layer, or a combination of both the longitudinal length and the lateral length. The stripes may run along a diagonal to either the longitudinal length or the lateral length of the heterogeneous mass layer. The stripes are separated by canals.

Formation means known for deforming a generally planar fibrous web into a three-dimensional structure are utilized in the present invention to modify as-made absorbent materials into absorbent materials having relatively higher permeability without a significant corresponding decrease in capillary pressure. Using formation means, one may create an absorbent structure by providing a first fibrous web material, wherein the first fibrous web material is a heterogeneous mass comprising one or more open cell foam pieces; providing a second fibrous web material; providing a pair of rolls forming a nip through which said first fibrous web material and second fibrous web material can be processed, said pair of rolls being selected from the processes consisting of ring rolling, SELF, micro-SELF, nested SELF, rotary knife aperturing, hot pin, 3D embossing, SAN, and embossed stabilized formation; and deforming both the first fibrous web material and the second fibrous web. The second fibrous web may be absorbent.

Formation means may comprise a pair of inter-meshing rolls, typically steel rolls having inter-engaging ridges or teeth and grooves. However, it is contemplated that other means for achieving formation can be utilized, such as the deforming roller and cord arrangement disclosed in US 2005/0140057 published Jun. 30, 2005. Therefore, all disclosure of a pair of rolls herein is considered equivalent to a roll and cord, and a claimed arrangement reciting two inter-meshing rolls is considered equivalent to an inter-meshing roll and cord where a cord functions as the ridges of a mating inter-engaging roll. In one embodiment, the pair of intermeshing rolls of the instant invention can be considered as equivalent to a roll and an inter-meshing element, wherein the inter-meshing element can be another roll, a cord, a plurality of cords, a belt, a pliable web, or straps. Likewise, other known formation technologies, such as creping, necking/consolidation, corrugating, embossing, button break, hot pin punching, and the like are believed to be able to produce absorbent materials having some degree of relatively higher permeability without a significant corresponding decrease in capillary pressure. Formation means utilizing rolls include "ring rolling", a "SELF" or "SELF'ing" process, in which SELF stands for Structural Elastic Like Film, as "micro-SELF", and "rotary knife aperturing" (RKA); as described in U.S. Pat. No. 7,935,207 Zhao et al., granted May 3, 2011. The formation means may be one of the formation means described in U.S. Pat. No. 7,682,686 (Curro et al.) granted on Mar. 23, 2010 or U.S. Pat. No. 7,648,752 (Hoying et al.) granted on Jan. 19, 2010. Suitable processes for constructing tufts are described in U.S. Pat. Nos. 7,172,801; 7,838,099; 7,754,050; 7,682,686; 7,410,683; 7,507,459; 7,553,532; 7,718,243; 7,648,752; 7,732,657; 7,789,994; 8,728,049; and 8,153,226. Formation means may also include Nested "SELF" as described below and in U.S. patent application Ser. No. 14/844,459 filed on Sep. 3, 2015. Formation means may also include hot pin, Selective Aperturing a Nonwoven (SAN) described in U.S. Pat. No. 5,628,097, 3D embossing and embossed stabilized formation as described in U.S. Patent Application No. 62/458,051 filed Feb. 13, 2017.

Referring to FIG. 1 there is shown in an apparatus and method for making web 1. The apparatus 100 comprises a pair of intermeshing rolls 174 and 176, each rotating about an axis A, the axes A being parallel in the same plane. Roll 174 comprises a plurality of ridges 172 and corresponding grooves 108 which extend unbroken about the entire circumference of roll 174. Roll 176 is similar to roll 174, but rather than having ridges that extend unbroken about the entire circumference, roll 176 comprises a plurality of rows of circumferentially-extending ridges that have been modified to be rows of circumferentially-spaced teeth 110 that extend in spaced relationship about at least a portion of roll 176. The individual rows of teeth 110 of roll 176 are separated by corresponding grooves 112. In operation, rolls 174 and 176 intermesh such that the ridges 172 of roll 174 extend into the grooves 112 of roll 176 and the teeth 110 of roll 176 extend into the grooves 108 of roll 174. The intermeshing is shown in greater detail in the cross sectional representation of FIG. 2, discussed below. Both or either of rolls 174 and 176 can be heated by means known in the art such as by using hot oil filled rollers or electrically-heated rollers.

In FIG. 1, the apparatus 100 is shown in a preferred configuration having one patterned roll, e.g., roll 176, and one non-patterned grooved roll 174. However, in certain embodiments it may be preferable to use two patterned rolls 176 having either the same or differing patterns, in the same or different corresponding regions of the respective rolls. Such an apparatus can produce webs with tufts 6 protruding from both sides of the web 1.

The method of making a web 1 in a commercially viable continuous process is depicted in FIG. 1. Web 1 is made by mechanically deforming precursor webs, such as first and second precursor webs, 180 and 21 that can each be described as generally planar and two dimensional prior to processing by the apparatus shown in FIG. 1. By "planar" and "two dimensional" is meant simply that the webs start the process in a generally flat condition relative to the finished web 1 that has distinct, out-of-plane, Z-direction three-dimensionality due to the formation of tufts 6. "Planar" and "two-dimensional" are not meant to imply any particular flatness, smoothness or dimensionality.

The process and apparatus of the present invention is similar in many respects to a process described in U.S. Pat. No. 5,518,801 entitled "Web Materials Exhibiting Elastic-Like Behavior" and referred to in subsequent patent literature as "SELF" webs, which stands for "Structural Elastic-like Film". However, there are significant differences between the apparatus and process of the present invention and the apparatus and process disclosed in the '801 patent, and the differences are apparent in the respective webs produced thereby. As described below, the teeth 110 of roll 176 have a specific geometry associated with the leading and trailing edges that permit the teeth to essentially "punch" through the precursor webs 180, 21 as opposed to, in essence, deforming the web. In a two layer laminate web 1 the teeth 110 urge fibers from precursor webs 180 and 21 out-of-plane by the teeth 110 pushing the fibers 8 through to form tufts 6. Therefore, a web 1 can have tufts 6 comprising loose fiber ends 18 and/or "tunnel-like" tufts 6 of looped, aligned fibers 8 extending away from the surface 13 of side 3, unlike the "tent-like" rib-like elements of SELF webs which each have continuous side walls associated therewith, i.e., a continuous "transition zone," and which do not exhibit interpenetration of one layer through another layer.

Precursor webs 180 and 21 are provided either directly from their respective web making processes or indirectly from supply rolls (neither shown) and moved in the machine direction to the nip 116 of counter-rotating intermeshing rolls 174 and 176. The precursor webs are preferably held in a sufficient web tension so as to enter the nip 16 in a generally flattened condition by means well known in the art of web handling. As each precursor web 180, 21 goes through the nip 116 the teeth 110 of roll 176 which are intermeshed with grooves 108 of roll 174 simultaneously urge portions of precursor webs 180 and 21 out of the plane to form tufts 6. In one embodiment, teeth 110 in effect "push" or "punch" fibers of first precursor web 180 through second precursor web 21. In another embodiment teeth 110 in effect "push" or "punch" fibers of both first and second precursor webs 180 and 21 out of plane to form tufts 6.

Figure 3:
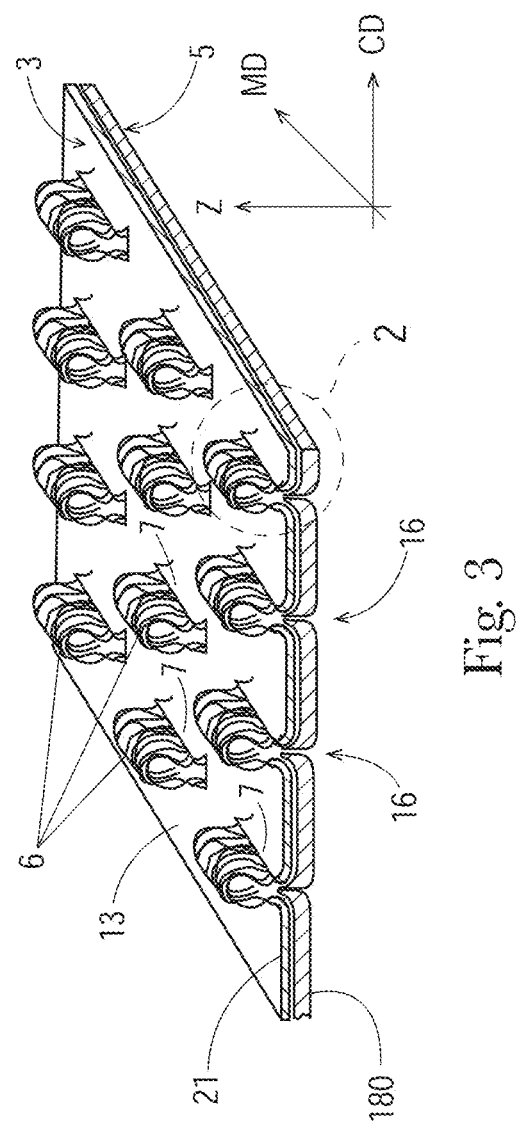
FIG. 3 is a perspective view of a web suitable for use in an article.
Figure 4:
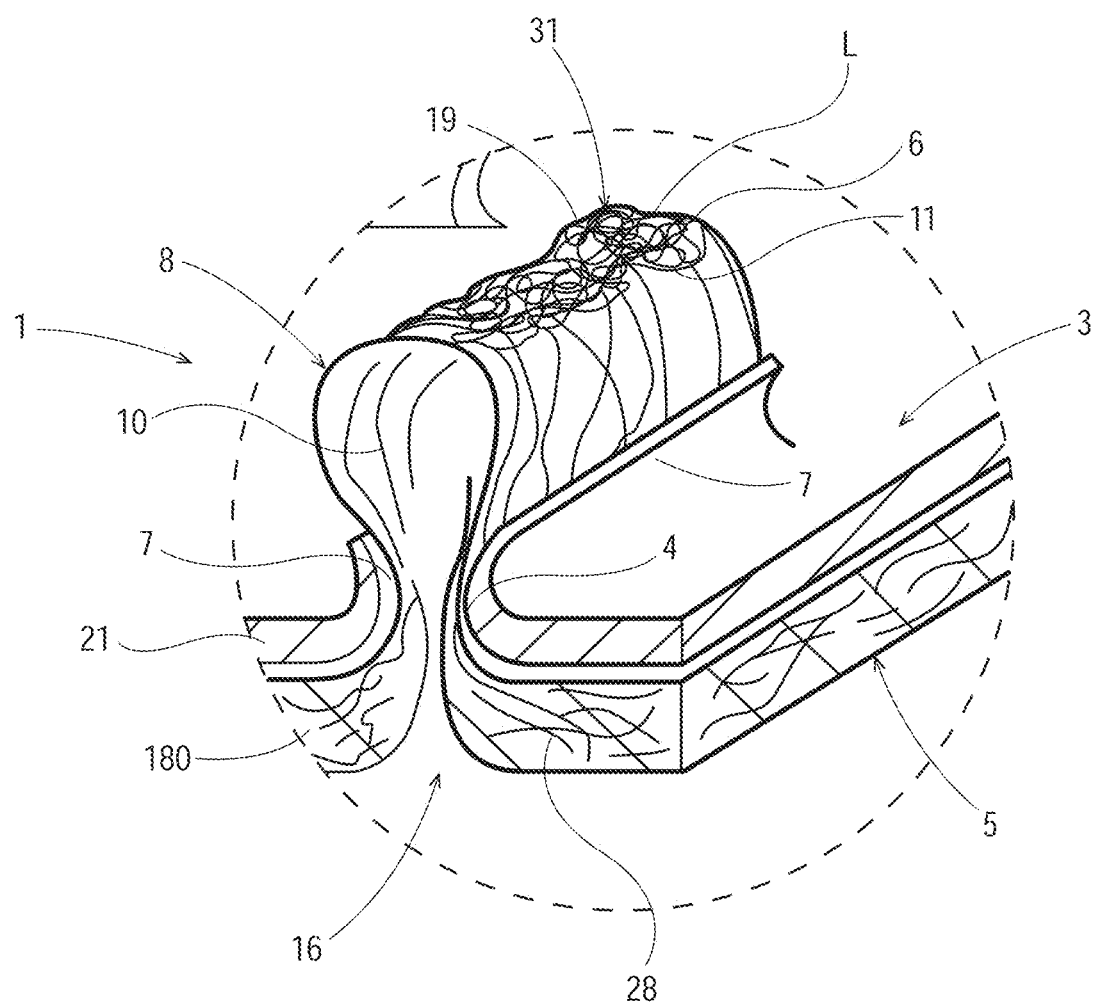
FIG. 4 is an enlarged view of a portion of the web shown in FIG. 3.

As the tip of teeth 110 push through first and second precursor webs 180, 21 the portions of the fibers of first precursor web 180 (and, in some embodiments, second precursor web 21) that are oriented predominantly in the CD across teeth 110 are urged by the teeth 110 out of the plane of first precursor web 180. Fibers can be urged out of plane due to fiber mobility, or they can be urged out of plane by being stretched and/or plastically deformed in the Z-direction. Portions of the precursor webs urged out of plane by teeth 110 results in formation of tufts 6 on first side 3 of web 1. Fibers of precursor webs 180 and 21 that are predominantly oriented generally parallel to the longitudinal axis L, i.e., in the MD as shown in FIG. 3, are simply spread apart by teeth 110 and remain substantially in their original, randomly-oriented condition. This is why the looped fibers 8 can exhibit the unique fiber orientation in embodiments such as the one shown in FIGS. 3-4, which is a high percentage of fibers of each tuft 6 having a significant or major vector component parallel to the transverse axis T of tuft 6.

It can be appreciated by the forgoing description that when web 1 is made by the apparatus and method of the present invention that the precursor webs 180, 21 can possess differing material properties with respect to the ability of the precursor webs to elongate before failure, e.g., failure due to tensile stresses. In one embodiment, a nonwoven first precursor web 180 can have greater fiber mobility and/or greater fiber elongation characteristics relative to second precursor web 21, such that the fibers thereof can move or stretch sufficiently to form tufts 6 while the second precursor web 21 ruptures, i.e., does not stretch to the extent necessary to form tufts. In another embodiment, second precursor web 21 can have greater fiber mobility and/or greater fiber elongation characteristics relative to first precursor web 180, such that both first and second precursor webs 180 and 21 form tufts 6. In another embodiment, second precursor web 21 can have greater fiber mobility and/or greater fiber elongation characteristics relative to first precursor web 180, such that the fibers of second precursor web 21 can move or stretch sufficiently to form tufts 6 while the first precursor web 180 ruptures, i.e., does not stretch to the extent necessary to form tufts.

The degree to which the fibers of nonwoven precursor webs are able to extend out of plane without plastic deformation can depend upon the degree of inter-fiber bonding of the precursor web. For example, if the fibers of a nonwoven precursor web are only very loosely entangled to each other, they will be more able to slip by each other (i.e., to move relative to adjacent fibers by reptation) and therefore be more easily extended out of plane to form tufts. On the other hand, fibers of a nonwoven precursor web that are more strongly bonded, for example by high levels of thermal point bonding, hydroentanglement, or the like, will more likely require greater degrees of plastic deformation in extended out-of-plane tufts. Therefore, in one embodiment, one precursor web 180 or 21 can be a nonwoven web having relatively low inter-fiber bonding, and the other precursor web 180 or 21 can be a nonwoven web having relatively high inter-fiber bonding, such that the fibers of one precursor web can extend out of plane, while the fibers of the other precursor web cannot.

In one embodiment, for a given maximum strain (e.g., the strain imposed by teeth 110 of apparatus 100), it is beneficial that second precursor web 21 actually fail under the tensile loading produced by the imposed strain. That is, for the tufts 6 comprising only, or primarily, fibers from first precursor web 180 to be disposed on the first side 3 of web 1, second precursor web 21 must have sufficiently low fiber mobility (if any) and/or relatively low elongation-to-break such that it locally (i.e., in the area of strain) fails in tension, thereby producing openings 4 through which tufts 6 can extend.

In another embodiment it is beneficial that second precursor web 21 deform or stretch in the region of induced strain, and does not fail, such that tuft 6 includes portions of second precursor web 21.

In one embodiment second precursor web 21 has an elongation to break in the range of 1%-5%. While the actual required elongation to break depends on the strain to be induced to form web. 1, it is recognized that for most embodiments, second precursor web 21 can exhibit a web elongation-to-break of 6%, 7%, 8%, 9%, 10%, or more. It is also recognized that actual elongation-to-break can depend on the strain rate, which, for the apparatus shown in FIG. 1 is a function of line speed. Elongation to break of webs used in the present invention can be measured by means known in the art, such as by standard tensile testing methods using standard tensile testing apparatuses, such as those manufactured by Instron, MTS, Thwing-Albert, and the like.

Relative to first precursor web 180, second precursor web 21 can have lower fiber mobility (if any) and/or lower elongation-to-break (i.e., elongation-to-break of individual fibers, or, if a film, elongation-to-break of the film) such that, rather than extending out-of-plane to the extent of the tufts 6, second precursor web 21 fails in tension under the strain produced by the formation of tufts 6, e.g., by the teeth 110 of apparatus 100. In one embodiment, second precursor web 21 exhibits sufficiently low elongation-to-break relative to first precursor web 180 such that flaps 7 of opening 4 only extend slightly out-of-plane, if at all, relative to tufts 6. In general, for embodiments in which tufts 6 comprise primarily fibers from first precursor web 180, it is believed that second precursor web 21 should have an elongation to break of at least 10% less than the first precursor web 180, preferably at least 30% less, more preferably at least 50% less, and even more preferably at least about 100% less than that of first precursor web 180. Relative elongation to break values of webs used in the present invention can be measured by means known in the art, such as by standard tensile testing methods using standard tensile testing apparatuses, such as those manufactured by Instron, MTS, Thwing-Albert, and the like.

In one embodiment second precursor web 21 can comprise substantially all MD-oriented fibers, e.g., tow fibers, such that there are substantially no fibers oriented in the CD. For such an embodiment of web 1 the fibers of second precursor web 21 can simply separate at the opening 4 through which tufts 6 extend. In this embodiment, therefore, second precursor web 21 need not have any minimum elongation to break, since failure or rupture of the material is not the mode of forming opening 4.

The number, spacing, and size of tufts 6 can be varied by changing the number, spacing, and size of teeth 110 and making corresponding dimensional changes as necessary to roll 176 and/or roll 174. This variation, together with the variation possible in precursor webs 180, 21 permits many varied webs 1 having varied fluid handling properties for use in a disposable absorbent article. As described more fully below, a web 1 comprising a nonwoven/film first precursor web/second precursor web combination can also be used as a component in disposable absorbent articles. However, even better results are obtained in a nonwoven/nonwoven precursor web/second precursor web combination wherein fibers from both webs contribute to tufts 6.

Figure 2:
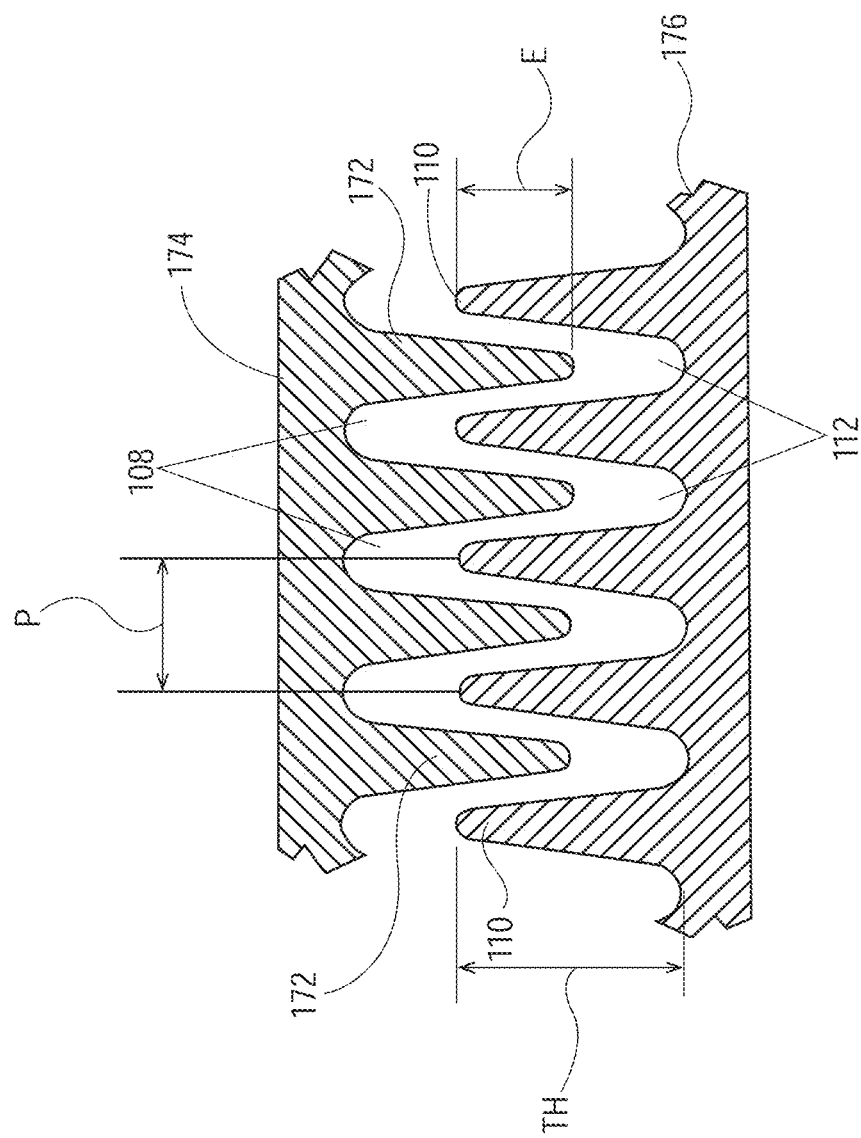
FIG. 2 is a cross-sectional depiction of a portion of the apparatus shown in FIG. 1.

FIG. 2 shows in cross section a portion of the intermeshing rolls 174 and 176 and ridges 172 and teeth 110. As shown teeth 110 have a tooth height TH (note that TH can also be applied to ridge height; in a preferred embodiment tooth height and ridge height are equal), and a tooth-to-tooth spacing (or ridge-to-ridge spacing) referred to as the pitch P. As shown, depth of engagement E is a measure of the level of intermeshing of rolls 174 and 176 and is measured from tip of ridge 172 to tip of tooth 110. The depth of engagement E, tooth height TH, and pitch P can be varied as desired depending on the properties of precursor webs 180, 21 and the desired characteristics of web 1. For example, in general, the greater the level of engagement E, the greater the necessary elongation or fiber-to-fiber mobility characteristics the fibers of portions of the precursor webs intended to form tufts must possess. Also, the greater the density of tufts 6 desired (tufts 6 per unit area of web 1), the smaller the pitch should be, and the smaller the tooth length TL and tooth distance TD should be, as described below.

Figure 5:
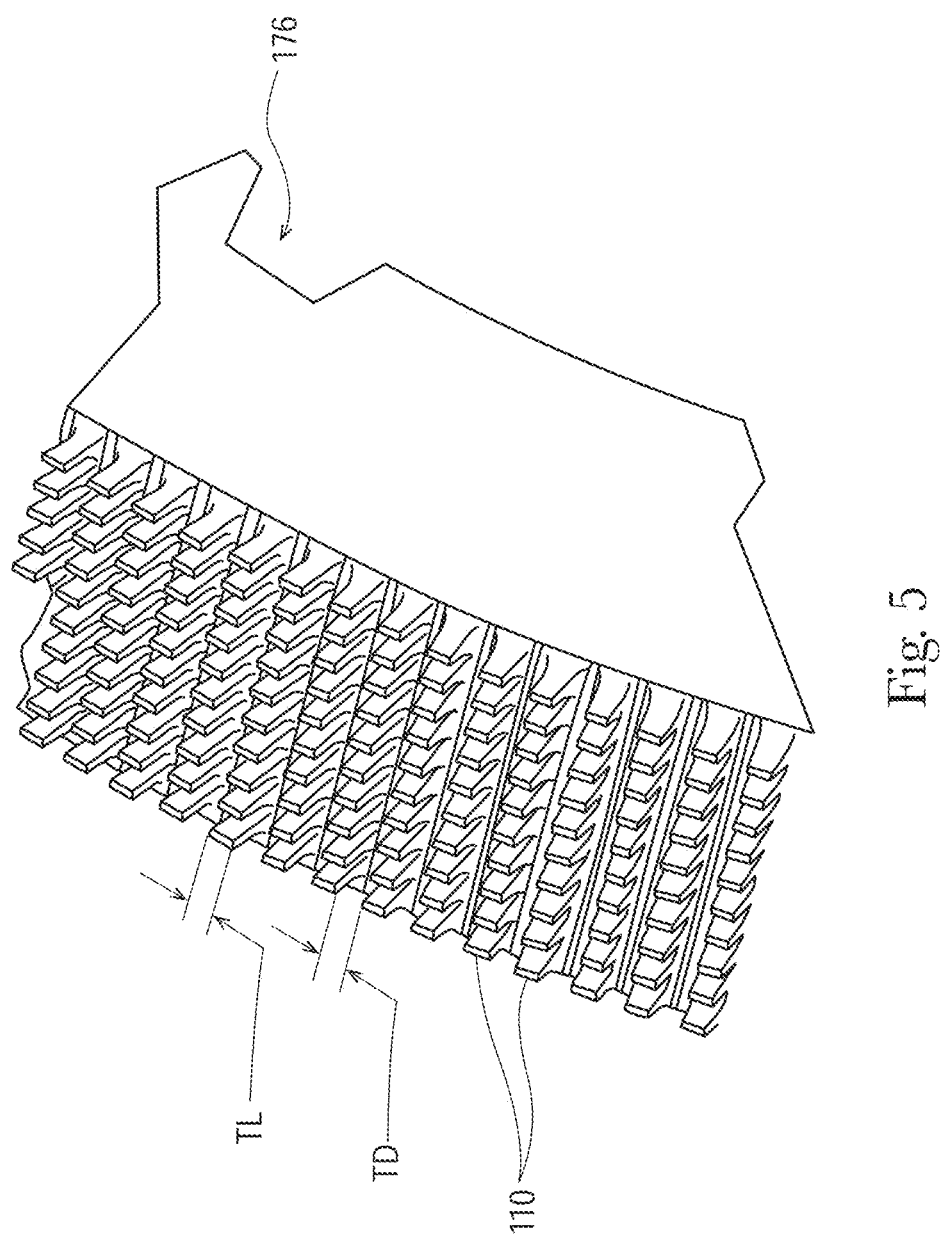
FIG. 5 is a perspective view of a portion of the apparatus for forming one embodiment of a web suitable for use in an article.

FIG. 5 shows one embodiment of a roll 176 having a plurality of teeth 110 useful for making a web 1 from a nonwoven first precursor web 180 having a basis weight of between about 60 gsm and 100 gsm, preferably about 80 gsm and a polyolefinic film (e.g., polyethylene or polypropylene) second precursor web 21 having a density of about 0.91-0.94 and a basis weight of about 180 gsm.

Figure 6:
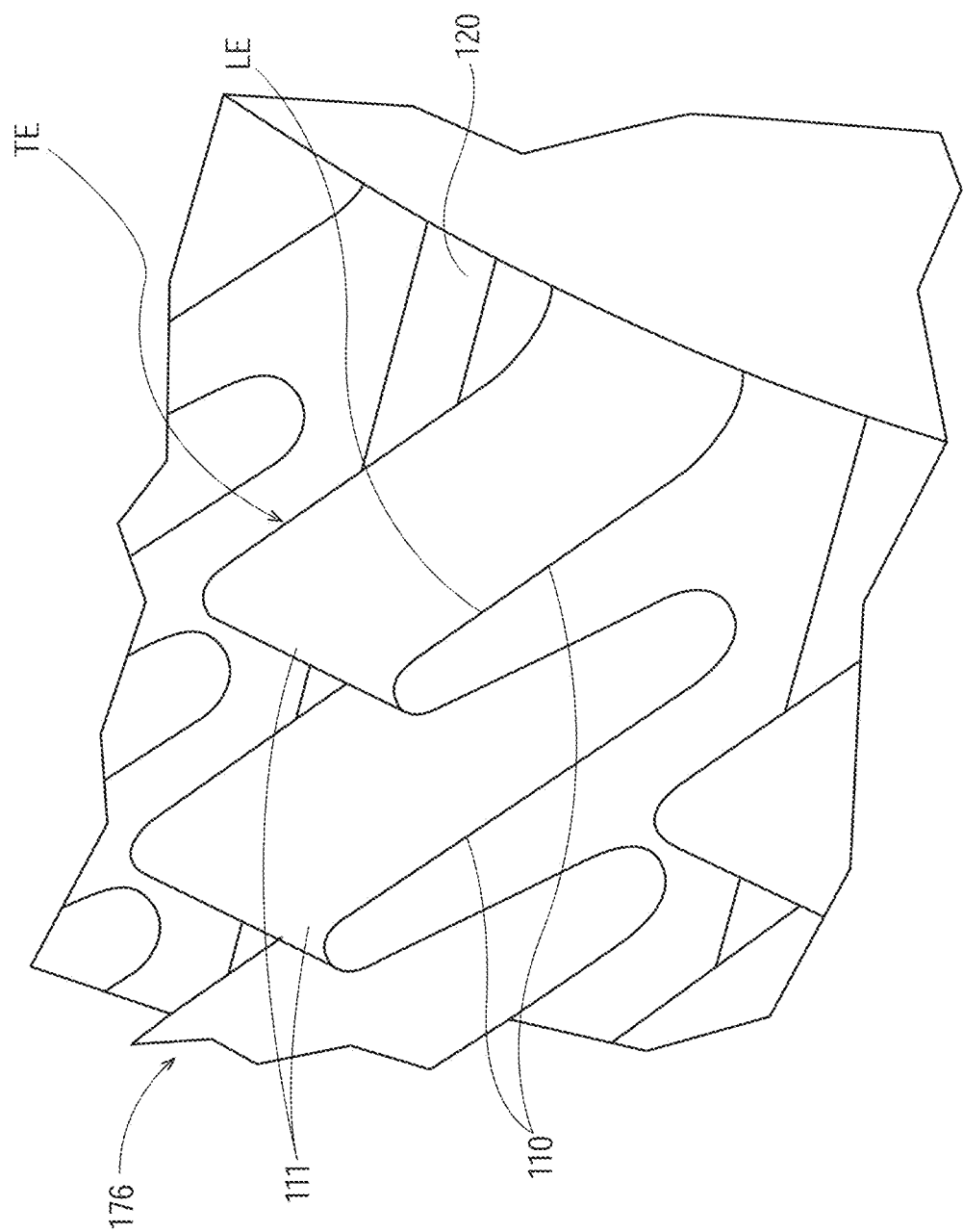
FIG. 6 is an enlarged perspective view of a portion of the apparatus for forming a web suitable for use in an article.

An enlarged view of teeth 110 is shown in FIG. 6. In this embodiment of roll 176 teeth 110 have a uniform circumferential length dimension TL measured generally from the leading edge LE to the trailing edge TE at the tooth tip 111 of about 1.25 mm and are uniformly spaced from one another circumferentially by a distance TD of about 1.5 mm. For making a terry-cloth web 1 from web 1 having a total basis weight in the range of about 60 to about 100 gsm, teeth 110 of roll 176 can have a length TL ranging from about 0.5 mm to about 10 mm and a spacing TD from about 0.5 mm to about 10 mm, a tooth height TH ranging from about 0.5 mm to about 10 mm, and a pitch P between about 1 mm (0.040 inches) and about 5 mm (0.1800 inches). Depth of engagement E can be from about 0.5 mm to about 10 mm (up to a maximum equal to tooth height TH). Of course, E, P, TH, TD and TL can be varied independently of each other to achieve a desired size, spacing, and area density of tufts 6 (number of tufts 6 per unit area of web 1).

As shown in FIG. 6, each tooth 110 has a tip 111, a leading edge LE and a trailing edge TE. The tooth tip 111 is elongated and has a generally longitudinal orientation, corresponding to the longitudinal axes L of tufts 6 and discontinuities 16. It is believed that to get the tufted, looped tufts 6 of the web 1 that can be described as being terry cloth-like, the LE and TE should be very nearly orthogonal to the local peripheral surface 1180 of roll 176. As well, the transition from the tip 111 and LE or TE should be a sharp angle, such as a right angle, having a sufficiently small radius of curvature such that teeth 110 push through second precursor web 21 at the LE and TE. Without being bound by theory, it is believed that having relatively sharply angled tip transitions between the tip of tooth 110 and the LE and TE permits the teeth 110 to punch through precursor webs 180, 21 "cleanly", that is, locally and distinctly, so that the first side 3 of the resulting web 1 can be described as "tufted" rather than "deformed." When so processed, the web 1 is not imparted with any particular elasticity, beyond what the precursor webs 180 and 21 may have possessed originally.

Figure 7:
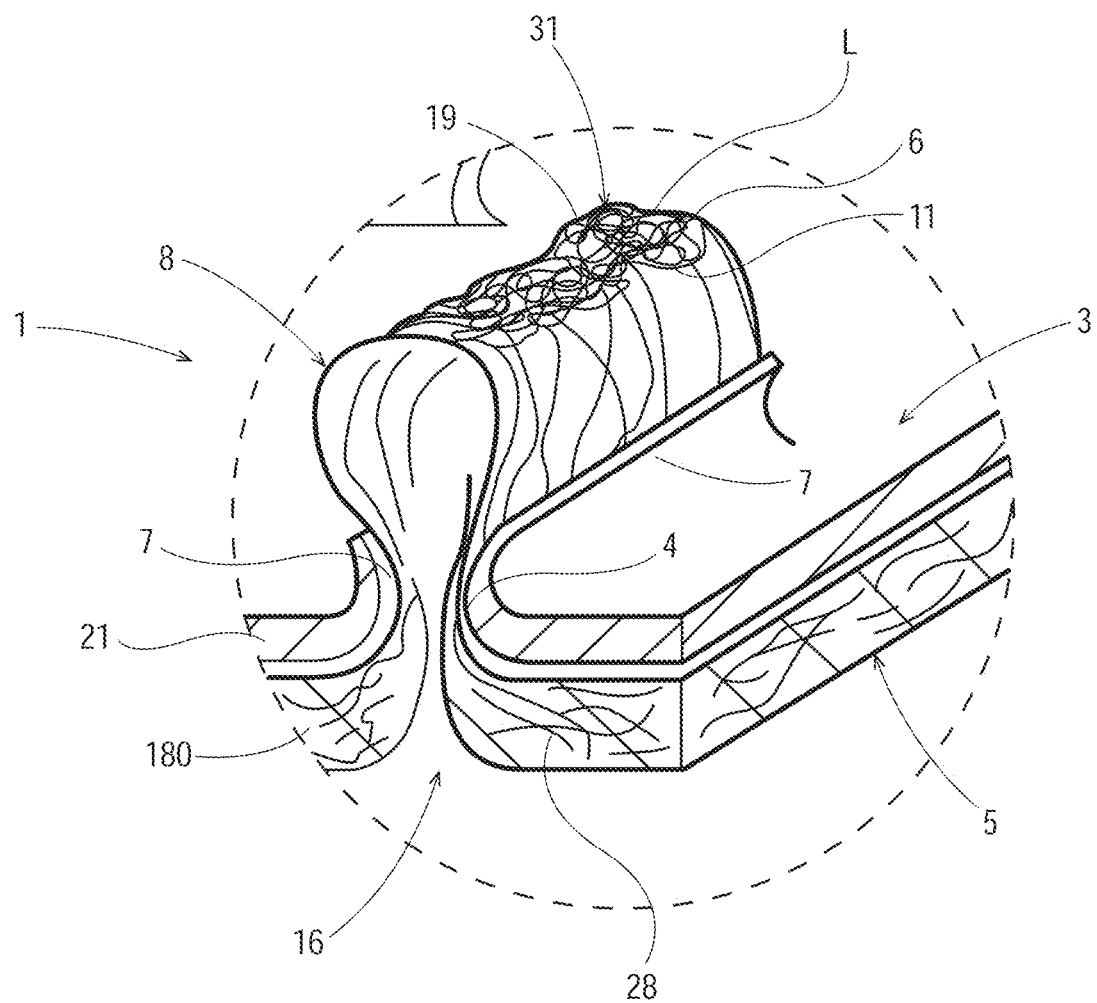
FIG. 7 is an enlarged view of a portion of another embodiment of a web suitable for use in an article.

At higher line speeds, i.e., relatively higher rates of processing of the web through the nip of rotating rolls 174 and 176, like materials can exhibit very different structures for tufts 6. The tuft 6 shown in FIG. 7 is similar in structure to the tuft shown in FIG. 4 but exhibits a very different structure, a structure that appears to be typical of spunbond nonwoven first precursor webs 180 processed to form tufts 6 at relatively high speeds, i.e., at high strain rates. Typical of this structure is broken fibers between the proximal portion, i.e., base 7, of tufts 6 and the distal portion, i.e., the top 31, of tuft 6, and what appears to be a "mat" 19 of fibers at the top of the tuft 6. Mat 19 comprises and is supported at the top of tufts 6 by unbroken, looped fibers 8, and also comprises portions of broken fibers 11 that are no longer integral with first precursor web 180. That is, mat 19 comprises fiber portions which were formerly integral with precursor web 180 but which are completely detached from precursor web 180 after processing at sufficiently high line speeds, e.g., 30 meters per minute line speed in the process described with reference to FIG. 1.

Therefore, from the above description, it is understood that in one embodiment web 1 can be described as being a laminate web formed by selective mechanical deformation of at least a first and second precursor webs, at least the first precursor web being a nonwoven web, the laminate web having a first garment-facing, side, the first garment-facing side comprising the second precursor web and a plurality of discrete tufts, each of the discrete tufts comprising fibers integral with but extending from the first precursor web and fibers neither integral with nor extending from the first precursor web.

Figure 8:
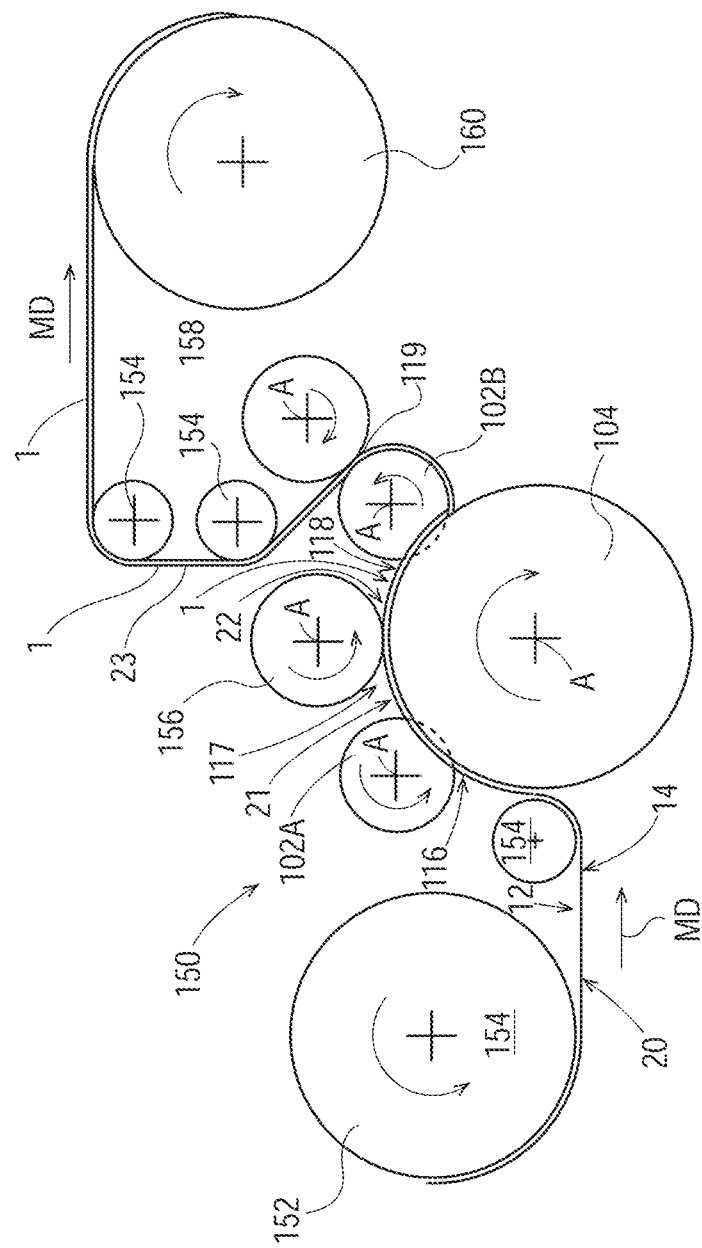
FIG. 8 is a schematic representation of an apparatus for making a web.

As shown in FIG. 8, after tufts 6 are formed, tufted precursor web 21 travels on rotating roll 104 to nip 117 between roll 104 and a first bonding roll 156. Bonding roll 156 can facilitate a number of bonding techniques. For example, bonding roll 156 can be a heated steel roller for imparting thermal energy in nip 117, thereby melt-bonding adjacent fibers of tufted web 21 at the distal ends (tips) of tufts 6. Bonding roll 156 can also facilitate thermal bonding by means of pressure only, or use of heat and pressure. In one embodiment, for example, nip 117 can be set at a width sufficient to compress the distal ends of tufts 6, which at high rates of processing can cause thermal energy transfer to the fibers, which can then reflow and bond.

Depending on the type of bonding being facilitated, bonding roll 156 can be a smooth, steel surface, or a relatively soft, flexible surface. In a preferred embodiment, as discussed in the context of a preferred web below, bonding roll 156 is a heated roll designed to impart sufficient thermal energy to tufted web 21 so as to thermally bond adjacent fibers of the distal ends of tufts 6. Thermal bonding can be by melt-bonding adjacent fibers directly, or by melting an intermediate thermoplastic agent, such as polyethylene powder, which in turn, adheres adjacent fibers. Polyethylene powder can be added to precursor web 20 for such purposes.

First bonding roll 156 can be heated sufficiently to melt or partially melt fibers 8 or 18 at the distal ends 3 of tufts 6. The amount of heat or heat capacity necessary in first bonding roll 156 depends on the melt properties of the fibers of tufts 6 and the speed of rotation of roll 104. The amount of heat necessary in first bonding roll 156 also depends on the pressure induced between first bonding roll 156 and tips of teeth 110 on roll 104, as well as the degree of melting desired at distal ends 3 of tufts 6. In one embodiment, bonding roll 156 can provide sufficient heat and pressure to not only melt bond fibers at the distal ends 3 of tufts 6, but also cut through the bonded portion so as to, in effect, cut through the end of tuft 6. In such an embodiment, the tuft is divided into two portions, but is not longer looped. In one embodiment, pressure alone can cause the looped portion of the tuft to be cut through, thereby rendering the tufts 6 to be un-looped tufts of fiber free ends. Other methods known in the art, such as use of a spinning wire brush wheel can also be utilized to cut the loops of looped fibers to form un-looped tufts.

In one embodiment, first bonding roll 156 is a heated steel cylindrical roll, heated to have a surface temperature sufficient to melt-bond adjacent fibers of tufts 6. First bonding roll can be heated by internal electrical resistance heaters, by hot oil, or by any other means known in the art for making heated rolls. First bonding roll 156 can be driven by suitable motors and linkages as known in the art. Likewise, first bonding roll can be mounted on an adjustable support such that nip 117 can be accurately adjusted and set.

Nested "SELF" relates to a method that includes making a fibrous materials by a method comprising the steps of: a) providing at least one precursor nonwoven web; b) providing an apparatus comprising a pair of forming members comprising a first forming member (a "male" forming member) and a second forming member (a "female" forming member); and c) placing the precursor nonwoven web(s) between the forming members and mechanically deforming the precursor nonwoven web(s) with the forming members. The forming members have a machine direction (MD) orientation and a cross-machine direction (CD) orientation.

The first and second forming members can be plates, rolls, belts, or any other suitable types of forming members. In the embodiment of the apparatus 200 shown in FIG. 9, the first and second forming members 182 and 190 are in the form of non-deformable, meshing, counter-rotating rolls that form a nip 188 therebetween. The precursor web(s) is/are fed into the nip 188 between the rolls 182 and 190. Although the space between the rolls 182 and 190 is described herein as a nip, as discussed in greater detail below, in some cases, it may be desirable to avoid compressing the precursor web(s) to the extent possible.

First Forming Member.

The first forming member (such as "male roll") 182 has a surface comprising a plurality of first forming elements which comprise discrete, spaced apart male forming elements 112. The male forming elements are spaced apart in the machine direction and in the cross-machine direction.

As shown in FIG. 10, the male forming elements 112 have a base 186 that is joined to (in this case is integral with) the first forming member 182, a top 184 that is spaced away from the base, and side walls (or "sides") 120 that extend between the base 186 and the top 184 of the male forming elements. The male elements 112 may also have a transition portion or region 122 between the top 184 and the side walls 120. The male elements 112 also have a plan view periphery, and a height $H_1$ (the latter being measured from the base 186 to the top 184). The discrete elements on the male roll may have a top 184 with a relatively large surface area (e.g., from about 1 mm to about 10 mm in width, and from about 1 mm to about 20 mm in length) for creating a wide deformation. The male elements 112 may, thus, have a plan view aspect ratio (ratio of length to width) that ranges from about 1:1 to about 10:1. For the purpose of determining the aspect ratio, the larger dimension of the male elements 112 will be consider the length, and the dimension perpendicular thereto will be considered to be the width of the male element. The male elements 112 may have any suitable configuration.

The base 186 and the top 184 of the male elements 112 may have any suitable plan view configuration, including but not limited to: a rounded diamond configuration as shown in FIGS. 9 and 10, an American football-like shape, triangle, circle, clover, a heart-shape, teardrop, oval, or an elliptical shape. The configuration of the base 186 and the configuration of the top 184 of the male elements 112 may be in any of the following relationships to each other: the same, similar, or different. The top 184 of the male elements 112 can be flat, rounded, or any configuration therebetween.

Figure 10A:
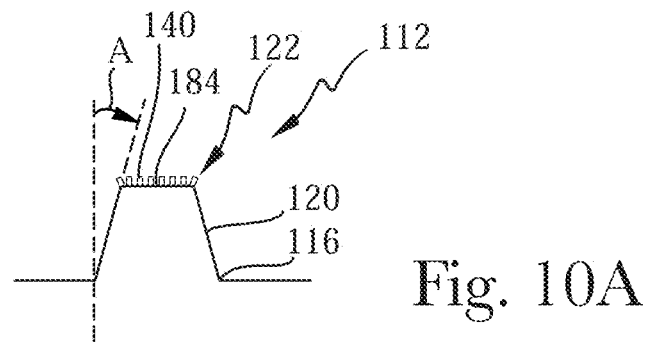
FIG. 10A is an enlarged schematic side view showing an example of a surface texture formed by knurling a forming member.
Figure 10B:
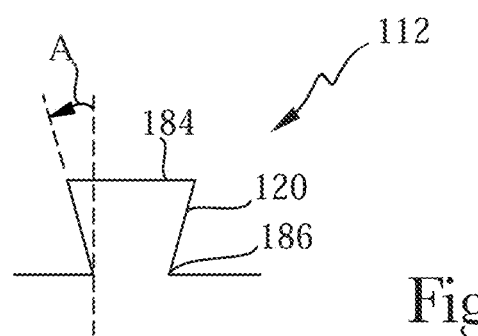
FIG. 10B is a schematic side view of a male element with undercut side walls.
Figure 10C:
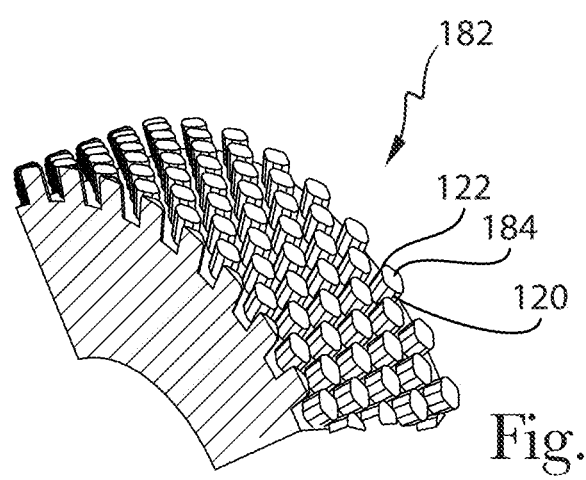
FIG. 10C is an enlarged perspective view of a portion of a male roll having an alternative configuration.
Figure 10D:
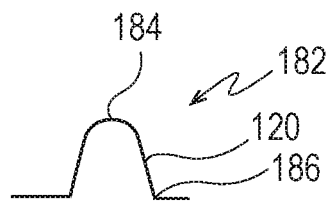
FIG. 10D is a schematic side view of a male element with a rounded top.
Figure 10E:
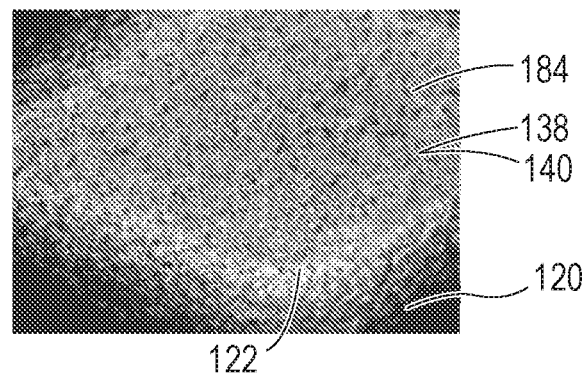
FIG. 10E is a magnified photograph of the top surface of a male element that has been roughened by sandblasting.
Figure 10F:
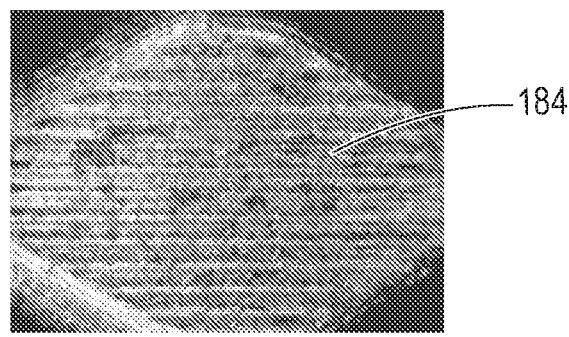
FIG. 10F is a magnified photograph of the top surface of a male element that has a relatively smooth surface formed by machining the same.

The transition region or "transition" 122 between the top 184 and the side walls 120 of the male elements 112 may also be of any suitable configuration. The transition 122 can be in the form of a sharp edge (as shown in FIG. 10C) in which case there is zero, or a minimal radius where the side walls 120 and the top 184 of the male elements meet. That is, the transition 122 may be substantially angular, sharp, non-radiused, or non-rounded. In other embodiments, such as shown in FIG. 10, the transition 122 between the top 184 and the side walls 120 of the male elements 112 can be radiused, or alternatively beveled. Suitable radiuses include, but are not limited to: zero (that is, the transition forms a sharp edge), 0.01 inch (about 0.25 mm), 0.02 inch (about 0.5 mm), 0.03 inch (about 0.76 mm), 0.04 inch (about 1 mm) (or any 0.01 inch increment above 0.01 inch), up to a fully rounded male element as shown in FIG. 10D.

In some cases, it may be desired to roughen the surface of all, or a portion, of the male elements 112. The surface of the male elements 112 can be roughened in any suitable manner. The surface of the male elements 112 can be roughened, for example, by: media blasting (that is, roughened with shot or "shot blasted"); wet blasting (roughed with water jets); plasma coating, machining, or knurling (i.e., pressure embossing of surface of first forming member); or combinations of the same. The roughened configuration and characteristics of the male elements 112 will depend on the type of process used to roughen the same. The roughening will typically provide at least the top 184 of at least some of the male elements 112 with greater than or equal to two discrete first surface texture elements protruding therefrom.

Second Forming Member.

As shown in FIG. 9, the second forming member (such as "female roll") 190 has a surface 124 having a plurality of cavities or recesses 114 therein. The recesses 114 are aligned and configured to receive the male forming elements 112 therein. Thus, the male forming elements 112 mate with the recesses 114 so that a single male forming element 112 fits within the periphery of a single recess 114, and at least partially within the recess 114 in the z-direction. The recesses 114 have a plan view periphery 126 that is larger than the plan view periphery of the male elements 112. As a result, the recess 114 on the female roll may completely encompass the discrete male element 112 when the rolls 182 and 190 are intermeshed. The recesses 114 have a depth $D_1$ shown in FIG. 11. In some cases, the depth $D_1$ of the recesses may be greater than the height $H_1$ of the male forming elements 112.

The recesses 114 have a plan view configuration, side walls 128, a top edge or rim 134 around the upper portion of the recess where the side walls 128 meet the surface 124 of the second forming member 190, and a bottom edge 130 around the bottom 132 of the recesses where the side walls 128 meet the bottom 132 of the recesses.

The recesses 114 may have any suitable plan view configuration provided that the recesses can receive the male elements 112 therein. The recesses 114 may have a similar plan view configuration as the male elements 112. In other cases, some or all of the recesses 114 may have a different plan view configuration from the male elements 112.

Figure 11:
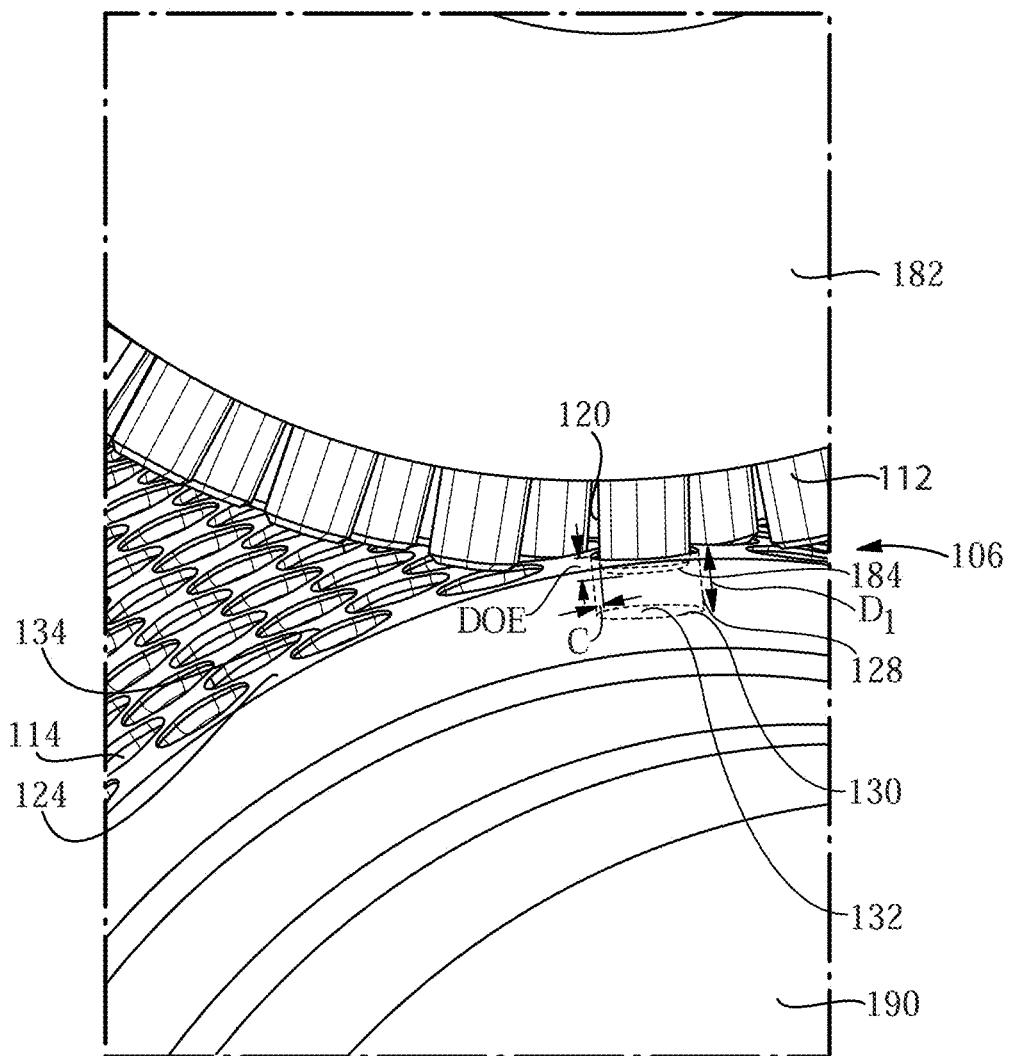
FIG. 11 is an enlarged perspective view showing the nip between the rolls shown in FIG. 9.
Figure 11A:
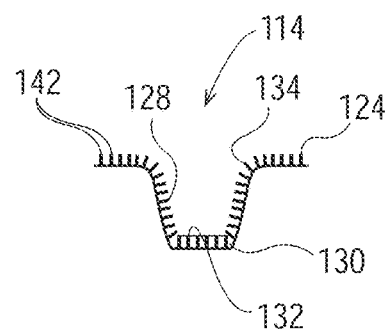
FIG. 11A is a schematic side view of a recess in a female forming member with a rounded top edge or rim.
Figure 11B:
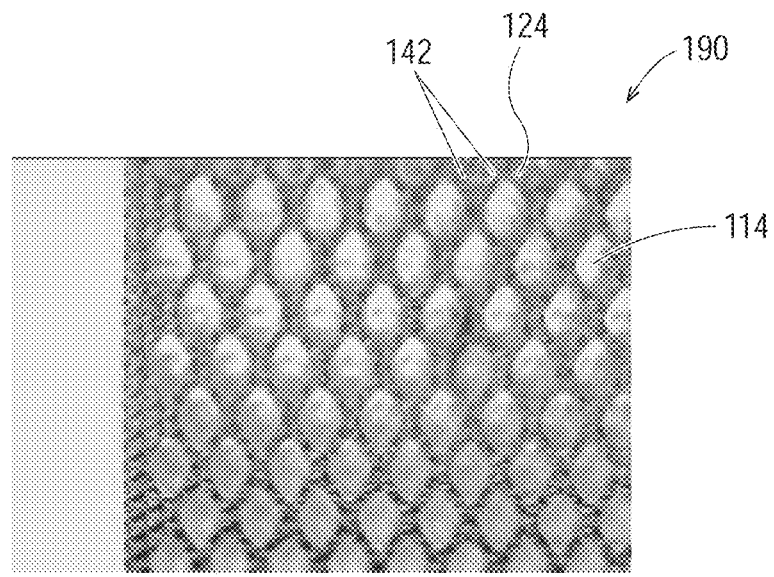
FIG. 11B is a photograph of a second forming member having a surface that has been roughened with diamond type knurling.

The top edge or rim 134 around the upper portion of the recess where the side walls 128 meet the surface 124 of the second forming member 190 may have any suitable configuration. The rim 134 can be in the form of a sharp edge (as shown in FIG. 11) in which case there is zero, or a minimal radius where the side walls 128 of the recesses meet the surface of the second forming member 190. That is, the rim 134 may be substantially angular, sharp, non-radiused, or non-rounded. In other embodiments, such as shown in FIG. 11A, the rim 134 can be radiused, or alternatively beveled. Suitable radiuses include, but are not limited to: zero (that is, form a sharp edge), 0.01 inch (about 0.25 mm), 0.02 inch (about 0.5 mm), 0.03 inch (about 0.76 mm), 0.04 inch (about 1 mm) (or any 0.01 inch increment above 0.01 inch) up to a fully rounded land area between some or all of the side walls 128 around each recess 114. The bottom edge 130 of the recesses 114 may be sharp or rounded.

Figure 10G:
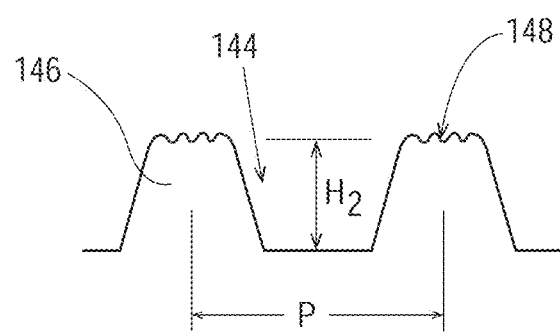
FIG. 10G is a schematic side view showing an example of macro texture and micro texture that can be created by knurling the surface of a male or female forming member.

In some cases, it may be desired to roughen the surface of all, or a portion, of the second forming member 190 and/or recesses 114 by providing the same with a plurality of discrete second surface texture elements 142 thereon. The surface of the second forming member 190 and/or recesses 114 can be roughened in any of the manners described above for roughening the surface of the male elements 112. This may provide the surface of the second forming member 190 and/or recesses 114 with second surface texture elements 142 (and/or valleys 144, raised areas 146, and microscale texture 148 as shown in FIG. 10G) having the same or similar properties as the first surface texture elements 140 on the male elements 112. Thus, the second surface texture elements 142 can be distributed on the surface of the second forming member 190 in a regular pattern or a random pattern.

The depth of engagement (DOE) is a measure of the level of intermeshing of the forming members. As shown in FIG. 11, the DOE is measured from the top 184 of the male elements 112 to the (outermost) surface 124 of the female forming member 114 (e.g., the roll with recesses). The DOE may, for example, range from at least about 1.5 mm, or less, to about 5 mm, or more. In certain embodiments, the DOE may be between about 2.5 mm to about 5 mm, alternatively between about 3 mm and about 4 mm.

As shown in FIG. 11, there is a clearance, C, between the sides 120 of the male elements 112 and the sides (or side walls) 128 of the recesses 114. The clearances and the DOE's are related such that larger clearances can permit higher DOE's to be used. The clearance, C, between male and female roll may be the same, or it may vary around the perimeter of the male element 112. For example, the forming members can be designed so that there is less clearance between the sides of the male elements 112 and the adjacent side walls 128 of the recesses 114 than there is between the side walls at the end of the male elements 112 and the adjacent side walls of the recesses 114. In other cases, the forming members can be designed so that there is more clearance between the sides 120 of the male elements 112 and the adjacent side walls 128 of the recesses 114 than there is between the side walls at the end of the male elements 112 and the adjacent side walls of the recesses. In still other cases, there could be more clearance between between the side wall on one side of a male element 112 and the adjacent side wall of the recess 114 than there is between the side wall on the opposing side of the same male element 112 and the adjacent side wall of the recess. For example, there can be a different clearance at each end of a male element 112; and/or a different clearance on each side of a male element 112. Clearances can range from about 0.005 inches (about 0.1 mm) to about 0.1 inches (about 2.5 mm).

The precursor nonwoven web 30 is placed between the forming members 182 and 190. The precursor nonwoven web can be placed between the forming members with either side of the precursor web (first surface 34 or second surface 36) facing the first forming member, male forming member 182. For convenience of description, the second surface 36 of the precursor nonwoven web will be described herein as being placed in contact with the first forming member 182. (Of course, in other embodiments, the second surface 36 of the precursor nonwoven web can be placed in contact with the second forming member 190.)

The Nested SELF process can create wells that are larger in diameter (ie. >1 mm). The bottom of the well can be pushed downward with little to no fracturing of the material within the well. The Nested SELF process could also comprise a roll with ridges and grooves, with the ridges being broken about the circumference by discrete regions where the ridges have been removed. These discrete regions span two or more adjacent teeth and form a shape, such as a circle, ellipse, square, octagon, etc.

According to an embodiment, an absorbent article can comprise a liquid pervious topsheet. The topsheet suitable for use herein can comprise wovens, non-wovens, apertured webs or not aperture webs, and/or three-dimensional webs of a liquid impermeable polymeric film comprising liquid permeable apertures. The topsheet may be a laminate. The topsheet may have more than one layer. The topsheet may comprise nonwoven fibers selecteted from the group consisting of meltblown, nanofibers, bicomponent fibers, and combinations thereof. The topsheet for use herein can be a single layer or may have a multiplicity of layers. For example, the wearer-facing and contacting surface can be provided by a film material having apertures which are provided to facilitate liquid transport from the wearer facing surface towards the absorbent structure. Such liquid permeable, apertured films are well known in the art. They provide a resilient three-dimensional fibre-like structure. Such films have been disclosed in detail for example in U.S. Pat. Nos. 3,929,135, 4,151,240, 4,319,868, 4,324,426, 4,343,314, 4,591,523, 4,609,518, 4,629,643, 4,695,422 or WO 96/00548.

The topsheet and/or the secondary topsheet may comprise a nonwoven material. The nonwoven materials of the present invention can be made of any suitable nonwoven materials ("precursor materials"). The nonwoven webs can be made from a single layer, or multiple layers (e.g., two or more layers). If multiple layers are used, they can be comprised of the same type of nonwoven material, or different types of nonwoven materials. In some cases, the precursor materials may be free of any film layers.

The fibers of the nonwoven precursor material(s) can be made of any suitable materials including, but not limited to natural materials, synthetic materials, and combinations thereof. Suitable natural materials include, but are not limited to cellulose, cotton linters, bagasse, wool fibers, silk fibers, etc. Cellulose fibers can be provided in any suitable form, including but not limited to individual fibers, fluff pulp, drylap, liner board, etc. Suitable synthetic materials include, but are not limited to nylon, rayon, and polymeric materials. Suitable polymeric materials include, but are not limited to: polyethylene (PE), polyester, polyethylene terephthalate (PET), polypropylene (PP), and co-polyester. Suitable synthetic fibers may have submicron diameters, thereby being nanofibers, such as Nufibers or be between 1 and 3 microns such as meltblown fibers or may be of larger diameter. In some embodiments, however, the nonwoven precursor materials can be either substantially, or completely free, of one or more of these materials. For example, in some embodiments, the precursor materials may be substantially free of cellulose, and/or exclude paper materials. In some embodiments, one or more precursor materials can comprise up to 100% thermoplastic fibers. The fibers in some cases may, therefore, be substantially non-absorbent. In some embodiments, the nonwoven precursor materials can be either substantially, or completely free, of tow fibers.

The precursor nonwoven materials can comprise any suitable types of fibers. Suitable types of fibers include, but are not limited to: monocomponent, bicomponent, and/or biconstituent, non-round (e.g., shaped fibers (including but not limited to fibers having a trilobal cross-section) and capillary channel fibers). The fibers can be of any suitable size. The fibers may, for example, have major cross-sectional dimensions (e.g., diameter for round fibers) ranging from 0.1-500 microns. Fiber size can also be expressed in denier, which is a unit of weight per length of fiber. The constituent fibers may, for example, range from about 0.1 denier to about 100 denier. The constituent fibers of the nonwoven precursor web(s) may also be a mixture of different fiber types, differing in such features as chemistry (e.g., PE and PP), components (mono- and bi-), shape (i.e. capillary channel and round) and the like.

The nonwoven precursor webs can be formed from many processes, such as, for example, air laying processes, wetlaid processes, meltblowing processes, spunbonding processes, and carding processes. The fibers in the webs can then be bonded via spunlacing processes, hydroentangling, calendar bonding, through-air bonding and resin bonding. The nonwoven precursor web or nonwoven web may be aperture with a process such as overbonding or pre-aperturing. Some of such individual nonwoven webs may have bond sites 46 where the fibers are bonded together.

In the case of spunbond webs, the web may have a thermal point bond 46 pattern that is not highly visible to the naked eye. For example, dense thermal point bond patterns are equally and uniformly spaced are typically not highly visible. After the material is processed through the mating male and female rolls, the thermal point bond pattern is still not highly visible. Alternatively, the web may have a thermal point bond pattern that is highly visible to the naked eye. For example, thermal point bonds that are arranged into a macro-pattern, such as a diamond pattern, are more visible to the naked eye. After the material is processed through the mating male and female rolls, the thermal point bond pattern is still highly visible and can provide a secondary visible texture element to the material.

The basis weight of nonwoven materials is usually expressed in grams per square meter (gsm). The basis weight of a single layer nonwoven material can range from about 8 gsm to about 100 gsm, depending on the ultimate use of the material 30. For example, the topsheet of a topsheet/acquisition layer laminate or composite may have a basis weight from about 8 to about 40 gsm, or from about 8 to about 30 gsm, or from about 8 to about 20 gsm. The acquisition layer may have a basis weight from about 10 to about 120 gsm, or from about 10 to about 100 gsm, or from about 10 to about 80 gsm. The basis weight of a multi-layer material is the combined basis weight of the constituent layers and any other added components. The basis weight of multi-layer materials of interest herein can range from about 20 gsm to about 150 gsm, depending on the ultimate use of the material 30. The nonwoven precursor webs may have a density that is between about 0.01 and about 0.4 g/cm$^3$ measured at 0.3 psi (2 KPa).

The precursor nonwoven webs may have certain desired characteristics. The precursor nonwoven web(s) each have a first surface, a second surface, and a thickness. The first and second surfaces of the precursor nonwoven web(s) may be generally planar. It is typically desirable for the precursor nonwoven web materials to have extensibility to enable the fibers to stretch and/or rearrange into the form of the protrusions. If the nonwoven webs are comprised of two or more layers, it may be desirable for all of the layers to be as extensible as possible. Extensibility is desirable in order to maintain at least some non-broken fibers in the sidewalls around the perimeter of the protrusions. It may be desirable for individual precursor webs, or at least one of the nonwovens within a multi-layer structure, to be capable of undergoing an apparent elongation (strain at the breaking force, where the breaking force is equal to the peak force) of greater than or equal to about one of the following amounts: 100% (that is double its unstretched length), 110%, 120%, or 130% up to about 200%. It is also desirable for the precursor nonwoven webs to be capable of undergoing plastic deformation to ensure that the structure of the deformations is "set" in place so that the nonwoven web will not tend to recover or return to its prior configuration.

Materials that are not extensible enough (e.g., inextensible PP) may form broken fibers around much of the perimeter of the deformation, and create more of a "hanging chad" (i.e., the cap of the protrusions may be at least partially broken from and separated from the rest of the protrusion. The area on the sides of the protrusion where the fibers are broken is designated with reference number.

When the fibers of a nonwoven web are not very extensible, it may be desirable for the nonwoven to be underbonded as opposed to optimally bonded. A thermally bonded nonwoven web's tensile properties can be modified by changing the bonding temperature. A web can be optimally or ideally bonded, underbonded, or overbonded. Optimally or ideally bonded webs are characterized by the highest breaking force and apparent elongation with a rapid decay in strength after reaching the breaking force. Under strain, bond sites fail and a small amount of fibers pull out of the bond site. Thus, in an optimally bonded nonwoven, the fibers 38 will stretch and break around the bond sites 46 when the nonwoven web is strained beyond a certain point. Often there is a small reduction in fiber diameter in the area surrounding the thermal point bond sites 46. Underbonded webs have a lower breaking force and apparent elongation when compared to optimally bonded webs, with a slow decay in strength after reaching the breaking force. Under strain, some fibers will pull out from the thermal point bond sites 46. Thus, in an underbonded nonwoven, at least some of the fibers 38 can be separated easily from the bond sites 46 to allow the fibers 38 to pull out of the bond sites and rearrange when the material is strained. Overbonded webs also have a lowered breaking force and elongation when compared to optimally bonded webs, with a rapid decay in strength after reaching the breaking force. The bond sites look like films and result in complete bond site failure under strain.

When the nonwoven web comprises two or more layers, the different layers can have the same properties, or any suitable differences in properties relative to each other. In one embodiment, the nonwoven web can comprise a two layer structure that is used in an absorbent article. For convenience, the precursor webs and the material into which they are formed will generally be referred to herein by the same reference numbers. As described above, one of the layers, a second layer, can serve as the topsheet of the absorbent article, and the first layer can be an underlying layer (or sub-layer) and serve as an acquisition layer. The acquisition layer receives liquids that pass through the topsheet and distributes them to underlying absorbent layers. In such a case, the topsheet may be less hydrophilic than sub-layer(s), which may lead to better dewatering of the topsheet. In other embodiments, the topsheet can be more hydrophilic than the sub-layer(s). In some cases, the pore size of the acquisition layer may be reduced, for example via using fibers with smaller denier or via increasing the density of the acquisition layer material, to better dewater the pores of the topsheet.

The second nonwoven layer that may serve as the topsheet can have any suitable properties. The second nonwoven layer may be absorbent. Properties of interest for the second nonwoven layer, when it serves as a topsheet, in addition to sufficient extensibility and plastic deformation may include uniformity and opacity. As used herein, "uniformity" refers to the macroscopic variability in basis weight of a nonwoven web. As used, herein, "opacity" of nonwoven webs is a measure of the impenetrability of visual light, and is used as visual determination of the relative fiber density on a macroscopic scale. As used herein, "opacity" of the different regions of a single nonwoven deformation is determined by taking a photomicrograph at 20× magnification of the portion of the nonwoven containing the deformation against a black background. Darker areas indicate relatively lower opacity (as well as lower basis weight and lower density) than white areas.

Several examples of nonwoven materials suitable for use as the second nonwoven layer 30B include, but are not limited to: spunbonded nonwovens; carded nonwovens; and other nonwovens with high extensibility (apparent elongation in the ranges set forth above) and sufficient plastic deformation to ensure the structure is set and does not have significant recovery. One suitable nonwoven material as a topsheet for a topsheet/acquisition layer composite structure may be an extensible spunbonded nonwoven comprising polypropylene and polyethylene. The fibers can comprise a blend of polypropylene and polyethylene, or they can be bi-component fibers, such as a sheath-core fiber with polyethylene on the sheath and polypropylene in the core of the fiber. Another suitable material is a bi-component fiber spunbonded nonwoven comprising fibers with a polyethylene sheath and a polyethylene/polypropylene blend core.

The first nonwoven layer that may, for example, serve as the acquisition layer can have any suitable properties. Properties of interest for the first nonwoven layer, in addition to sufficient extensibility and plastic deformation may include uniformity and opacity. If the first nonwoven layer serves as an acquisition layer, its fluid handling properties must also be appropriate for this purpose. Such properties may include: permeability, porosity, capillary pressure, caliper, as well as mechanical properties such as sufficient resistance to compression and resiliency to maintain void volume. Suitable nonwoven materials for the first nonwoven layer when it serves as an acquisition layer include, but are not limited to: spunbonded nonwovens; through-air bonded ("TAB") carded nonwoven materials; spunlace nonwovens; hydroentangled nonwovens; and, resin bonded carded nonwoven materials. Of course, the composite structure may be inverted and incorporated into an article in which the first layer serves as the topsheet and the second layer serves as an acquisition layer. In such cases, the properties and exemplary methods of the first and second layers described herein may be interchanged.

The layers of a two or more layered nonwoven web structure can be combined together in any suitable manner. In some cases, the layers can be unbonded to each other and held together autogenously (that is, by virtue of the formation of deformations therein). For example, both precursor webs 30A and 30B contribute fibers to deformations in a "nested" relationship that joins the two precursor webs together, forming a multi-layer web without the use or need for adhesives or thermal bonding between the layers. In other embodiments, the layers can be joined together by other mechanisms. If desired an adhesive between the layers, ultrasonic bonding, chemical bonding, resin or powder bonding, thermal bonding, or bonding at discrete sites using a combination of heat and pressure can be selectively utilized to bond certain regions or all of the precursor webs. In addition, the multiple layers may be bonded during processing, for example, by carding one layer of nonwoven onto a spunbond nonwoven and thermal point bonding the combined layers. In some cases, certain types of bonding between layers may be excluded. For example, the layers of the present structure may be non-hydroentangled together.

If adhesives are used, they can be applied in any suitable manner or pattern including, but not limited to: slots, spirals, spray, and curtain coating. Adhesives can be applied in any suitable amount or basis weight including, but not limited to between about 0.5 and about 30 gsm, alternatively between about 2 and about 5 gsm. Examples of adhesives could include hot melt adhesives, such as polyolefins and styrene block copolymers.

A certain level of adhesive may reduce the level of fuzz on the surface of the nonwoven material even though there may be a high percentage of broken fibers as a result of the deformation process. Glued dual-layer laminates produced as described herein are evaluated for fuzz. The method utilizes a Martindale Abrasion Tester, based upon ASTM D4966-98. After abrading the samples, they are graded on a scale of 1-10 based on the degree of fiber pilling (1=no fiber pills; 10=large quantity and size of fiber pills). The protrusions are oriented away from the abrader so the land area in between the depressions is the primary surface abraded. Even though the samples may have a significant amount of fiber breakage (greater than 25%, sometimes greater than 50%) in the side walls of the protrusions/depressions, the fuzz value may be low (around 2) for several different material combinations, as long as the layers do not delaminate during abrasion. Delamination is best prevented by glue basis weight, for example a glue basis weight greater than 3 gsm, and glue coverage.

When the precursor nonwoven web comprises two or more layers, it may be desirable for at least one of the layers to be continuous, such as in the form of a web that is unwound from a roll. In some embodiments, each of the layers can be continuous. In alternative embodiments, one or more of the layers can be continuous, and one or more of the layers can have a discrete length. The layers may also have different widths. For example, in making a combined topsheet and acquisition layer for an absorbent article, the nonwoven layer that will serve as the topsheet may be a continuous web, and the nonwoven layer that will serve as the acquisition layer may be fed into the manufacturing line in the form of discrete length (for example, rectangular, or other shaped) pieces that are placed on top of the continuous web. Such an acquisition layer may, for example, have a lesser width than the topsheet layer. The layers may be combined together as described above.

Nonwoven webs and materials are often incorporated into products, such as absorbent articles, at high manufacturing line speeds. Such manufacturing processes can apply compressive and shear forces on the nonwoven webs that may damage certain types of three-dimensional features that have been purposefully formed in such webs. In addition, in the event that the nonwoven material is incorporated into a product (such as a disposable diaper) that is made or packaged under compression, it becomes difficult to preserve the three-dimensional character of some types of prior three-dimensional features after the material is subjected to such compressive forces.

The nonwoven material can comprise a composite of two or more nonwoven materials that are joined together. In such a case, the fibers and properties of the first layer will be designated accordingly (e.g., the first layer is comprised of a first plurality of fibers), and the fibers and properties of the second and subsequent layers will be designated accordingly (e.g., the second layer is comprised of a second plurality of fibers). In a two or more layer structure, there are a number of possible configurations the layers may take following the formation of the deformations therein. These will often depend on the extensibility of the nonwoven materials used for the layers. It is desirable that at least one of the layers have deformations which form protrusions as described herein in which, along at least one cross-section, the width of the cap of the protrusions is greater than the width of the base opening of the deformations. For example, in a two layer structure where one of the layers will serve as the topsheet of an absorbent article and the other layer will serve as an underlying layer (such as an acquisition layer), the layer that has protrusions therein may comprise the topsheet layer. The layer that most typically has a bulbous shape will be the one which is in contact with the male forming member during the process of deforming the web.

The heterogeneous mass may be combined with the topsheet, a secondary topsheet, or the both using formation means. A group of fibers, or in fact, a portion of the whole topsheet is physically inserted into the heterogeneous mass so that within a single X-Y plane, a fiber from the topsheet, secondary topsheet, or both, is in direct contact with one or more fibers of the heterogeneous mass.

It has been surprisingly found that by placing a fibrous topsheet or a fibrous secondary topsheet, or both a fibrous topsheet and a secondary topsheet through a formation means process with a heterogeneous mass, one can create one or more "wells" instead of an aperture. Wells are distinguished from apertures and channels in that the outer surface of the wells includes one or more fibers from the group of fibers being integrated with the core without densifying the fibers that form the well. The "wells" may provide improved drainage of the topsheet through the secondary topsheet to the core comprising the heterogeneous mass. Use of wells may lead to various benefits including high fluid bridging between layers for reduced pooling of fluid at layer interfaces. Additionally, the "wells" may provide a higher capillarity work potential gradient to draw fluid away from topsheet and into the core compared to traditional absorbent articles, such as, for example, from 100 $mJ/m^2$ to 8000 $mJ/m^2$ within 0.5 mm, or 0.25 mm, or within 0.15 mm rather than current topsheets which have a gradient of 100 $mJ/m^2$ to 1000 $mJ/m^2$ over about 2 mm, or about 1.5 mm, or about 1 mm of distance. The capillarity work potential gradient may be between 500 $mJ/m^2$ and 7000 $mJ/m^2$ within 0.15 mm, such as, for example, between 1000 $mJ/m^2$ and 7000 $mJ/m^2$, between 1500 $mJ/m^2$ and 6500 $mJ/m^2$, between 2000 $mJ/m^2$ and 6000 $mJ/m^2$, between 2500 $mJ/m^2$ and 5000 $mJ/m^2$, such as, for example 500, 1000, 1500, 2000, 2500, 3000, 3500, 4000, 4500, 5000, 5500, 6000, 6500, 7000, 7500 $mJ/m^2$. Capillarity cascade relates to the change in capillarity as fluid moves from one layer to another layer within an absorbent structure. The thinner the materials are in each layer or the thinner the total thickness is through all layers, and the higher the difference in capillarity work potential between each layer, the higher the capillarity work potential gradient or capillarity cascade is within the absorbent structure. Traditional absorbent structures simply cannot achieve a capillarity work potential gradient across such a small distance in either the z-direction or within an x-y plane containing multiple layers of absorbent materials.

Without being bound by theory, it is believed that the integrated layers including a topsheet and/or a secondary topsheet with a heterogeneous mass that has a high capillary absorbent intertwined within the layer provides multiple surprising advantageous. Amongst these advantages may be, without limitation, 1. The ability to create bridging between the topsheet and the absorbent core for the purpose of absorbing complex liquids, 2. The ability to create a capillarity cascade within the topsheet to core system that allows form the moving of complex liquids into the high capillarity absorbent, 3. An absorbent system having an absorbent core and a topsheet that may conform to complex body shapes and dynamic movement, 4. An absorbent system having an absorbent core and a topsheet that has improved tactile feel.

Without being bound by theory, it is believed that the "wells" may provide improved drainage of the topsheet through the secondary topsheet to the core comprising the fibrous web. Specifically, the wells allow for improved drainage via the wells from the topsheet to the absorbent core when fluid is placed on the topsheet. The number of wells in an absorbent structure is set according to the pattern chosen during the formation means.

The wells are identified and can be seen within the same XY plane as the integrated layers. A group of fibers from the topsheet are integrated into the heterogeneous mass layer which comprises open cell foam. The group of fibers may be between 10 and 10,000 fibers per grouping, such as, for example, 10 fibers per grouping of fibers, 20 fibers per grouping of fibers, 30 fibers per grouping of fibers, 40 fibers per grouping of fibers, 50 fibers per grouping of fibers, 60 fibers per grouping of fibers, 70 fibers per grouping of fibers, 80 fibers per grouping of fibers, 90 fibers per grouping of fibers, 100 fibers per grouping, 400 fibers per grouping, 500 fibers per grouping, 1,000 fibers per grouping, 2,000 fibers per grouping, 3,000 fibers per grouping, 4,000 fibers per grouping, 5,000 fibers per grouping, 6,000 fibers per grouping, 7,000 fibers per grouping, 8,000 fibers per grouping, or 9,000 fibers per grouping. One or more grouping of fibers may be in direct contact. At least one of the grouping of fibers has a portion that is the external surface of a portion of a well.

A grouping of fibers may be inserted into the X-Y plane of both the STS and core such that it penetrates between 10% to 100% of the core layer, such as, 20%, 30%, 40%, 50%, 60%, 70%, 80%, or 90%. This is unlike traditional needlepunching that only places a few fibers down into a traditional core. Further, the group of fibers of the topsheet, or a group of fibers of the secondary topsheet and the fibers of the heterogeneous mass are in close proximity to each other within this X-Y plane, on the order of 0.01 mm to 0.5 mm distance, such as, for example 0.05 mm, 0.1 mm, 0.15 mm, 0.2 mm, 0.25 mm, 0.3 mm, 0.35 mm, 0.4 mm, or 0.45 mm.

The areas of the topsheet adjacent to the wells, the topsheet, Secondary topsheet, and core are in much closer or more intimate contact. Without being bound by theory, it is believed that the open cell foam may provide a resiliency or upward pressure against the topsheet. Traditional cores would likely disintegrate and/or would have no upward resiliency if they were placed through a similar formation means transformation process. Further, full foam layer cores would disintegrate and/or tear if placed through a similar process.

As previously discussed, the "wells" may provide a higher capillarity work potential gradient to draw fluid away from topsheet and into the core compared to traditional absorbent articles, such as, for example, from 100 mJ/m$^2$ to 80,000 mJ/m$^2$ within 0.5 mm, or 0.25 mm, or within 0.15 mm rather than current topsheets which have a gradient of 100 mJ/m$^2$ to 1000 mJ/m$^2$ over about 2 mm, or about 1.5 mm, or about 1 mm of distance. The absorbent core structure may exhibit a capillary cascade of between, for example, 100 mJ/m$^2$ to 80,000 mJ/m$^2$ within 0.5 mm; 1,000 mJ/m$^2$ to 70,000 mJ/m$^2$ within 0.5 mm; 3,000 mJ/m$^2$ to 70,000 mJ/m$^2$ within 0.5 mm; 5,000 mJ/m$^2$ to 60,000 mJ/m$^2$ within 0.5 mm; 10,000 mJ/m$^2$ to 50,000 mJ/m$^2$ within 0.5 mm; 20.000 mJ/m$^2$ to 40,000 mJ/m$^2$ within 0.5 mm; 100 mJ/m$^2$ to 80,000 mJ/m$^2$ within 0.25 mm; 1,000 mJ/m$^2$ to 70,000 mJ/m$^2$ within 0.25 mm; 3,000 mJ/m$^2$ to 70,000 mJ/m$^2$ within 0.25 mm; 5,000 mJ/m$^2$ to 60,000 mJ/m$^2$ within 0.25 mm; 10,000 mJ/m$^2$ to 50,000 mJ/m$^2$ within 0.25 mm; 20.000 mJ/m$^2$ to 40,000 mJ/m$^2$ within 0.25 mm; 100 mJ/m$^2$ to 80,000 mJ/m$^2$ within 0.15 mm; 1,000 mJ/m$^2$ to 70,000 mJ/m$^2$ within 0.15 mm; 3,000 mJ/m$^2$ to 70,000 mJ/m$^2$ within 0.15 mm; 5,000 mJ/m$^2$ to 60,000 mJ/m$^2$ within 0.15 mm; 10,000 mJ/m$^2$ to 50,000 mJ/m$^2$ within 0.15 mm; or 20.000 mJ/m$^2$ to 40,000 mJ/m$^2$ within 0.15 mm.

Additionally, the wells allow for the absorbent structure to exhibit a capillarity cascade along not only the vertical plane but also along the X-Y plane. Unlike other structures that may exhibit different capillarity profiles in the vertical direction versus within a plane, the absorbent structure having an integrated topsheet with a heterogeneous mass layer comprising wells creates a structure where the capillarity cascade is present within a plane. This is due to the integration of the groups of fibers from the topsheet through the heterogeneous mass.

The system absorbent structure having an integrated topsheet in a heterogeneous mass stratum provides surprising improvements in fluid acquisition. Specifically, the absorbent structure allows for a drier topsheet as measured via an NMR mouse method. The absorbent structure having an integrated topsheet, and/or integrated secondary topsheet, and heterogeneous mass exhibits a residual fluid left on a topsheet that is less than 1 ml/cm$^2$, such as for example, 0.75 ml/cm$^2$, 0.5 ml/cm$^2$, 0.4 ml/cm$^2$, 0.3 ml/cm$^2$, 0.2 ml/cm$^2$, or 0.1 ml/cm$^2$, as measured via the NMR mouse method. The absorbent structure having an integrated topsheet, and/or integrated secondary topsheet, and heterogeneous mass exhibits a residual fluid left in the top 1 mm of the absorbent article that is less than 1 ml/mm, such as for example, 0.75 ml/mm, 0.5 ml/mm, 0.4 ml/mm, 0.3 ml/mm, 0.2 ml/mm, or 0.1 ml/mm, as measured via the NMR Mouse method. Further, due to the use of wells in the integrated system, the system exhibits a negative slope of fluid removal from the topsheet as measured via the NMR Mouse method.

Further, fluid bridging is greatly enhanced via close integration of all three layers by a formation means. The resulting benefit is an ansorbent structure that is able to take in complex fluids at a rapid rate while providing an unmatched dryness. This is unlike previous fast topsheets, such as hydrophilically coated topsheets that may be fast but remain wet or have high-rewet values.

The integrated layer system may be quantified by the speed of moisture withdrawal from topsheet after fluid insult as measured by the NMR Mouse technique, the amount of residual moisture in the topsheet layer as measured by the NMR Mouse technique, or the rewet values of the pad as measured by the traditional rewet method.

The unique structure of this product can be measured by the amount of topsheet that is below or in-plane with the core as measured by NMR Mouse. The integrated absorbent structure may exhibit a residual fluid amount in the top 1 mm of the integrated topsheet core sample of less than 0.6 ml, such as, for example, between 0.0 ml and 0.5 ml, such as, less than 0.4 ml, less than 0.3 ml, less than 0.2 ml, or between 0 and 0.1 ml according to the NMR Mouse method.

Figure 27:
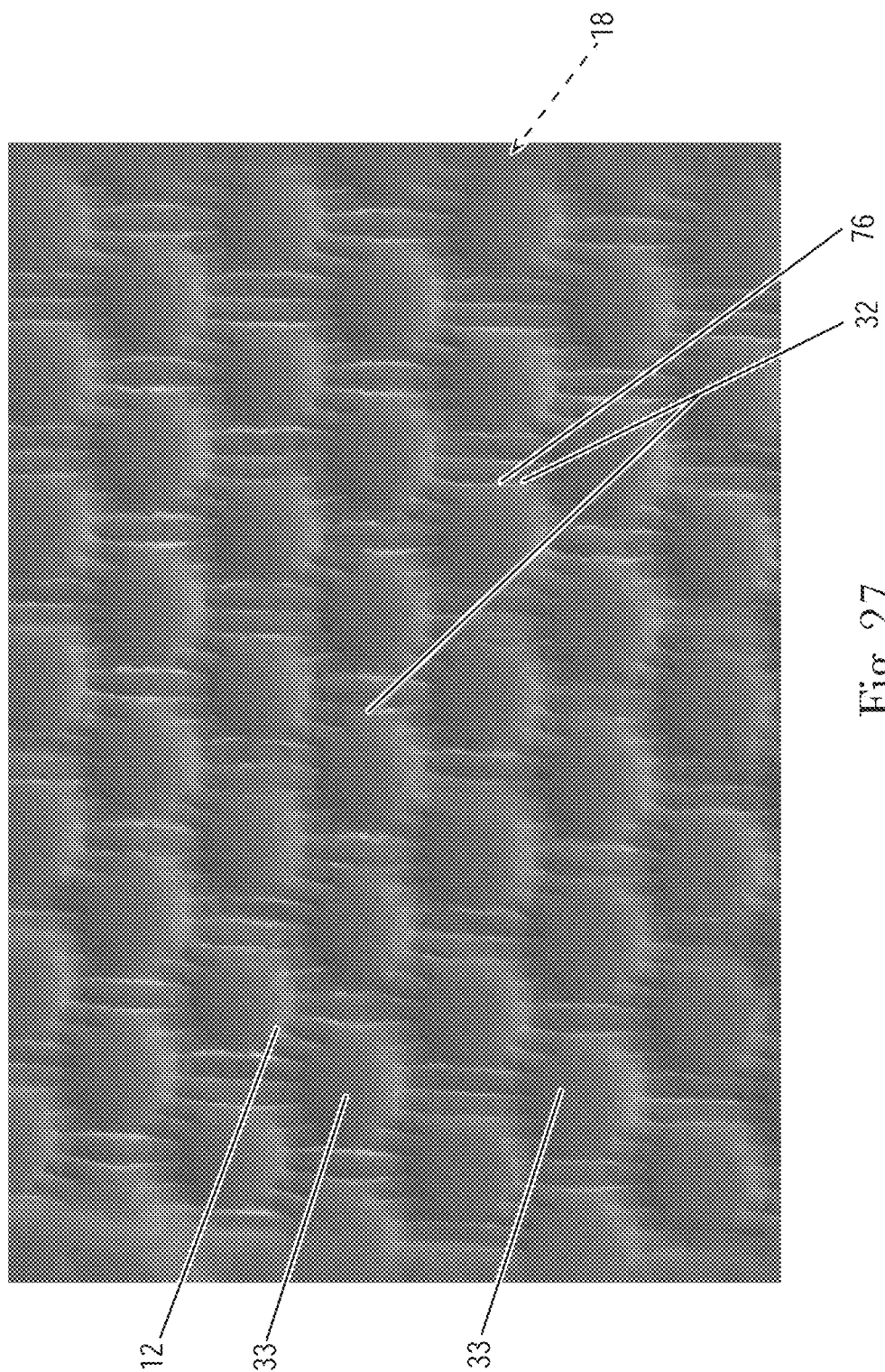
FIG. 27 is a top view of an alternative pattern.
Figure 28:
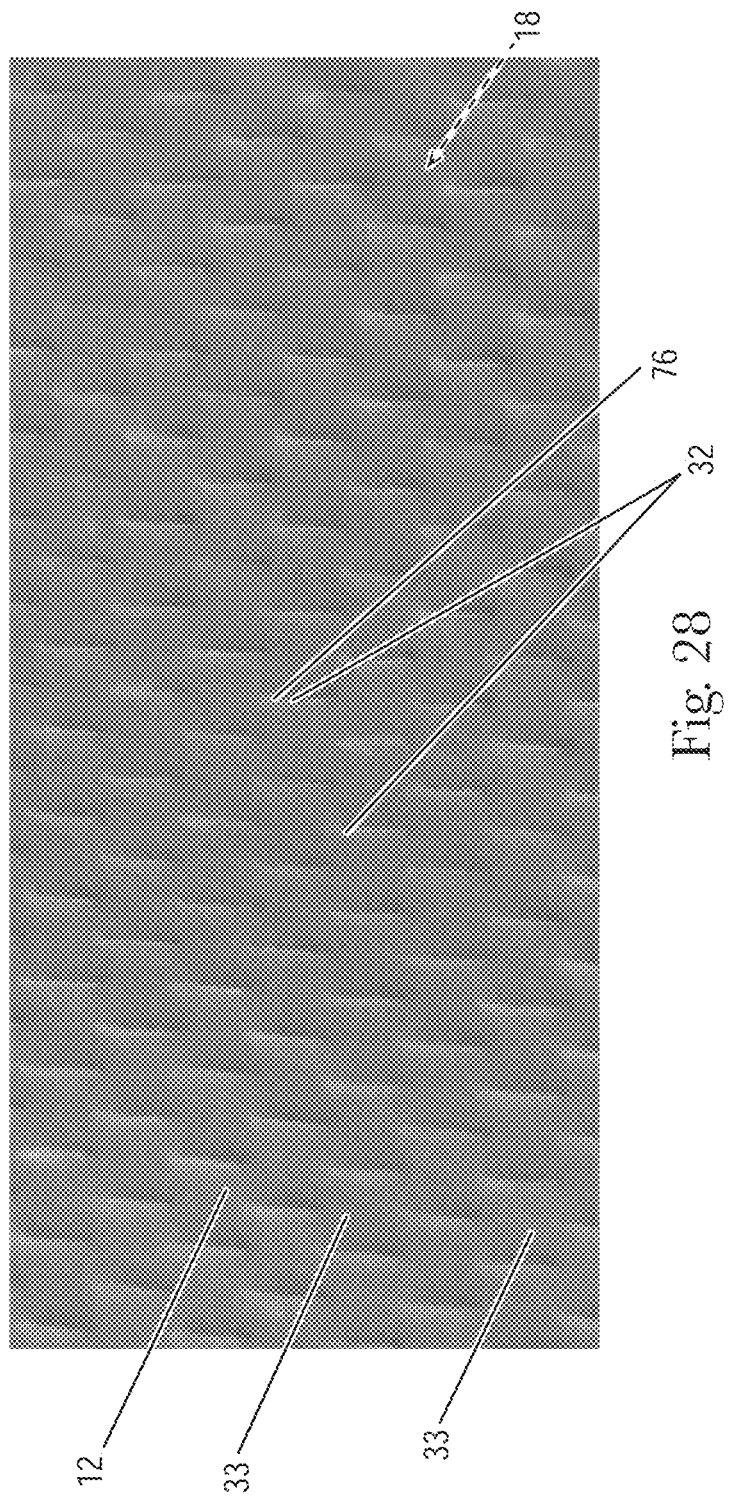
FIG. 28 shows a top view of alternative patterns.
Figure 29:
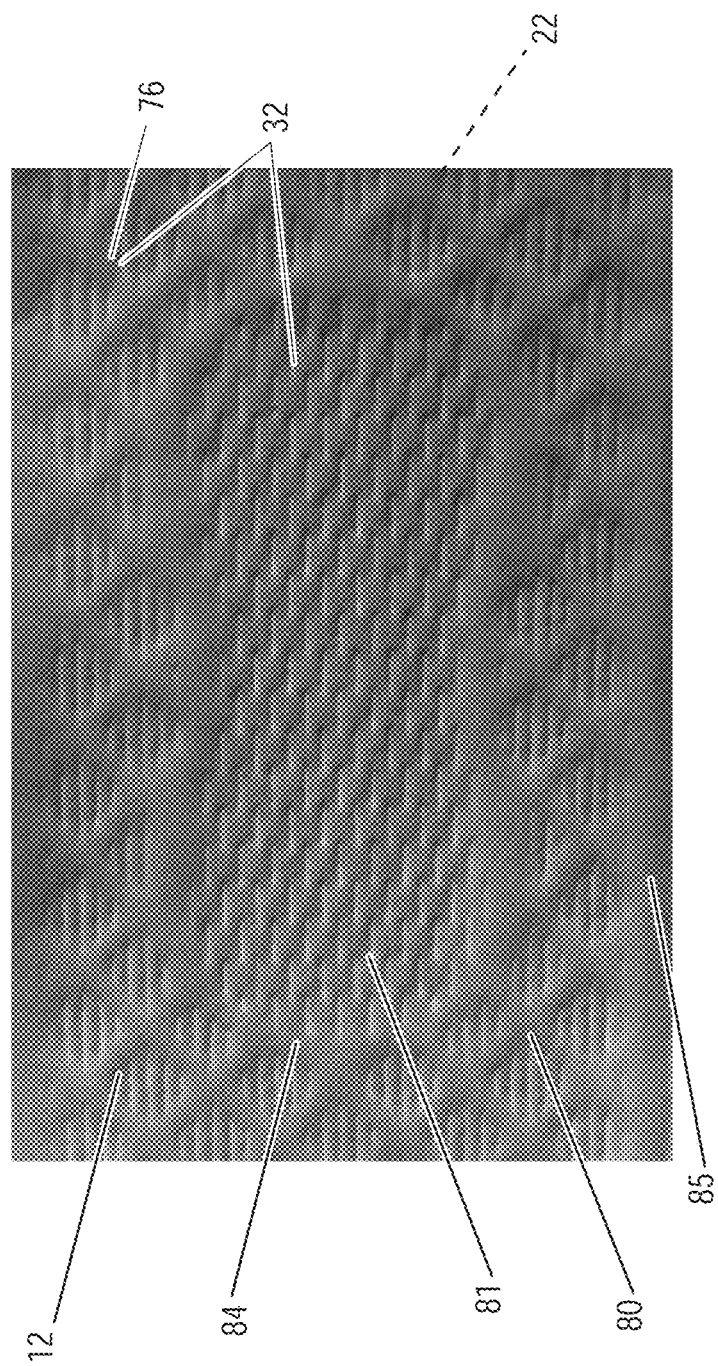
FIG. 29 shows a top view of alternative patterns.

As shown in FIGS. 27 to 29, a variety of patterns could be used. The patterns include zones. Zones are areas exhibiting one of either a visual pattern, a topography, an absorption rate or property, a bending parameter, a compression modulus, a resiliency, a stretch parameter or a combination thereof. The visual pattern may be any known geometric shape or pattern that is visual and can be conceived by the human mind. The topography may be any known pattern that is measurable and can be conceived by the human mind. Zones may be repeated or discrete. Zones may be orthogonal shapes and continuities that provide a visual appearance. The use of zones allows for tailoring of the fluid handling and mechanical properties of and within the pad. The integrated absorbent structure may have one or more visual patterns including zones along one of either the longitudinal or lateral axis of the integrated layers. The integrated layers may have two or more zones comprising one or more visual patterns. The two or more zones may be separated by a boundary. The boundary may be a topographical boundary, a mechanical boundary, a visual boundary, a fluid handling property boundary, or a combination thereof, provided that the boundary is not a densification of the absorbent core structure. The boundary property may be distinct from the two zones adjacent to the boundary. The absorbent structure may have a perimeter boundary that exhibits a different property than the one or more adjacent zones to the boundary.

It has also been surprisingly found that using formation means to integrate the topsheet, secondary topsheet, and the heterogeneous mass results in an improved flexibility of the pad (as measured by bunched compression. This is unlike traditional systems that become stiffer due to welding, glues, embossing, or when they improve capillarity through densification.

Further, by integrating a topsheet and/or a secondary topsheet with a fibrous web having high capillarity absorbents intertwined by either enrobement of the fibers or by using absorbent fibers, one can create an absorbent product that has a high degree of integration (as demonstrated by dryness of topsheet), low rewet due to strong capillarity close to the topsheet, and improved flexibility of the pad (as measured by the bunched compression test). This is unlike prior approaches to improve fluid bridging such as welding, gluing or needlepunching the topsheet to the Secondary Topsheet which often leads to a potential increase in the stiffness of the resulting product or a loss in flexibility of the combined layer versus the individual layers.

Further, the integrated topsheet and/or secondary topsheet with the heterogeneous mass delivers unique patterns that enable shaping dynamically without loss of structural integrity. The unique patterns may be leveraged such that they selectively deform some of the web enabling multiple bending modes for conforming to complex bodily shapes without meaningful degradation of the structural integrity of the absorbent product. Further, by designing the bending points in the absorbent product using formation means, one may create a product that has a better fit. The better fit is exemplified when the product is placed in contact with the spacing in the gluteal groove. Further, by enabling the product to have three dimensional topography, the absorbent product may bend and stretch to complex shapes and various surface topographies to be closer to the body of the user. Bending may be different for different sections.

The bunched compression method is a multi-axis bending test that is executed on product or core samples. When formation means is executed on a traditional layered core or a foam layer, in-use properties rapidly degrade or create product/core integrity issues. The ratio of the peak force to wet recovery energy communicates the balance between flexibility and shape stability of the product. The lower the peak force the more flexibility the product/material has when bending and conforming to her complex shape.

The absorbent structure may be deformed in the z direction with low compressive force while nevertheless preserving simultaneous the ability to conform and flow with complex bodily movements.

As discussed above, the topsheet and/or secondary topsheet integrated with a heterogeneous mass having a high capillarity absorbent has been found to impart curved, stretchable contours that can flow with the body without significant force to deform while not displacing her tissues aggressively. Further, the absorbent structure lacks strong densification, sharp tears, or shredding as seen with traditional cellulose based materials. Strong densification, sharp tears, and shredding may provide sharp contour which lead to a reduction in comfort and tactile softness. This property is exhibited using the Z-compressibility and the BC/Kawabata test methods.

Increased product flexibility may directly lead to improved comfort by the user. Increased flexibility allows for the product to follow the topography of the user's body and thereby may create better contact between the article and the body. Further, improved flexibility leads to a better usage experience because the product behaves more like a garment and may follow the contours of the body through dynamic motions. Another vector that improves overall comfort for the user is the level of cushion that the absorbent article may provide. Due to the direct contact with the body, increasing the cushion of the product and removing any rough surfaces leads to an improved tactile feel and comfort for the user.

A dynamic flexibility range and sustained product shape is given to the product by the specified ratio of peak to wet recovery of less than 150 gf/N*mm and greater than 30 gf/N*mm Conformance is also communicated to the user thru initial interaction with the pad the "cushiness" in caliper, stiffness and resiliency properties of the absorbent product in the thru thickness direction. In market products have demonstrated a consumer desirable stiffness gradient that signals a premium quality softness and product conformance in the product thru thickness direction. The quilted and/or pillowy nature of particular formation means patterns with the desireable stiffness gradient provide simultaneously a ZD direction cushiness that is desirable as well as active body cleaning locations that enhance the comfort experience in a way that the topography of traditional in market core systems cannot.

TABLE 1

Description of materials, material layers, integrated layers, suppliers, basis weight, caliper, capillarity work potential, and capillarity gradients.

| MATERIAL DESCRIPTIONS | Basis Weight (gsm) | Caliper (mm) | CWP (mJ/m^2) | Distance Topsheet to Absorbent Layer, mm | CWP Gradient (mJ/m^2)/mm |
|---|---|---|---|---|---|
| Prior Art 1 | | | | | |
| Always Ultra Market Product Composition: | N/A | N/A | N/A | N/A | N/A |
| Topsheet | 25 | 0.75 | 130 | | |
| Secondary Topsheet | 77 | 0.77 | 330 | 0.75 | 267 |
| Absorbent Core | 180 | 1.15 | 860 | 0.77 | 688 |
| Prior Art 2 | | | | | |
| Infinity Market Product Composition: | N/A | N/A | N/A | N/A | N/A |
| Topsheet | 28 | 0.38 | 115 | | |
| Foam Layer 1 | 188 | 1.5 | 1300 | 0.38 | 3118 |
| Foam Layer 2 | 188 | 0.6 | 7000 | 1.5 | 3800 |
| Inventions 3a, 3b, 3c, 4a, 4b, 4c | | | | | |
| Nonwoven Topsheet | 50 | 1.1 | 125 | | |
| Heterogenous Mass Stratum | 224 | 1.8 | 7870 | 0.5 | 15490 |
| | | | | 0.25 | 30980 |
| | | | | 0.15 | 51633 |

TABLE 1-continued

Description of materials, material layers, integrated layers, suppliers, basis weight, caliper, capillarity work potential, and capillarity gradients.

| MATERIAL DESCRIPTIONS | Basis Weight (gsm) | Caliper (mm) | CWP (mJ/ m^2) | Distance Topsheet to Absorbent Layer, mm | CWP Gradient (mJ/, ^2)/mm |
|---|---|---|---|---|---|
| Inventions 3d, 4d | | | | | |
| Nonwoven Topsheet BiCO | 28 | 0.38 | 115 | | |
| Heterogenous Mass Stratum | 224 | 1.8 | 7870 | 0.5 | 15510 |
| | | | | 0.25 | 31020 |
| | | | | 0.15 | 51700 |

As shown in Table 1, Prior Art 1 is an Always Ultra Market product, Prior Art 2 is an Always Infinity product, Inventions 3a, 3b, 3c, 4a, 4b, and 4c are a nonwoven topsheet with a heterogeneous mass stratum, and Inventions 3d and 4d are a nonwoven BiCo topsheet with a heterogeneous mass stratum. As shown by the data in Table 1, the combination of different material layers and the integration of those layers can be used to create a high capillarity work potential gradient across an absorbent structure, or said another way, an optimized capillarity cascade. For instance, a capillarity gradient between two layers within an Always Ultra pad can be determined by comparing the capillarity of the first layer, e.g. topsheet (130 mJ/m$^2$) and the capillarity of the second layer, e.g. STS (330 mJ/m$^2$), and then dividing the capillarity work potential by the distance the fluid must travel. In this case, the capillarity difference, 200 mJ/m$^2$ is divided by the distance between the two top surfaces (e.g. 0.75 mm distance), giving a capillarity gradient of about 267 mJ/m$^2$/mm. The distance between the top surface of the STS and the top surface of the core is 0.77 mm and the difference in capillarity work potential between the two materials is 530 mJ/m$^2$. Thus, the capillarity gradient between these two layers is about 688 mJ/m$^2$/mm. For a measure of the overall performance of an absorbent article, the difference between the capillarity work potential of the topsheet to the storage layer, or core, should be evaluated. For an Always Ultra pad, the capillarity of the storage layer or core is 860 mJ/m$^2$, so the capillarity difference between the topsheet and core is 730 mJ/m$^2$. The overall system has a total fluid travel distance of 1.52 mm and a capillarity work potential difference of 730 mJ/m$^2$, so the capillarity gradient of this absorbent system is about 480 mJ/m$^2$/mm.

With an absorbent product made with similar nonwoven topsheet (125 mJ/m$^2$ capillarity work potential, 1.1 mm caliper), no STS, and a heterogeneous mass core (7870 mJ/m$^2$) wherein both layers have been integrated through formation means or solid state formation, the capillarity gradient is significantly stronger because the distance between the two layers has also been significantly reduced via solid state formation. The actual distance the fluid has to travel from the top surface of the topsheet to the top of the heterogeneous mass core has been reduced to between 0.15 mm and 0.5 mm. If the distance the fluid has to travel is reduced to 0.5 mm, the capillarity gradient is now 15490 mJ/m$^2$/mm. In the situation where surface wells as previously described have been formed by solid state formation, the distance between the topsheet and core may be as less than or equal to 0.25 mm, and the fluid can travel in either the Z direction or within multiple X-Y planes due to the topsheet and heterogeneous mass layer being closely integrated within the wells. In this case, the capillarity gradient may be as high as 30,980 mJ/m$^2$/mm.

Therefore, one embodiment of the present invention is an absorbent product having a capillarity gradient between the topsheet and storage layer that may be greater than 8,000 mJ/m$^2$/mm, such as for example, between 8,000 mJ/m$^2$/mm and 60,000 mJ/m$^2$/mm, such as for example, 14,000 mJ/m$^2$/mm, or 20,000 mJ/m$^2$/mm, or 28,000 mJ/m$^2$/mm, or 36,000 mJ/m$^2$/mm, or 50,000 mJ/m$^2$/mm, or 60,000 mJ/m$^2$/mm.

Table 2A and 2B. Examples from combining different materials, cores, topsheet integration, types of integration and resulting mechanical characteristics.

TABLE 2A

| | | Bunched Compression | | | |
|---|---|---|---|---|---|
| Examples | Topsheet Integration? | 1st Cycle Dry Peak Force, gf | Wet Recovery Energy 5th Cycle, N · mm | Ratio Dry Peak Over Wet Energy | |
| Prior Art 1 | None | 200 | 1.2 | 167 | |
| Prior Art 2 | None | 121 | 2.6 | 47 | |
| Invention 3a | None | 350 | 3.5 | 100 | |
| Invention 3b | RIPS-DB1 | 257 | 1.9 | 135 | |
| Invention 3c | Jellyfish | 171 | 1.94 | 88 | |
| Invention 3d | Diamond | 319 | 1.8 | 177 | |
| Invention 4a | None | 98 | 2.2 | 45 | |
| Invention 4b | RIPS-DB1 | 74 | 1.5 | 49 | |
| Invention 4c | Jellyfish | 75 | 1.4 | 54 | |
| Invention 4d | Diamond | 78 | 1.0 | 78 | |

TABLE 2B

| | | Z-Compression Slope (Newton/mm)@ Percent Compression of Initial Caliper | | | | | |
|---|---|---|---|---|---|---|---|
| Examples | Kawabata Testing Kawabata Dry, MD (gf * cm^2/cm) | 13% | 25% | 38% | 50% | Resiliency | Compressive Energy (N · mm) |
| Prior Art 1 | 1.74 | 2.04 | 5.04 | 14.63 | 71.26 | 77% | 21.0 |
| Prior Art 2 | 10.65 | 5.49 | 9.30 | 9.78 | 17.82 | 40% | 16.8 |
| Invention 3a | 11.65 | 4.30 | 7.57 | 13.82 | 20.18 | 40% | 25.2 |

TABLE 2B-continued

| Examples | Kawabata Testing Kawabata Dry, MD (gf * cm^2/cm) | Z-Compression Slope (Newton/mm)@ Percent Compression of Initial Caliper | | | | | Compressive Energy (N · mm) |
| --- | --- | --- | --- | --- | --- | --- | --- |
| | | 13% | 25% | 38% | 50% | Resiliency | |
| Invention 3b | 3.82 | 5.29 | 10.03 | 13.25 | 17.32 | 40% | 13.0 |
| Invention 3c | 1.49 | 5.28 | 14.07 | 25.96 | 45.09 | 43% | 22.2 |
| Invention 3d | 2.77 | 6.29 | 10.44 | 13.11 | 18.42 | 40% | 20.5 |
| Invention 4a | 6.55 | 4.30 | 7.57 | 13.82 | 20.18 | 40% | 25.2 |
| Invention 4b | 2.92 | 5.29 | 10.03 | 13.25 | 17.32 | 40% | 13.0 |
| Invention 4c | 1.88 | 5.28 | 14.07 | 25.96 | 45.09 | 43% | 22.2 |
| Invention 4d | 2.43 | 6.29 | 10.44 | 13.11 | 18.42 | 40% | 20.5 |

Tables 2A and 2B combined show separates mechanical characteristics into three distinct groups. The invention samples are integrated. The Bunch Compression data is important to the consumer because a product that is too stiff when dry will be uncomfortable to wear as it will tend to chafe the inner thigh during movement. Further, a product that tends to disintegrate after becoming wet or soiled will also be uncomfortable to wear as it will tend to remain bunched and not provide good coverage of the panty. Therefore, an optimized product should have a $1^{st}$ cycle Dry Peak Force compression of between about 30 and 100 gf and a Wet Recovery energy of between about 1 and 2 N*mm.

Kawabata drape testing is a common industrial standard method for measuring the ability of a material to bend. Given the complex geometry of the intimate area, it has been found that a desirable dry bending measurement according to this method is between 2 and 10.5 (gf*cm$^2$)/cm as measured in either the MD or CD direction. A desirable wet bending measurement is between 1.25 and 10 (gf*cm$^2$)/cm as measured in either the MD or CD direction when 0.5 mls of 0.9% saline solution is slowly added to the sample over a 5 minute period and the product tested on the Kawabata instrument after a further 2 minute waiting period. Referring to the previous discussion about the desire for the product to not disintegrate when wet, it is desirable that the wet bending measurement according to the Kawabata drape testing when ran for a wet sample should drop less than about 50% of the measurement for the same sample when dry, such as, for example, less than about 40%, less than 30%, less than 20%, or less than about 10%.

Without being bound by theory, it is understood that compression recovery is also important to consumers. Consumers want the product to remain in contact with their intimate area without exerting a noticeable or unpleasant pressure against the skin. It has been found that there is an optimum compressive energy of between about 10 and 20 N*mm. It is also desirable to have a resiliency of between 20 and 50%. Further, it is desirable to have a compression profile that has a force of (N*mm) at different percentages of compression that falls within the following ranges:

| % Compression of product thickness | N/mm optimal range |
| --- | --- |
| 1-13 | 2.5 to 6 |
| 13-25 | 7 to 14 |
| 25-38 | 10 to 26 |
| 38-50 | 17 to 45 |

It has been surprisingly found that by having a percent compression of product thickness exhibiting the N/mm optimal ranges from above, one can create a product that has a smooth compression profile during dynamic bodily movements.

The surprising value of these measurements is in identifying unique new structures and products which have an optimized bunch compression in both the dry and wet states over multiple cycles of movement, an ability to conform to tight bending radii without creasing or breaking, and to provide a moderate level of resiliency so as to be invisible to the consumer while she is wearing the product.

In one embodiment, an absorbent article has a dry bending measurement according to the Kawabata method of between 2 and 10.5 (gf*cm$^2$)/cm as measured in either the MD or CD direction or a wet bending measurement between 1.25 and 10 (gf*cm$^2$)/cm as measured in either the MD or CD direction, and in addition, optionally, one or more of any of the following; a $1^{st}$ cycle Dry Peak Force compression of between about 30 and 150 gf, a Wet Recovery energy of between about 1 and 2 N/mm, a compressive energy of between about 10 and 20 N/mm, a resiliency of between 20 and 50%, or a speed of recovery as measured by the Z-Compressive slope (N/mm) at 1-13% of between 2 and 6 N/mm, at 13-25% of between 7 and 14 N/mm, at 25-38% of between 10 and 26 N/mm, or at 38-50% of between 17 and 45 N/mm.

In one embodiment, an absorbent article has a speed of recovery as measured by the Z-Compressive slope (N/mm) at 1-13% of between 2 and 6 N/mm, at 13-25% of between 7 and 14 N/mm, at 25-38% of between 10 and 26 N/mm, or at 38-50% of between 17 and 45 N/mm, and in addition, optionally, one or more of any of the following; a $1^{st}$ cycle Dry Peak Force compression of between about 30 and 150 gf, a Wet Recovery energy of between about 1 and 2 N/mm, a compressive energy of between about 10 and 20 N/mm, a resiliency of between 20 and 50%, or a dry bending measurement according to the Kawabata method of between 2 and 10.5 (gf*cm$^2$)/cm as measured in either the MD or CD direction or a wet bending measurement between 1.25 and 10 (gf*cm$^2$)/cm as measured in either the MD or CD direction.

TABLE 3

Examples from combining different materials, cores, topsheet integration, types of integration and resulting fluid handling characteristics.

| | | FLUID Handling Testing | | | | | |
|---|---|---|---|---|---|---|---|
| Absorbent Material/System | Topsheet Integration? | Blot, Total Residual, mg | NMR-Residual ml/mm | NMR-K-Profile (% decay @60 sec) | NMR-K-Profile (% decay @100 sec) | NMR-K-Profile (% decay @300 sec) | LiTS (g) |
| Prior Art 1 | None | 80 | 1.25 | 0 | 8 | 12 | 0.32 |
| Prior Art 2 | None | 22 | 0.3 | 30 | 69 | 90 | 0.05 |
| Invention 3a | None | 52 | 0.57 | 2 | 13 | 60 | 0.22 |
| Invention 3b | RIPS-DB1 | 21 | 0.33 | 85 | 87 | 89 | 0.05 |
| Invention 3c | Jellyfish | 18 | 0.29 | 87 | 90 | 93 | 0.04 |
| Invention 3d | Diamond | 16 | 0.25 | 90 | 94 | 95 | 0.04 |
| Invention 4a | None | 52 | 0.57 | 2 | 13 | 60 | 0.22 |
| Invention 4b | RIPS-DB1 | 21 | 0.33 | 85 | 87 | 89 | 0.05 |
| Invention 4c | Jellyfish | 18 | 0.29 | 87 | 90 | 93 | 0.04 |
| Invention 4d | Diamond | 16 | 0.25 | 90 | 94 | 95 | 0.04 |

Table 3 indicates the ability of the new absorbent structure to quickly dry the topsheet relative to current commercial products as measured by the Mouse NMR K-Profile at 60 seconds, 100 seconds, or 300 seconds. The Mouse NMR method for residual fluid measures the ability of the new absorbent structure to efficiently wick fluid away from the topsheet within the top millimeter of the topsheet. The LiTS method measures residual fluid within the topsheet. The Blot test assesses the competition for fluid between a skin analog and the absorbent product.

In one embodiment, as measured by the Mouse NMR K-Profile method, the new absorbent article is able to remove more than 90% of the fluid within 300 seconds after insult, more than 70% of the fluid within 100 seconds after insult, and more than 30% of the fluid within 60 seconds after insult, and in addition, optionally, one or more of any of the following; the ability to reduce the level of fluid remaining on the skin analog to a level below 20 mg as measured by the Blot test, the ability to reduce the residual fluid in the top 1 mm of the absorbent article to below 0.30 ml/mm as measured by the Mouse NMR method for residual fluid, or the ability to reduce the residual fluid in a topsheet to a value of 0.04 g or less using the LiTS method for measuring residual fluid.

In one embodiment, the new absorbent structure is able to reduce the level of fluid remaining on the skin analog to a level below 20 mg as measured by the Blot test, and in addition, optionally, one or more of any of the following; the ability to remove more than 90% of the fluid within 300 seconds after insult, more than 70% of the fluid within 100 seconds after insult, and more than 30% of the fluid within 60 seconds after insult as measured by the Mouse NMR K-Profile method or the ability to reduce the residual fluid in the top 1 mm of the absorbent article to below 0.30 ml/mm as measured by the Mouse NMR method for residual fluid.

In one embodiment, the new absorbent structure is able to reduce the residual fluid in the top 1 mm of the absorbent article to below 0.30 ml/mm as measured by the Mouse NMR method for residual fluid, and in addition, optionally, one or more of any of the following; the ability to remove more than 90% of the fluid within 300 seconds after insult, more than 70% of the fluid within 100 seconds after insult, and more than 30% of the fluid within 60 seconds after insult as measured by the Mouse NMR K-Profile method or the ability to reduce the level of fluid remaining on the skin analog to a level below 20 mg as measured by the Blot test.

In one embodiment, the new absorbent structure is able to reduce the residual fluid in a topsheet to a value of 0.04 g or less using the LiTS method for measuring residual fluid.

Improving mechanical properties of the absorbent product, such as its ability to conform to complex geometries via improved bending properties, optimized bunch compression and resiliency properties, and Z-compression has the potential to negatively affect fluid handling properties. For instance, as the absorbent article conforms to the body better, the body exudates no longer contact the absorbent article over a broad area. Rather, the body exudates are more likely to contact the topsheet of the absorbent article on a smaller portion of the topsheet. This results in a need for the absorbent article to also have an improved ability to transport larger amounts of fluid down and away from the point of fluid contact with the absorbent article. Not addressing this need will leave the consumer feeling wet longer and dissatisfied with the product performance even though the product fits better and is more comfortable to wear. Therefore, there is a need to provide an absorbent article with improved fluid handling properties in combination with improvement of mechanical properties. The improved absorbent article disclosed herein addresses both of those needs via the following combinations.

In one embodiment, the new absorbent article has a dry bending measurement between 2 and 10.5 gf*cm$^2$/cm or a wet bending measurement between 1.25 and 10 gf*cm2/cm according to the Kawabata method measured in either the MD or CD direction, and is able to remove more than 90% of the fluid within 300 seconds after insult, more than 60% of the fluid within 100 seconds after insult, or more than 30% of the fluid within 60 seconds after insult according to the NMR K-Profile test method.

In one embodiment, the new absorbent article has a dry bending measurement between 2 and 10.5 gf*cm$^2$/cm or a wet bending measurement between 1.25 and 10 gf*cm2/cm according to the Kawabata method measured in either the MC or CD direction, and is able to reduce the fluid remaining on the skin analog to below 20 mg, below 40 mg, or below 60 mg as measured by the Blot test.

In one embodiment, the new absorbent article is able to remove more than 90% of the fluid within 300 seconds after insult, more than 60% of the fluid within 100 seconds after insult, or more than 30% of the fluid within 60 seconds after insult and has a bunch compression ratio of $1^{st}$ cycle dry peak force (gf) over $5^{th}$ cycle wet recovery energy (N*mm) of between 45 and 135 gf/N*mm.

In one embodiment, the new absorbent article has a bunch compression ratio of $1^{st}$ cycle dry peak force (gf) over 5th cycle wet recovery energy (N*mm) of between 45 and 135 gf/N*mm and is able to reduce the fluid remaining on the skin analog to below 20 mg, below 40 mg, or below 60 mg as measured by the Blot test.

Further, by utilizing repeating patterns of bending models on a meso-scale versus historical macro scale that are bendable and shapeable based on each user's unique anatomical shape and how the user deforms the absorbent system while wearing, it has been found that one can create an absorbent structure that is able to have improved contact between the absorbent product and the user.

As used herein, meso-scale relates to a mechanical transformation that displaces larger more infrequent modifications to the absorbent article. For instance, traditional absorbent articles may have two to seven zones involving structures or mechanical transformations. In this context, meso-scale refers to a mechanical transformation that involves 10-70 mechanical transformations within the absorbent article. For instance, traditional hot pin aperturing or needle punching involves 1 to 10 fibers whereas a meso-scale mechanical transformation may involve greater than 10 and up to 100 fibers or more. In another example, an absorbent article may have one to five bending moments across the width or length of the absorbent article. In contrast, a meso-scale mechanical transformation may involve 5 to 50 transformations.

Without being bound by theory, applicants have found that it is desireable to create a repeating pattern of bending modes delivered by formation means that is significantly more that has ever been offered before and to do this without compromising resiliency or imparting discomfort. This improved bending is exemplified using the BC, Kawabata test method plus the z-compression method. The Increased dynamic body conformance promotes a panty-like fit experience. Further, without being bound by theory, it is believed that the proposed method and combination of selective materials may lead to the creation of pillow-like 3D topography creates structures that have a low initial stiffness gradient in the first 50% of compression as this compression increases the stiffness gradient becomes stiffer becoming equivalent or slightly greater than the base structure due to the pre-compression built in to the structure by topsheet integration. The low initial stiffness gradient promotes the feeling of an airy soft feeling signaling comfort to her.

Textured surface and increased stiffness gradient (when compressed) aides in active cleaning of her body with an additional frictional component known as "plowing friction". Locally skin/fat deforms down into the undulations of the pad surface as her body and pad form an interface and pressure is created. Pad and body move relative to one another fluid is wiped away by the pad and quickly wicked away from her body by the highly absorbent TS/core assembly. Active or dynamic cleaning of her body gives her a clean, dry and fresh feeling.

The absorbent core structure may be attached to the topsheet, the backsheet, or both the topsheet and backsheet using bonds, a bonding layer, adhesives, or combinations thereof. Adhesives may be placed in any suitable pattern, such as, for example, lines, spirals, points, circles, squares, or any other suitable pattern. Bonds may be placed in any suitable pattern, such as, for example, lines, spirals, points, circles, squares, or any other suitable pattern.

The absorbent layers may be combined using an intermediate layer between the two layers. The intermediate layer may comprise a tissue, a nonwoven, a film, or combinations thereof. The intermediate layer may have a permeability greater than the 200 Darcy.

Figure 12:
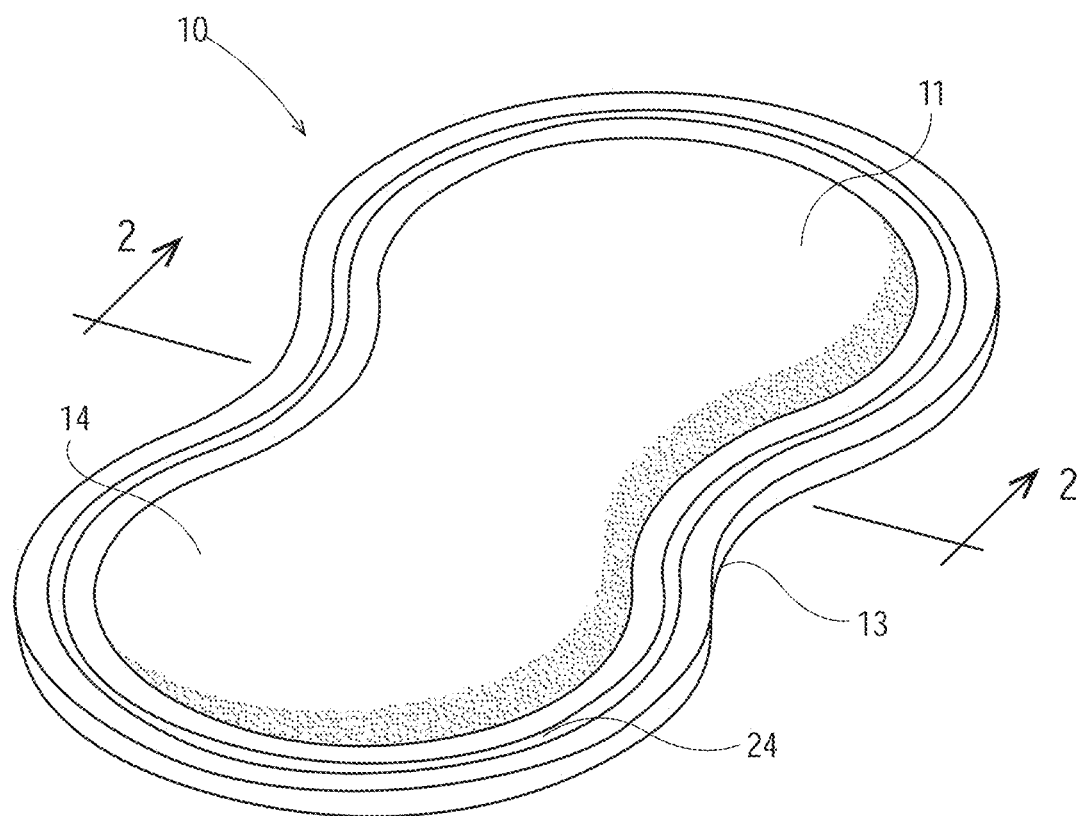
FIG. 12 is a perspective view of one embodiment of a sanitary napkin.

FIG. 12 a perspective view of one embodiment of a sanitary napkin. The illustrated sanitary napkin 10 has a body-facing upper side 11 that contacts the user's body during use. The opposite, garment-facing lower side 13 contacts the user's clothing during use.

A sanitary napkin 10 can have any shape known in the art for feminine hygiene articles, including the generally symmetric "hourglass" shape as shown in FIG. 12, as well as pear shapes, bicycle-seat shapes, trapezoidal shapes, wedge shapes or other shapes that have one end wider than the other. Sanitary napkins and pantyliners can also be provided with lateral extensions known in the art as "flaps" or "wings". Such extensions can serve a number of purposes, including, but not limited to, protecting the wearer's panties from soiling and keeping the sanitary napkin secured in place.

The upper side of a sanitary napkin generally has a liquid pervious topsheet 14. The lower side generally has a liquid impervious backsheet 16 that is joined with the topsheet 14 at the edges of the product. An absorbent core 18 is positioned between the topsheet 14 and the backsheet 16. A secondary topsheet may be provided at the top of the absorbent core 18, beneath the topsheet.

The topsheet 12, the backsheet 16, and the absorbent core 18 can be assembled in a variety of well-known configurations, including so called "tube" products or side flap products, such as, for example, configurations are described generally in U.S. Pat. No. 4,950,264, "Thin, Flexible Sanitary Napkin" issued to Osborn on Aug. 21, 1990, U.S. Pat. No. 4,425,130, "Compound Sanitary Napkin" issued to DesMarais on Jan. 10, 1984; U.S. Pat. No. 4,321,924, "Bordered Disposable Absorbent Article" issued to Ahr on Mar. 30, 1982; U.S. Pat. No. 4,589,876, and "Shaped Sanitary Napkin With Flaps" issued to Van Tilburg on Aug. 18, 1987. Each of these patents is incorporated herein by reference.

The backsheet 16 and the topsheet 14 can be secured together in a variety of ways. Adhesives manufactured by H. B. Fuller Company of St. Paul, Minn. under the designation HL-1258 or H-2031 have been found to be satisfactory. Alternatively, the topsheet 14 and the backsheet 16 can be joined to each other by heat bonding, pressure bonding, ultrasonic bonding, dynamic mechanical bonding, or a crimp seal. A fluid impermeable crimp seal 24 can resist lateral migration ("wicking") of fluid through the edges of the product, inhibiting side soiling of the wearer's undergarments.

As is typical for sanitary napkins and the like, the sanitary napkin 10 of the present invention can have panty-fastening adhesive disposed on the garment-facing side of backsheet 16. The panty-fastening adhesive can be any of known adhesives used in the art for this purpose, and can be covered prior to use by a release paper, as is well known in the art. If flaps or wings are present, panty fastening adhesive can be applied to the garment facing side so as to contact and adhere to the underside of the wearer's panties.

The backsheet may be used to prevent the fluids absorbed and contained in the absorbent structure from wetting materials that contact the absorbent article such as underpants, pants, pyjamas, undergarments, and shirts or jackets, thereby acting as a barrier to fluid transport. The backsheet according to an embodiment of the present invention can also allow the transfer of at least water vapour, or both water vapour and air through it.

Especially when the absorbent article finds utility as a sanitary napkin or panty liner, the absorbent article can be also provided with a panty fastening means, which provides means to attach the article to an undergarment, for example a panty fastening adhesive on the garment facing surface of the backsheet. Wings or side flaps meant to fold around the crotch edge of an undergarment can be also provided on the side edges of the napkin.

Figure 13:
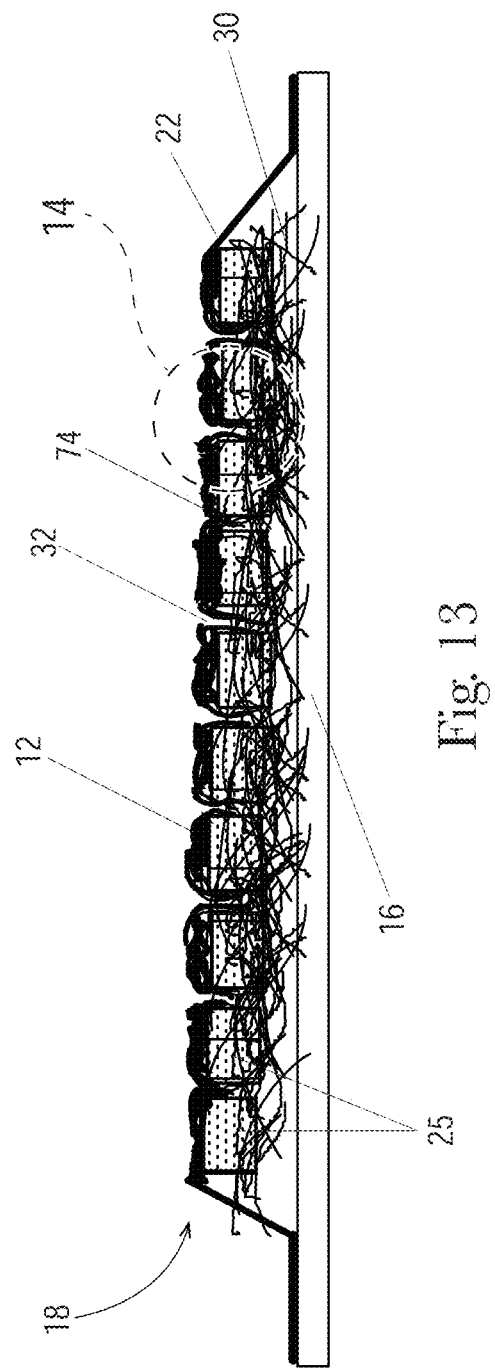
FIG. 13 is a cross-sectional view of the sanitary napkin of FIG. 1, taken through line 2-2.

FIG. 13 is a cross-sectional view of the sanitary napkin 10 of FIG. 12, taken through line 2-2. As shown in the figure, the absorbent core 18 structure comprises of a heterogeneous mass 22 comprising open-cell foam pieces 25. The topsheet is integrated into the heterogeneous mass 22 forming wells 32.

Figure 14:
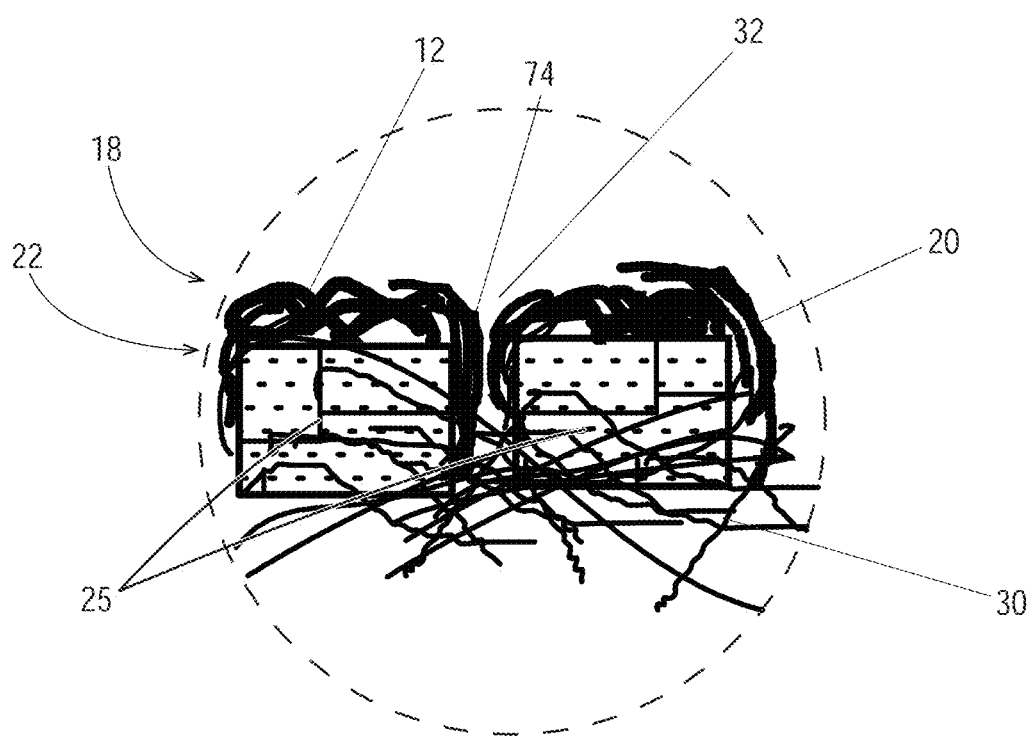
FIG. 14 is an enlarged section of FIG. 13.

FIG. 14 is a zoomed in version of a portion of FIG. 13. As shown in FIG. 14, The topsheet 12 is incorporated into the absorbent core 18 comprising a heterogeneous mass 22 stratum. The heterogeneous mass 22 has open cell foam pieces 25. A well is 32 is shown between the open cell foam pieces 25. A group of fibers 74 is in the same X-Y plane as the heterogeneous mass 22 layer. from the topsheet 12

Figure 15:
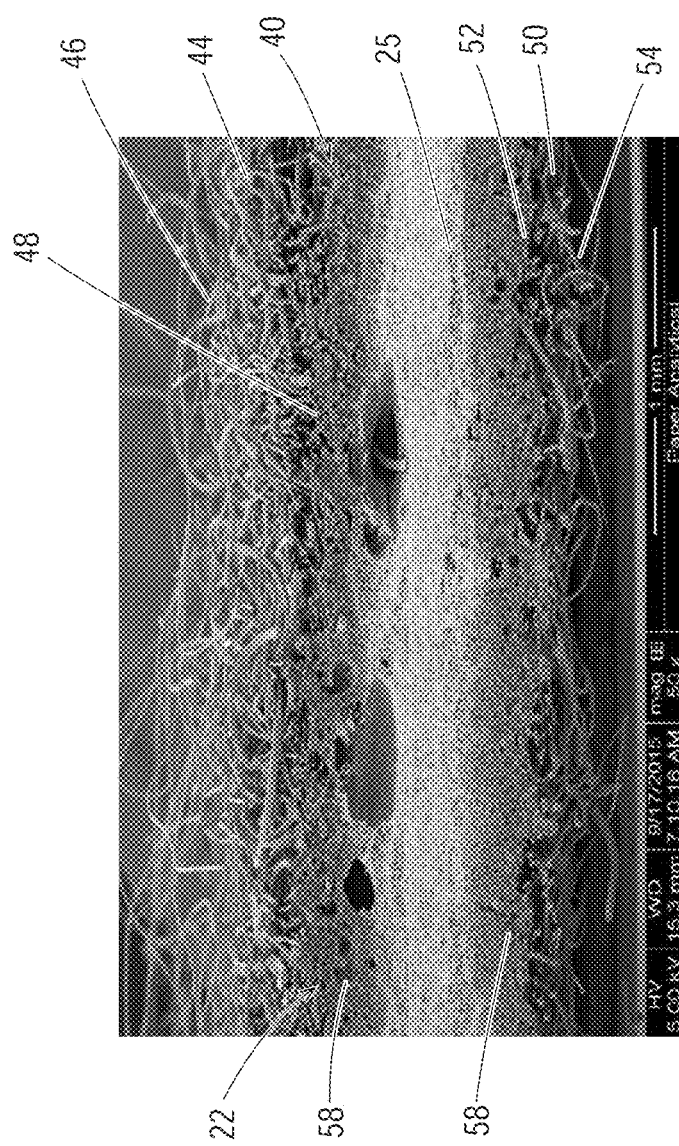
FIG. 15 is an SEM micrograph of a heterogeneous mass.

FIG. 15 is an SEM micrograph of a heterogeneous mass 22 prior to any formation means or forming of canals. As shown in FIG. 15, the absorbent stratum 40 is a heterogeneous mass 22 comprising a first planar nonwoven 44 having a first surface 46 and a second surface 48 and a second planar nonwoven 50 having a first surface 52 and a second surface 54. An open cell foam piece 25 enrobes a portion of the first planar nonwoven 44 and a portion of the second planar nonwoven 50. Specifically, the open cell foam piece 25 enrobes enrobeable elements 58 in both the second surface 48 of the first planar nonwoven 44 and the first surface 52 of the second planar nonwoven 50.

Figure 16:
FIG. 16 is an SEM micrograph of a heterogeneous mass.

FIG. 16 is an SEM micrograph of a heterogeneous mass 22 after formation means. As shown in FIG. 16, the absorbent stratum 40 is a heterogeneous mass 22 comprising a first planar nonwoven 44 having a first surface 46 and a second surface 48 and a second planar nonwoven 50 having a first surface 52 and a second surface 54. An open cell foam piece 25 enrobes a portion of the first planar nonwoven 44 and a portion of the second planar nonwoven 50. The planar nowovens are shown as wavy due to the impact of the formation means.

Figure 17:
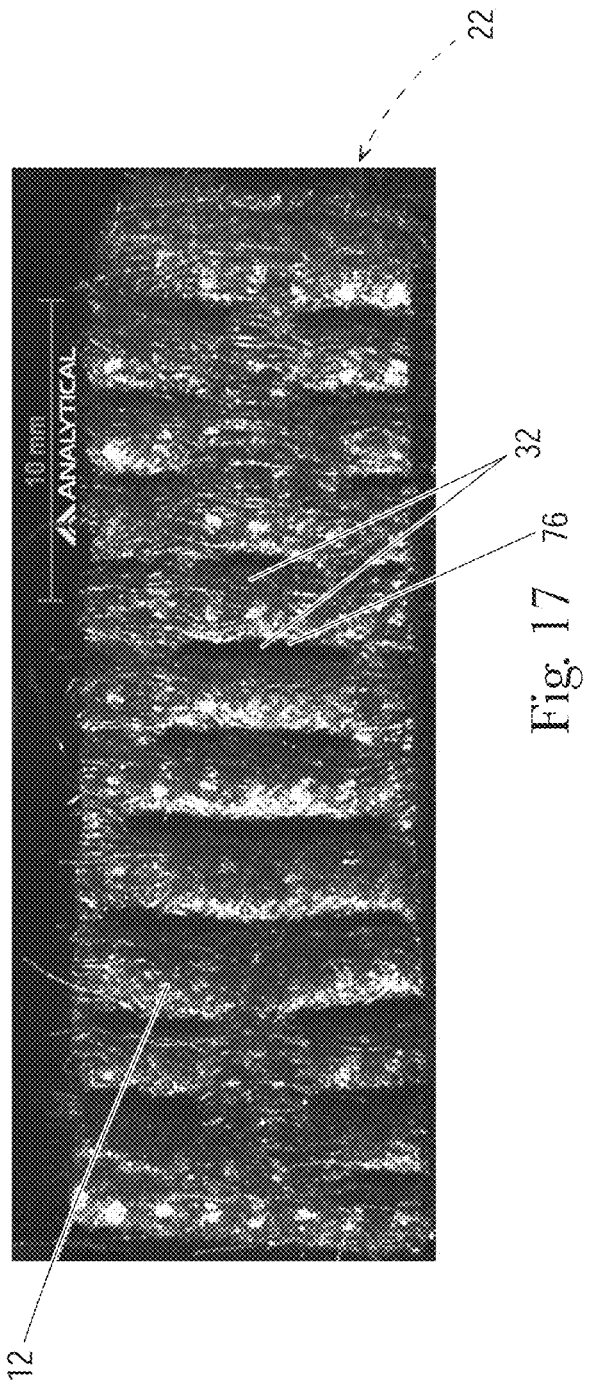
FIG. 17 shows a top view of a topsheet.
Figure 18:
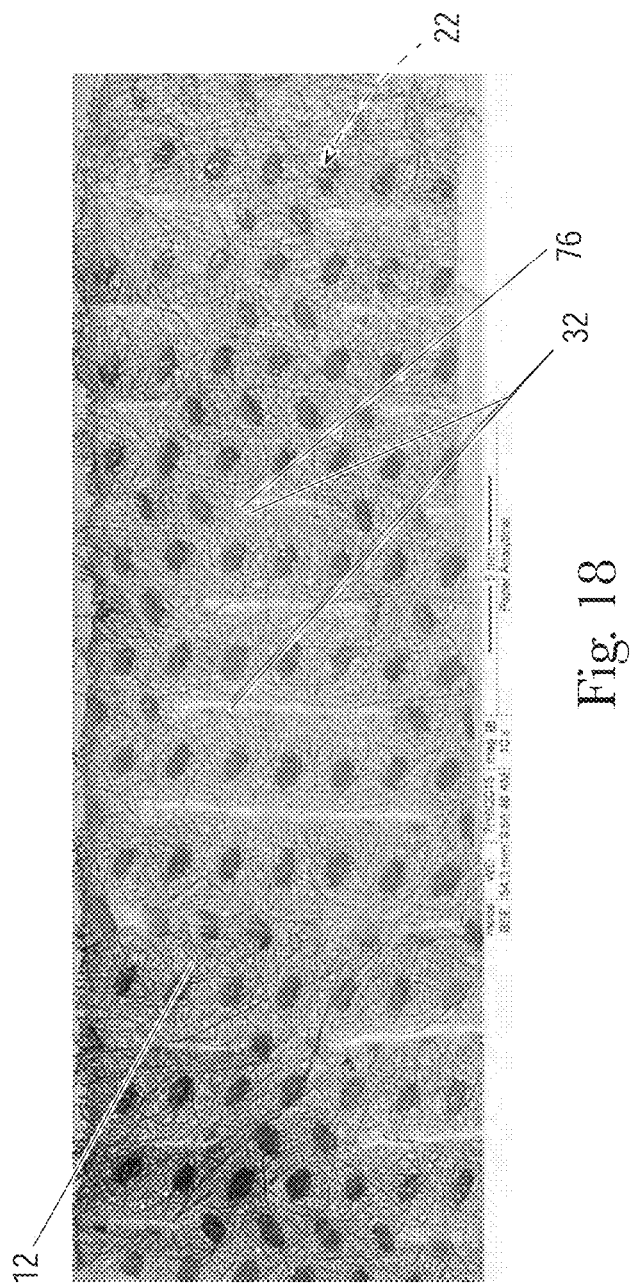
FIG. 18 shows a second top view of the topsheet of FIG. 17.

FIGS. 17 and 18 are top views of a topsheet 12 that has been integrated with a heterogeneous mass 22 stratum. A top view of one or more wells 32 or points of topsheet discontinuity 76 are indicated. FIG. 17 has been created using polarized light.

Figure 19:
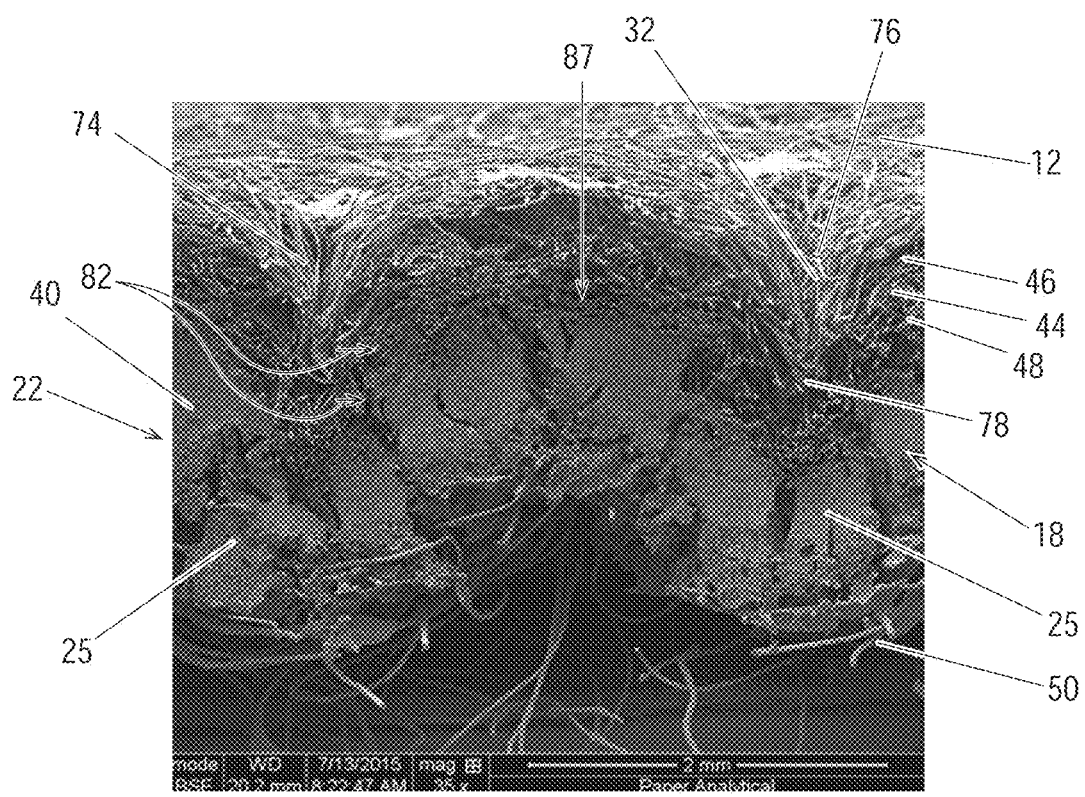
FIG. 19 shows a cross section of FIG. 18.

FIG. 19 is a cross section view of a portion of FIG. 18. FIG. 19 is an SEM micrograph of a heterogeneous mass 22 after formation means. As shown in FIG. 19, the absorbent stratum 40 is a heterogeneous mass 22 comprising a first planar nonwoven 44 having a first surface 46 and a second surface 48 and a second planar nonwoven 50. An open cell foam piece 25 enrobes a portion of the first planar nonwoven 44 and a portion of the second planar nonwoven 50. The planar nowovens are shown as wavy due to the impact of the formation means. Wells 32 or points of topsheet discontinuity 76 are shown between the open cell foam pieces 25. A group of fibers 74 is in the same X-Y plane as the heterogeneous mass 22 layer. The distal end of a well is shown as 78. As shown in FIG. 19, by integrating the topsheet with the absorbent structure, one reduces the distance in an X-Y plane (X-Y distance) 82 that fluid must travel to be absorbed into the absorbent core structure. As fluid goes deeper into the well 32, the X-Y distance 82 becomes small within each X-Y plane creating a higher capillary cascade. This is shown by the two X-Y distance arrows identified as 82. This is unlike the traditional fluid path wherein fluid travels a vertical distance or Z-distance 87 through a non-integrated portion of the topsheet before reaching the core.

Figure 20:
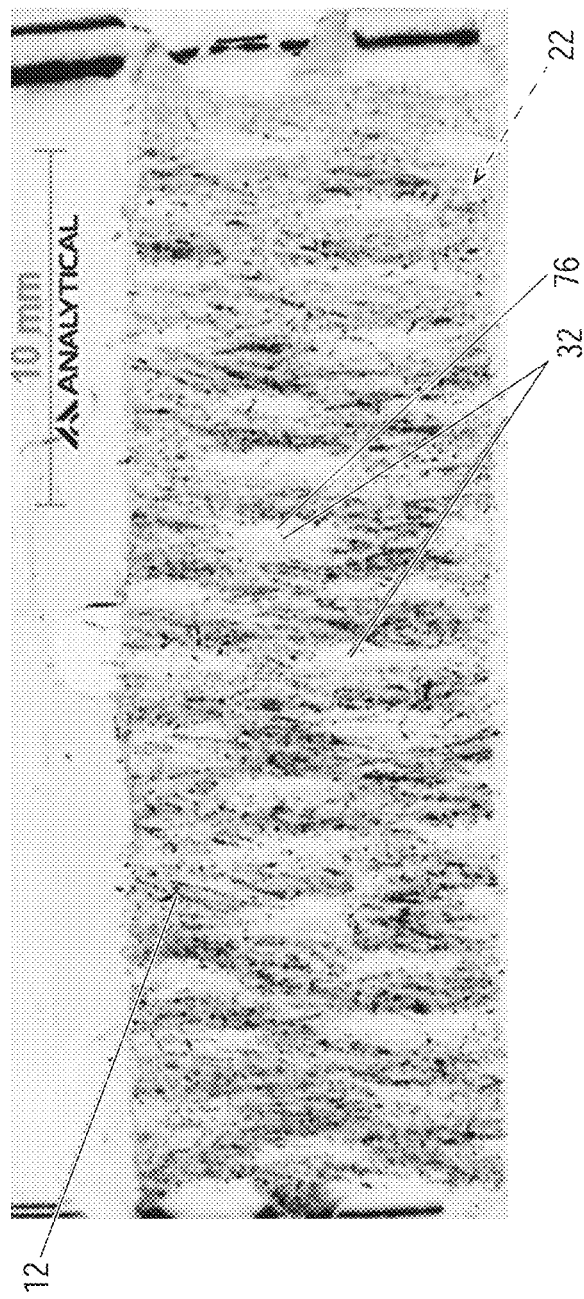
FIG. 20 shows a top view of a topsheet.
Figure 21:
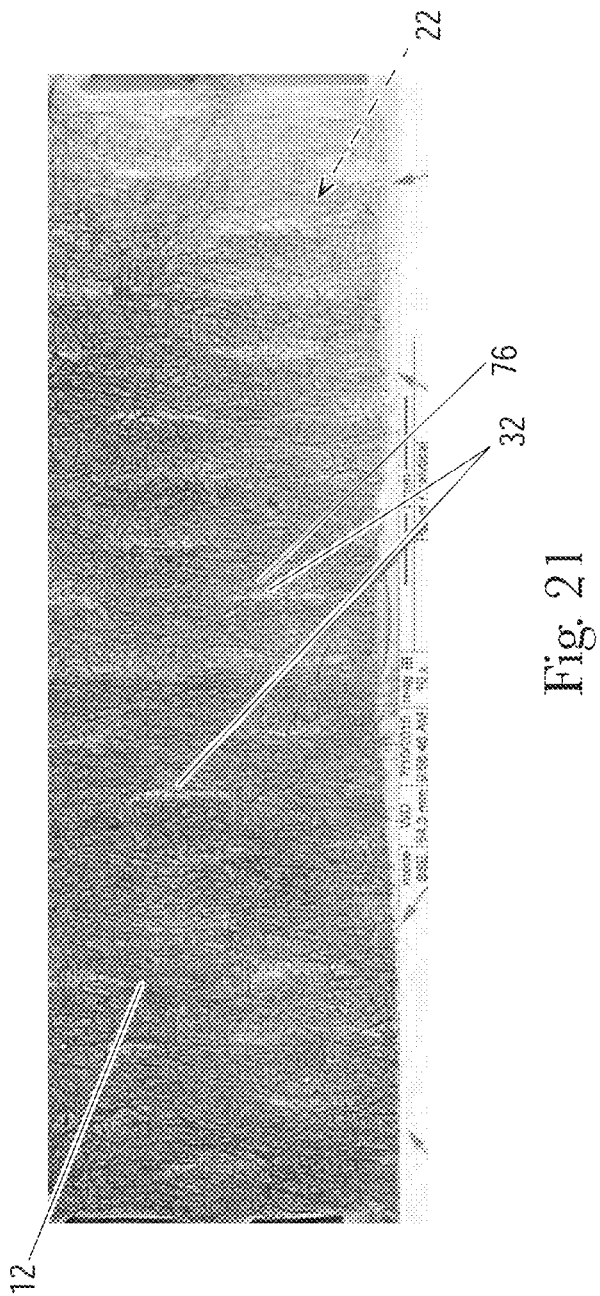
FIG. 21 shows a second top view of the topsheet of FIG. 20.

FIGS. 20 and 21 are top views of a topsheet 12 that has been integrated with a heterogeneous mass 22. A top view of one or more wells 32 or points of topsheet discontinuity 76 are indicated. FIG. 20 has been created using polarized light.

Figure 22:
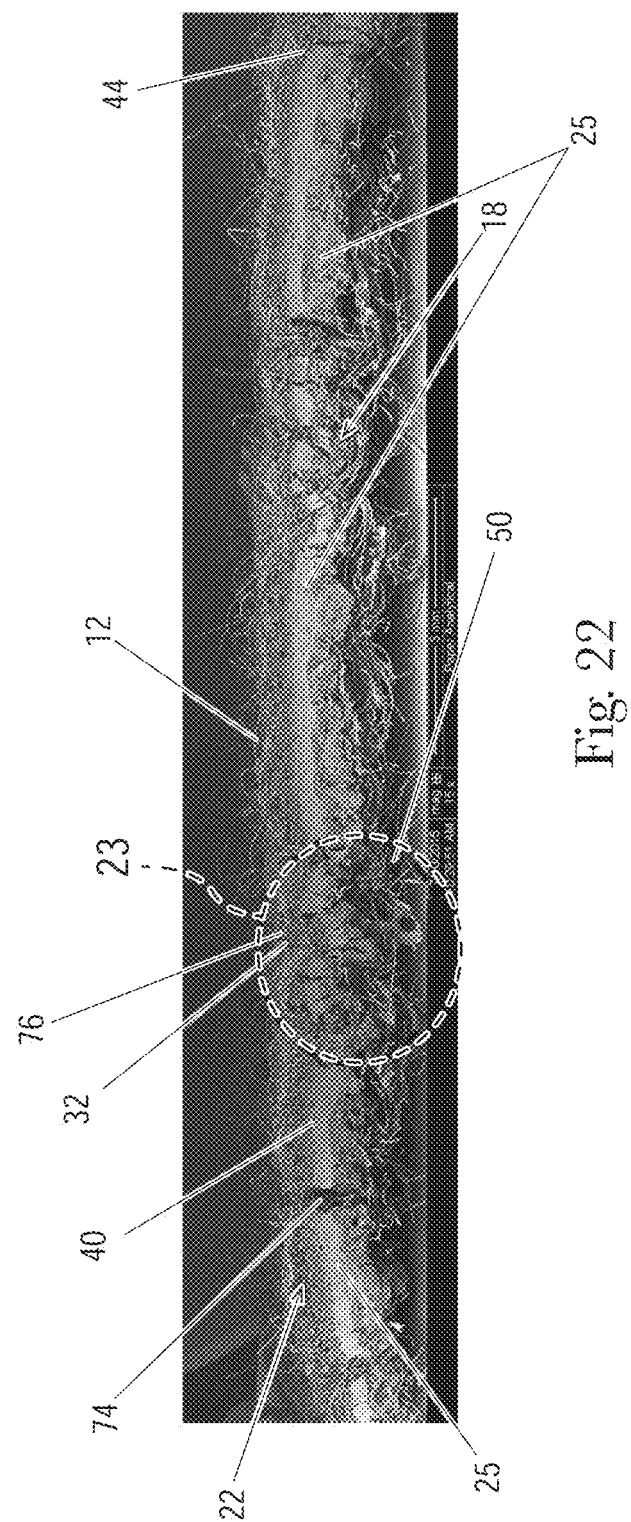
FIG. 22 shows a cross section of FIG. 21.

FIG. 22 is a cross section view of a portion of FIG. 21. FIG. 22 is an SEM micrograph of a heterogeneous mass 22 after formation means. As shown in FIG. 22, the absorbent stratum 40 is a heterogeneous mass 22 comprising a first planar nonwoven 44 and a second planar nonwoven 50. An open cell foam piece 25 enrobes a portion of the first planar nonwoven 44 and a portion of the second planar nonwoven 50. The planar nowovens are shown as wavy due to the impact of the formation means. One or more wells 32 or points of topsheet discontinuity 76 are shown between the open cell foam pieces 25. A group of fibers 74 is in the same X-Y plane as the heterogeneous mass 22 layer. The distal end of a well is shown as 78.

Figure 23:
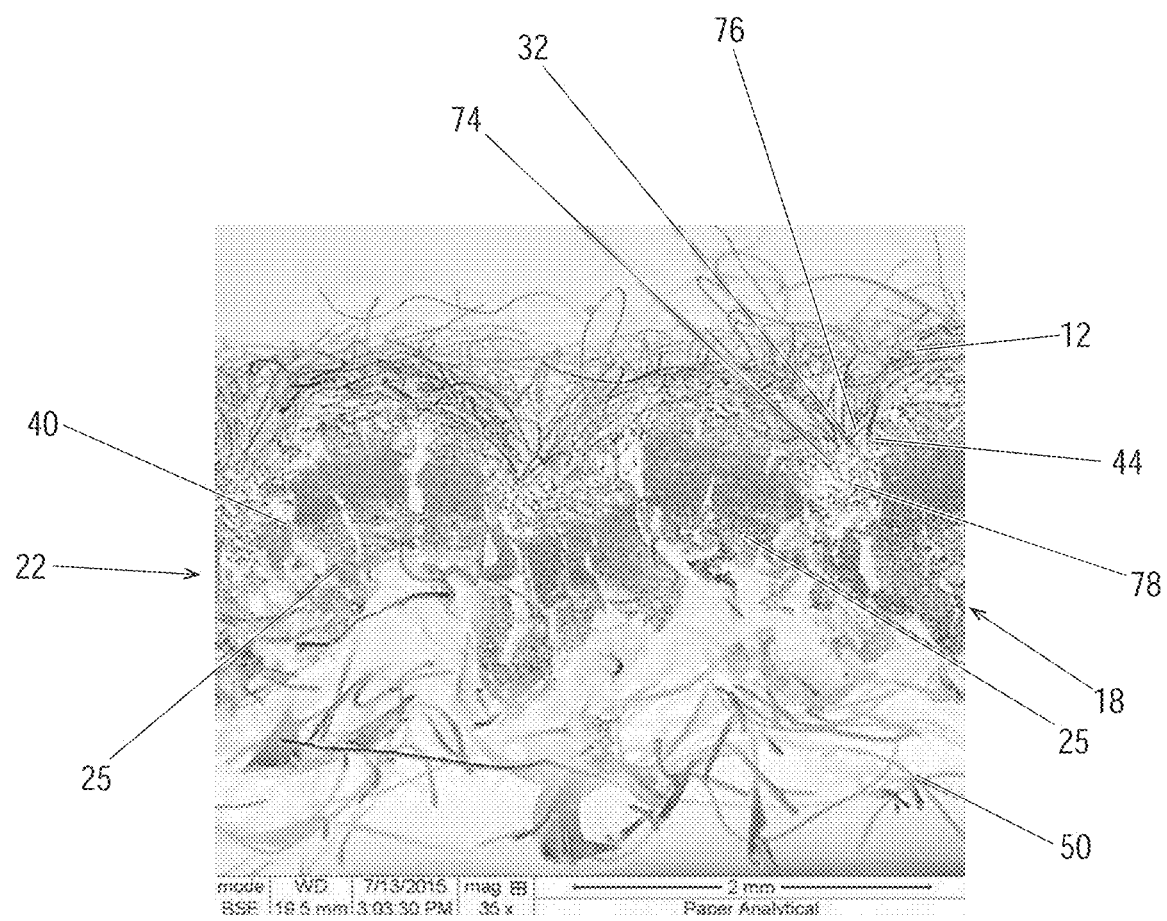
FIG. 23 zoomed in portion of the cross section of FIG. 22.

FIG. 23 is a zoomed in portion of FIG. 22. FIG. 23 is an SEM micrograph of a heterogeneous mass 22 after formation means. As shown in FIG. 23, the absorbent stratum 40 is a heterogeneous mass 22 comprising a first planar nonwoven 44 and a second planar nonwoven 50. An open cell foam piece 25 enrobes a portion of the first planar nonwoven 44 and a portion of the second planar nonwoven 50. The planar nowovens are shown as wavy due to the impact of the formation means. A well 32 or point of topsheet discontinuity 76 is shown between the open cell foam pieces 25. A group of fibers 74 is in the same X-Y plane as the heterogeneous mass 22 layer. The distal end of a well is shown as 78.

Figure 24:
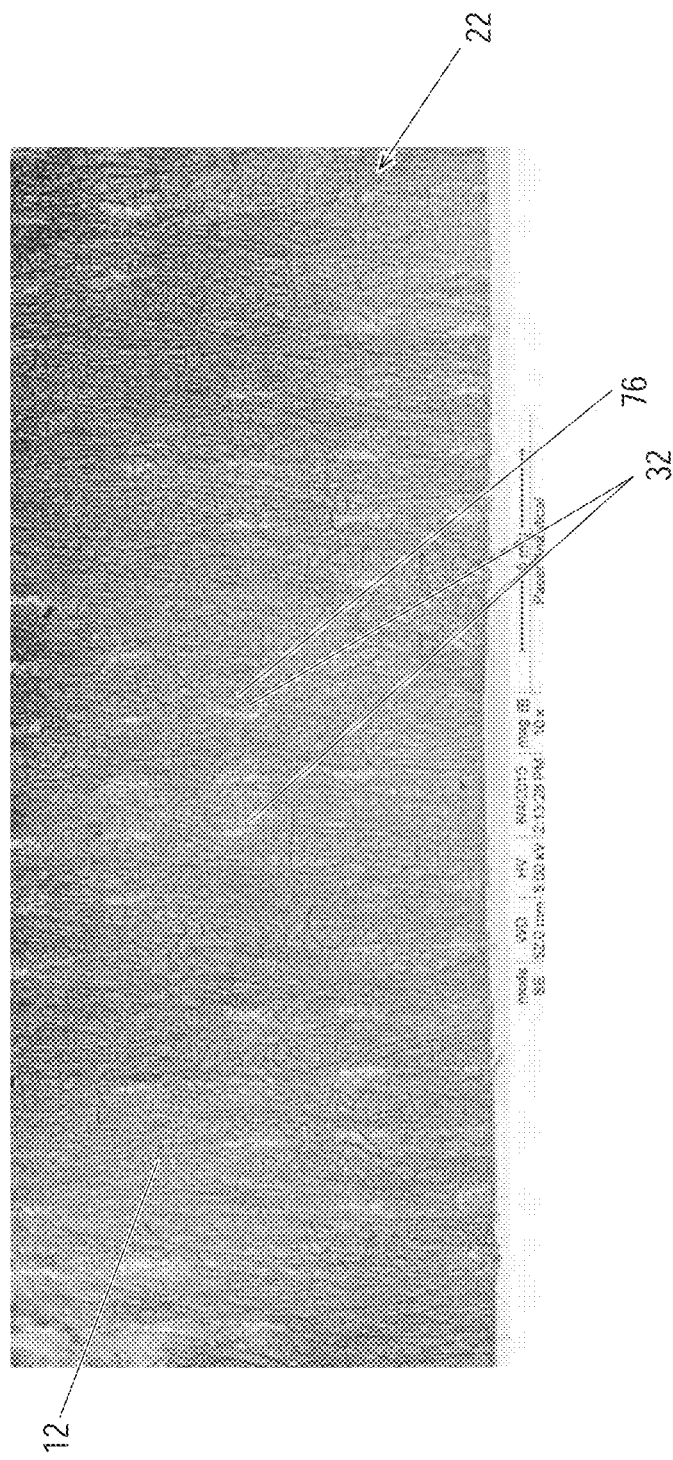
FIG. 24 shows a top view of a topsheet.

FIG. 24 is a top views of a topsheet 12 that has been integrated with a heterogeneous mass 22 stratum. One or more wells are indicated as 32.

Figure 25:
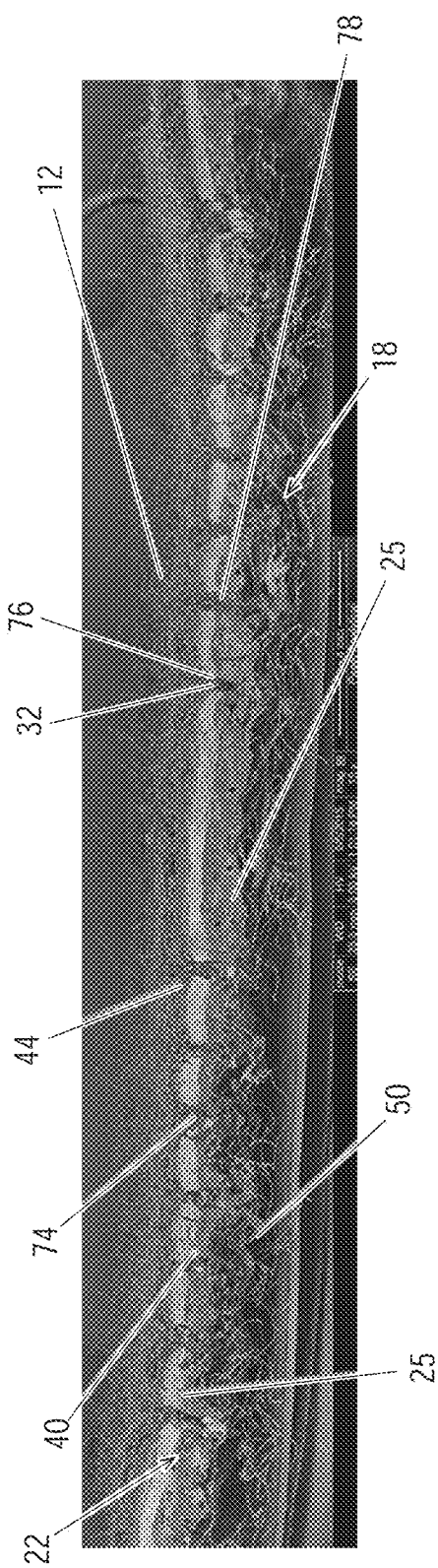
FIG. 25 shows a cross section of FIG. 24.

FIG. 25 is a cross section view of a portion of FIG. 24. FIG. 25 is an SEM micrograph of a heterogeneous mass 22 after formation means. As shown in FIG. 22, the absorbent stratum 40 is a heterogeneous mass 22 comprising a first planar nonwoven 44 and a second planar nonwoven 50. An open cell foam piece 25 enrobes a portion of the first planar nonwoven 44 and a portion of the second planar nonwoven 50. The planar nowovens are shown as wavy due to the impact of the formation means. A well 32 or point of topsheet discontinuity 76 is shown between the open cell foam pieces 25. A group of fibers 74 is in the same X-Y plane as the heterogeneous mass 22 layer. The distal end of a well is shown as 78.

Figure 26:
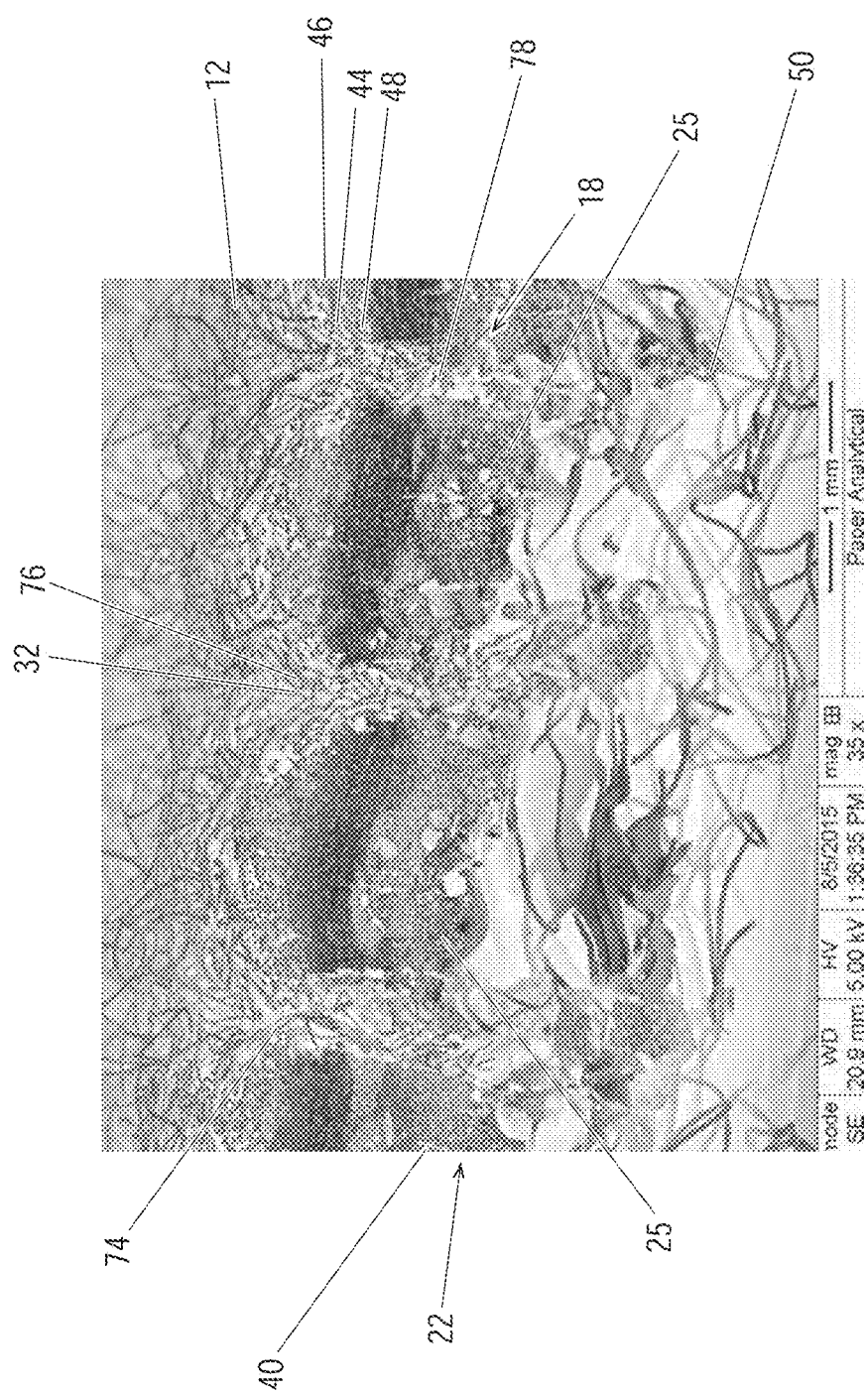
FIG. 26 zoomed in portion of the cross section of FIG. 25.

FIG. 26 is a zoomed in view of a portion of FIG. 25. FIG. 26 is an SEM micrograph of a heterogeneous mass 22 after formation means. As shown in FIG. 26, the absorbent stratum 40 is a heterogeneous mass 22 comprising a first planar nonwoven 44 having a first surface 46 and a second surface 48 and a second planar nonwoven 50. An open cell foam piece 25 enrobes a portion of the first planar nonwoven 44 and a portion of the second planar nonwoven 50. The planar nowovens are shown as wavy due to the impact of the formation means. A well 32 or point of topsheet discontinuity 76 is shown between the open cell foam pieces 25. A group of fibers 74 is in the same X-Y plane as the heterogeneous mass 22 layer. The distal end of a well is shown as 78.

FIGS. 27-29 are images of different topsheets 12 that have been integrated with a heterogeneous mass 22 stratum. FIGS. 27-29 show elongated wells 32 and non-deformed areas 33 that have not been treated with a deformation means. FIG. 29 show a first zone 80 and a second zone 81 and a first boundary 84 and a second boundary 85. FIG. 29 is a conceptual core showing a plurality of zones within the same product. The different zones are created using forming means. In this case, the core may be modified to provide optimum fluid acquisition in the middle, optimum fluid transportation in the front and back, and enhanced barrier (height, absorbency, etc.) around the perimeter of the pad. The core of FIG. 29 is not to be considered a limiting embodiment. One of ordinary skill in the art would, upon seeing the core of FIG. 29, understand that the core may comprise additional zones such as, for example, between 2 and 10 zones, such as, for example, 3 zones, 4 zones, 5 zones, 6 zones, 7 zones, 8 zones, or 9 zones.

Additionally, each one exhibits a distinct topographical surface and visual geometry. As shown in FIG. 29, more than one geometry may be located within a single absorbent article.

ZD Compression

The ZD compression of a specimen is measured on a constant rate of extension tensile tester (a suitable instrument is the MTS Alliance using Testworks 4.0 Software, as available from MTS Systems Corp., Eden Prairie, Minn.) using a load cell for which the forces measured are within 10% to 90% of the limit of the cell. The bottom stationary fixture is a circular, stainless steel platen 100 mm in diameter, and the upper movable fixture is a circular, stainless steel platen 40.00 mm in diameter. Both platens have adapters compatible with the mounts of the tensile tester, capable of securing the platens parallel to each other and orthogonal to the pull direction of the tensile tester. All testing is performed in a room controlled at 23° C.±3 C° and 50%±2% relative humidity.

Samples are conditioned at 23° C.±3 C° and 50%±2% relative humidity two hours prior to testing. Identify the longitudinal and lateral center of the product. Remove the layer of interest from the article using cryo-spray as needed. From the longitudinal and lateral midpoint, die cut a square 50.0±0.05 mm. Specimens are prepared from five replicate samples.

Before the compression test can be performed, the caliper of a specimen is measured using a calibrated digital linear caliper (e.g., Ono Sokki GS-503 or equivalent) fitted with a 24.2 mm diameter foot with an anvil that is large enough that the specimen can lie flat. The foot applies a confining pressure of 0.69 kPa to the specimen. Zero the caliper foot against the anvil. Lift the foot and insert the specimen flat against the anvil with its longitudinal and lateral midpoint centered under the foot. Lower the foot at about 5 mm/sec onto the specimen. Read the caliper (mm) 5.0 sec after resting the foot on the specimen and record to the nearest 0.01 mm.

Set the nominal gage length between the platens to approximately 3 mm greater than the specimens to be tested. Place the specimen, body facing side upward, onto the bottom platen with the longitudinal and lateral midpoint of the specimen centered under the upper platen. Zero the crosshead and load cell. Lower the crosshead at 1.00 mm/s until the distance between the bottom surface of the upper platen and the upper surface of the bottom platen is equal to the measured caliper of the specimen. This is the adjusted gage length. Start data collection at a rate of 100 Hz. Lower the crosshead at 1.00 mm/s to 50% of the adjusted gage length. Hold for 0.00 sec and then return the crosshead to the adjusted gage length. Immediately repeat this cycle for four additional cycles. Return the crosshead to the nominal gage length and remove the specimen. From the resulting Force (N) versus Displacement (mm) curves, calculate and record the Peak Force (N) for Cycle 1 and Cycle 5 to the nearest 0.01N.

In like fashion, repeat the measure for a total of 5 replicate samples. Calculate and report the arithmetic mean for the five Peak Force (N) for Cycle 1 and Peak Force (N) for Cycle 5 values separately to the nearest 0.01N.

Bunch Compression Test

Bunched Compression of a sample is measured on a constant rate of extension tensile tester (a suitable instrument is the MTS Alliance using Testworks 4.0 software, as available from MTS Systems Corp., Eden Prairie, Minn., or equivalent) using a load cell for which the forces measured are within 10% to 90% of the limit of the cell. All testing is performed in a room controlled at 23° C.±3 C° and 50%±2% relative humidity. The test can be performed wet or dry.

Figure 30:
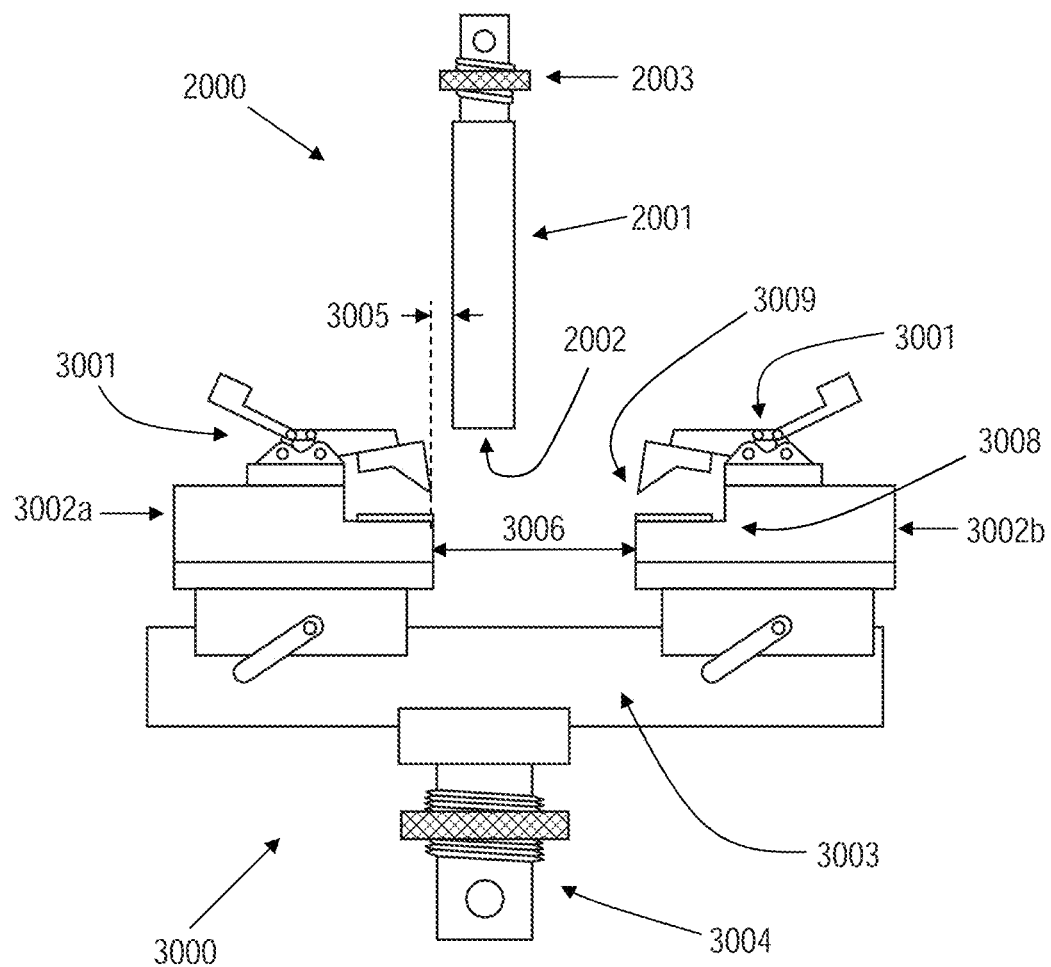
FIG. 30 shows the apparatus for a test method.

As shown in FIG. 30, The bottom stationary fixture 3000 consists of two matching sample clamps 3001 each 100 mm wide each mounted on its own movable platform 3002a, 3002b. The clamp has a "knife edge" 3009 that is 110 mm long, which clamps against a 1 mm thick hard rubber face 3008. When closed, the clamps are flush with the interior side of its respective platform. The clamps are aligned such that they hold an un-bunched specimen horizontal and orthogonal to the pull axis of the tensile tester. The platforms are mounted on a rail 3003 which allows them to be moved horizontally left to right and locked into position. The rail has an adapter 3004 compatible with the mount of the tensile tester capable of securing the platform horizontally and orthogonal to the pull axis of the tensile tester. The upper fixture 2000 is a cylindrical plunger 2001 having an overall length of 70 mm with a diameter of 25.0 mm. The contact surface 2002 is flat with no curvature. The plunger 2001 has an adapter 2003 compatible with the mount on the load cell capable of securing the plunger orthogonal to the pull axis of the tensile tester.

Samples are conditioned at 23° C.±3 C° and 50%±2% relative humidity for at least 2 hours before testing. When testing a whole article, remove the release paper from any panty fastening adhesive on the garment facing side of the article. Lightly apply talc powder to the adhesive to mitigate any tackiness. If there are cuffs, excise them with scissors, taking care not to disturb the top sheet of the product. Place the article, body facing surface up, on a bench. On the article identify the intersection of the longitudinal midline and the lateral midline. Using a rectangular cutting die, cut a specimen 100 mm in the longitudinal direction by 80 mm in the lateral direction, centered at the intersection of the midlines. When testing just the absorbent body of an article, place the absorbent body on a bench and orient as it will be integrated into an article, i.e., identify the body facing surface and the lateral and longitudinal axis. Using a rectangular cutting die, cut a specimen 100 mm in the longitudinal direction by 80 mm in the lateral direction, centered at the intersection of the midlines.

The specimen can be analyzed both wet and dry. The dry specimen requires no further preparation. The wet specimens are dosed with 7.00 mL±0.01 mL 10% w/v saline solution (100.0 g of NaCl diluted to 1 L deionized water). The dose is added using a calibrated Eppendorf-type pipettor, spreading the fluid over the complete body facing surface of the specimen within a period of approximately 3 sec. The wet specimen is tested 15.0 min±0.1 min after the dose is applied.

Program the tensile tester to zero the load cell, then lower the upper fixture at 2.00 mm/sec until the contact surface of the plunger touches the specimen and 0.02 N is read at the load cell. Zero the crosshead. Program the system to lower the crosshead 15.00 mm at 2.00 mm/sec then immediately raise the crosshead 15.00 mm at 2.00 mm/sec. This cycle is repeated for a total of five cycles, with no delay between cycles. Data is collected at 100 Hz during all compression/decompression cycles.

Figure 31A:
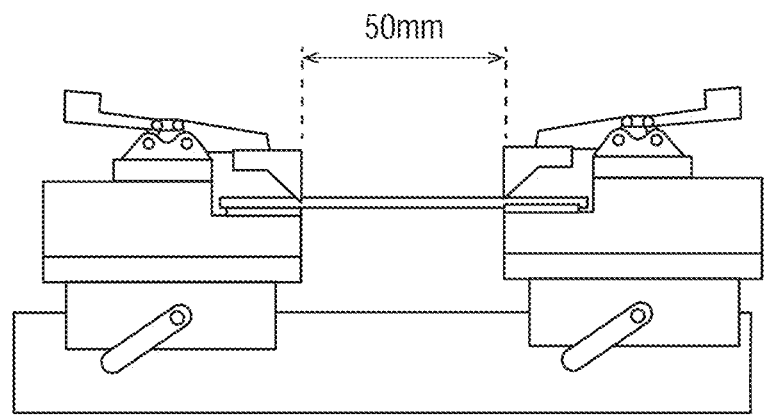
FIG. 31A-B relate to the test method of FIG. 30.
Figure 31B:
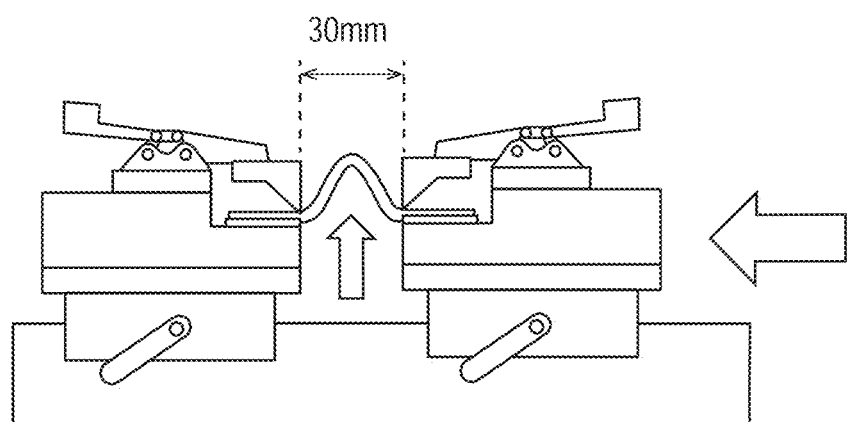

Position the left platform 3002a 2.5 mm from the side of the upper plunger (distance 3005). Lock the left platform into place. This platform 3002a will remain stationary throughout the experiment. Align the right platform 3002b 50.0 mm from the stationary clamp (distance 3006). Raise the upper probe 2001 such that it will not interfere with loading the specimen. Open both clamps. Referring to FIG. 31a, place the specimen with its longitudinal edges (i.e., the 100 mm long edges) within the clamps. With the specimen laterally centered, securely fasten both edges. Referring to FIG. 31b, move the right platform 3002b toward the stationary platform 3002a a distance 20.0 mm. Allow the specimen to bow upward as the movable platform is positioned. Manually lower the probe 2001 until the bottom surface is approximately 1 cm above the top of the bowed specimen.

Figure 32A:
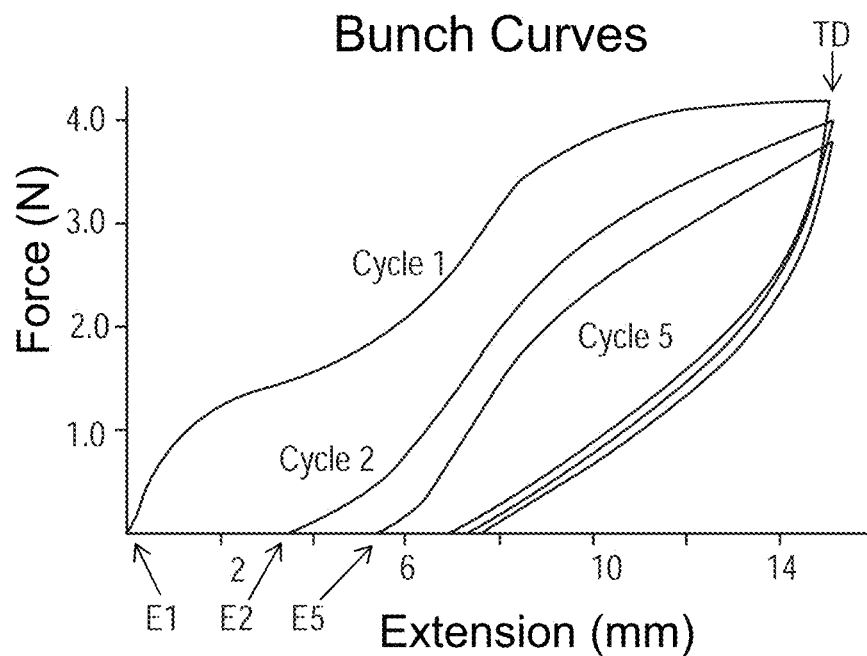
FIG. 32A-B relate to the test method of FIG. 30.
Figure 32B:
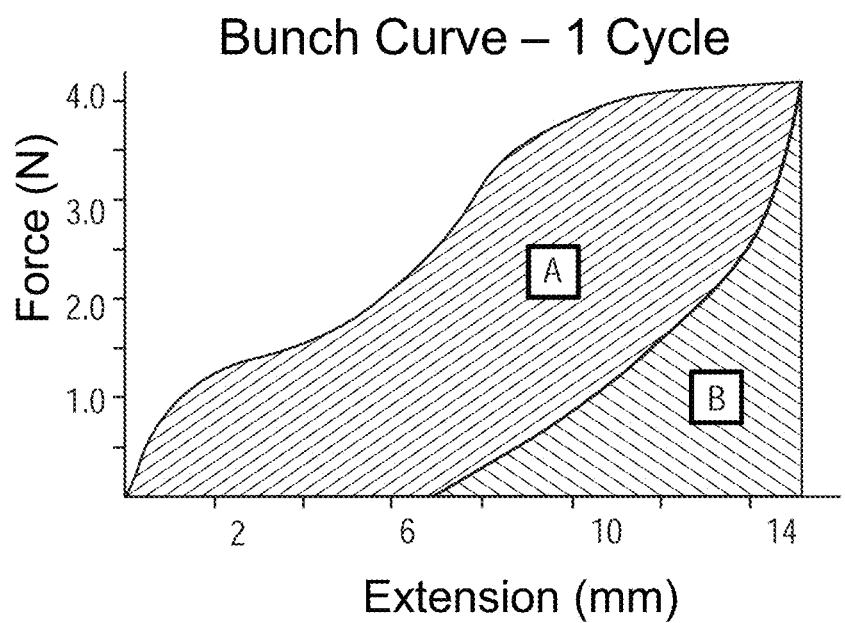

Start the test and collect displacement (mm) verses force (N) data for all five cycles. Construct a graph of Force (N) versus displacement (mm) separately for all cycles. A representative curve is shown in FIG. 32a. From the curve record the Maximum Compression Force for each Cycle to the nearest 0.01N. Calculate the % Recovery between the First and Second cycle as (TD-E2)/(TD-E1)*100 where TD is the total displacement and E2 is the extension on the second compression curve that exceeds 0.02 N. Record to the nearest 0.01%. In like fashion calculate the % Recovery between the First Cycle and other cycles as $(TD-E_i)/(TD-E1)*100$ and report to the nearest 0.01%. Referring to FIG. 32b, calculate the Energy of Compression for Cycle 1 as the area under the compression curve (i.e., area A+B) and record to the nearest 0.1 mJ. Calculate the Energy Loss from Cycle 1 as the area between the compression and decompression curves (i.e., Area A) and report to the nearest 0.1 mJ. Calculate the Energy of Recovery for Cycle 1 as the area under the decompression curve (i.e. Area B) and report to the nearest 0.1 mJ. In like fashion calculate the Energy of Compression (mJ), Energy Loss (mJ) and Energy of Recovery (mJ) for each of the other cycles and record to the nearest 0.1 mJ For each sample, analyze a total of five (5) replicates and report the arithmetic mean for each parameter. All results are reported specifically as dry or wet including test fluid (0.9% or 10%).

Kawabata Bending Rigidity

Bending rigidity is measured using a Kawabata Evaluation System KES-FB2-A, Pure Bend Tester Sensor (available from Kato Tech Co., Japan) and is reported in gfcm²/cm for both machine direction (MD) and cross direction (CD). The instrument is calibrated as per the manufacturer's instructions. All testing is performed at about 23° C.±2° C. and about 50%±2% relative humidity.

The Bending Rigidity is measured as the slope between 0.0 cm$^{-1}$ and 0.25 cm$^{-1}$ and -0.0 cm$^{-1}$ and -0.25 cm$^{-1}$. Instrument conditions are set as Maximum curvature: Kmax=±2.5 cm$^{-1}$, Cycles=1, Bending rate=2.5 cm$^{-1}$/sec.

The sensitivity is set appropriately for the sample's rigidity but a nominal value of 50 is representative.

Articles or materials are preconditioned at about 23° C.±2° C. and about 50%±2% relative humidity for 2 hours prior to testing. If the sample is an article, remove the layer of interest from the article using cryo-spray as needed. The "Standard Condition" specimen size is 20.0 cm×20.0 cm, and should be used when available. If the standard size is not available cut the width of the specimen to the nearest cm (e.g., if the width is 17.4 cm, cut to 17.0 cm) then use the "Optional Condition" setting on the instrument to specify the width to the nearest cm. If necessary based on the rigidity of the specimen, the width can be reduced to allow measurement of the specimen within the instruments capability. A total of ten (10) specimens are prepared, five for testing in each MD and CD direction.

Insert the specimen into the instrument with the body facing surface directed upward, such that the bending deformation is applied to the width direction. Start the test and record Bending Rigidity to the nearest 0.01 gfcm²/cm. Repeat testing for all specimens. Calculate Bending Rigidity as the geometric mean of the five CD specimens and of the five MD specimens and report separately to the nearest 0.01 gfcm²/cm.

Capillary Work Potential

Pore Volume Distribution measures the estimated porosity of the effective pores within an absorbent body. The approach (i) applies pre-selected, incremental, hydrostatic air pressure to a material that may absorb/desorb fluid through a fluid saturated membrane and (ii) determines the incremental and cumulative quantity of fluid that is absorbed/desorbed by the material at each pressure. A weight is positioned on the material to ensure good contact between the material and membrane and to apply an appropriate mechanical confining pressure. Pore Volume Distribution for a sample may be measured between about 5 μm and 1000 μm. From the distribution curves the Capillary Work Potential (CWP) can be calculated.

A representative instrument is a one based on the TRI/Autoporosimeter (TRI/Princeton Inc. of Princeton, N.J.), in which the operation and data treatments is described in The Journal of Colloid and Interface Science 162(1994), pp. 163-170, incorporated here by reference.

Figure 33:
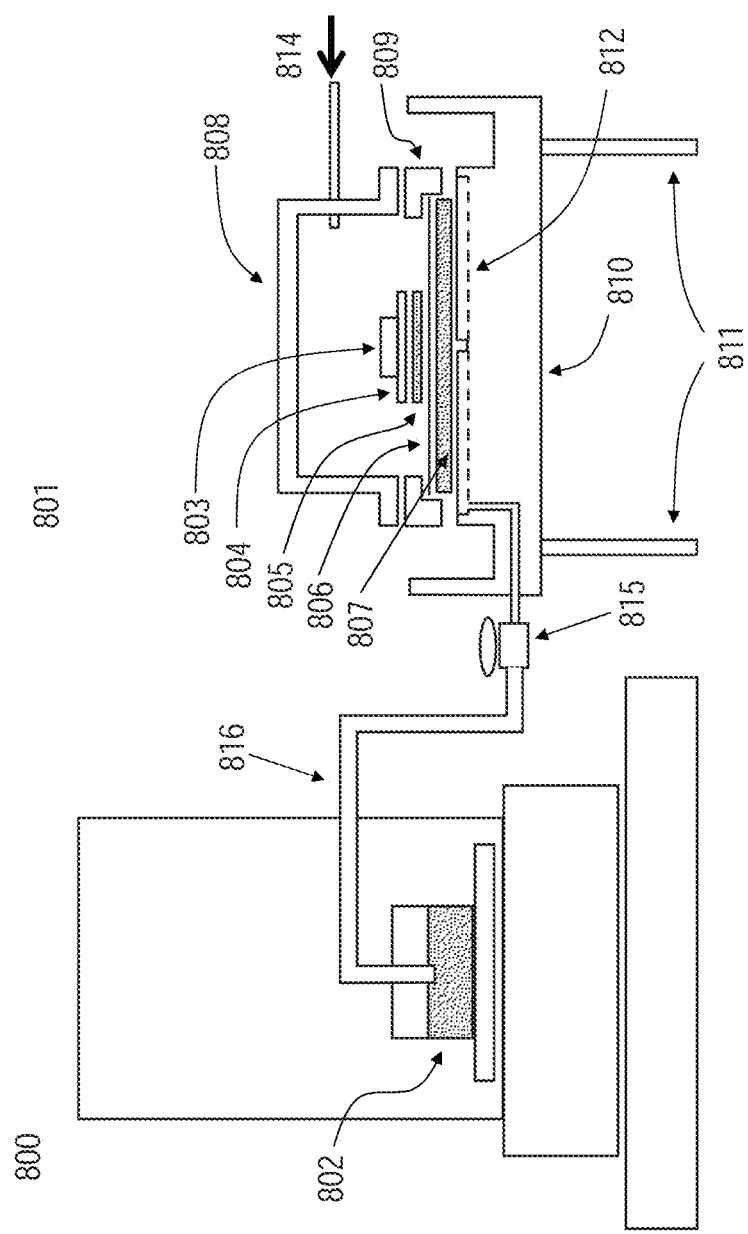
FIG. 33 shows an apparatus for a test method.
Figure 34:
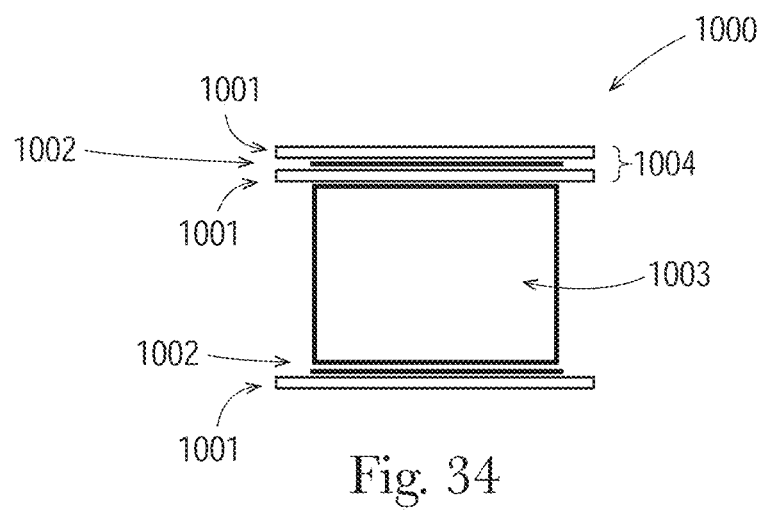
FIG. 34 shows an apparatus for a test method.
Figure 35:
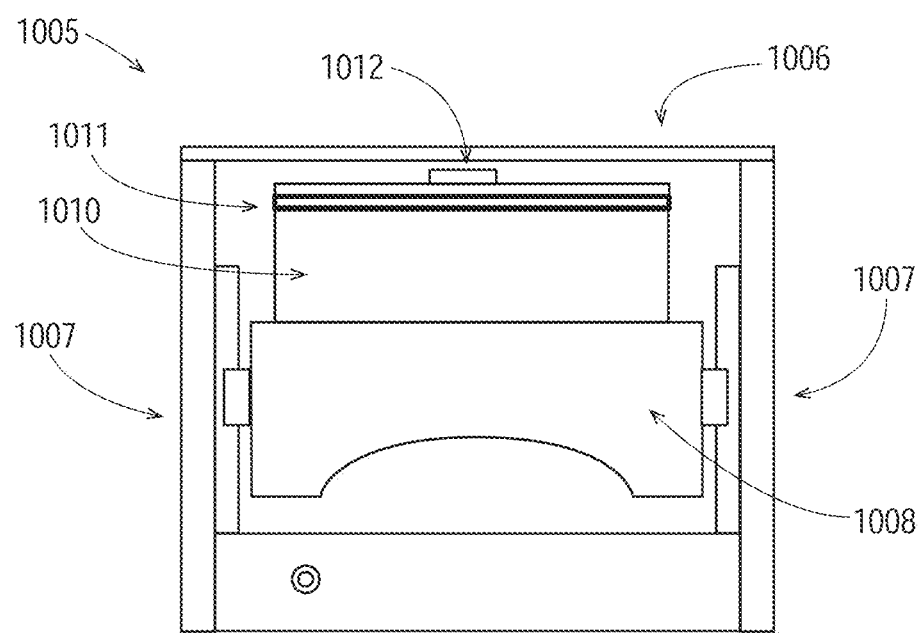
FIG. 35 shows an apparatus for a test method.

A representation of the equipment is shown in FIG. 33 and consists of a balance 800 with fluid reservoir 801 which is in direct fluid communication with the sample 811 which resides in a sealed, air-pressurized sample chamber 810.

Determining the Pore Volume Uptake or Pore-Size Distribution involves recording the increment of liquid that enters or leaves a porous material as the surrounding air pressure is altered. A sample in the test chamber is exposed to precisely controlled changes in air pressure. As the air pressure increases or decreases, the void spaces or pores of the porous media de-water or uptake fluid, respectively. Total fluid uptake is determined as the total volume of fluid absorbed by the porous media.

Pore-Size Distribution can further be determined as the distribution of the volume of uptake of each pore-size group, as measured by the instrument at the corresponding pressure. The pore size is taken as the effective radius of a pore and is related to the pressure differential by the following relationship:

$$\text{Pressure differential} = [2\gamma \cos \Theta)]/\text{effective radius}$$

where γ=liquid surface tension, and Θ=contact angle

For this experiment: γ=27 dyne/cm² divided by the acceleration of gravity; cos Θ=1° The automated equipment operates by precisely changing the test chamber air pressure in user-specified increments, either by decreasing pressure (increasing pore size) to cause fluid uptake by the porous media, or by increasing pressure (decreasing pore size) to drain the porous media. The liquid volume absorbed (drained) at each pressure increment yields the pore size distribution. The fluid uptake is the cumulative volume for all pores taken up by the porous media, as it progresses to saturation (e.g. all pores filled).

Experimental Conditions

Take a 9 cm diameter, 0.22 µm membrane filter (mixed cellulose esters, Millipore GSWP, EMD Millipore Corp., Billerica Mass.) by adhering the filter to a 9 cm diameter by 0.6 cm thick Monel porous frit 807 (available from Mott Corp, CT) using KRYLON® spray paint (FilmTools Gloss White Spray Paint #1501). Allow the frit/membrane to dry before use.

Fill the inner base 812 of the sample chamber with hexadecane (available from Sigma-Aldrich CAS #544-76-3). Place the frit 807 membrane side up onto the base of the sample chamber 810, and secure it into place with a locking collar 809. Fill the connecting tube 816, reservoir 802, and the frit 807 with hexadecane assuring that no bubbles are trapped within the connecting tube or the pores within the frit and membrane. Using the legs of the base 811, level the sample camber and align the membrane with the top surface of the fluid within the reservoir.

Dye cut a specimen 5.5 cm square. Measure the mass of the specimen to the nearest 0.1 mg. A 5.5 cm square, Plexiglas cover plate 804 and confining weight 803 are selected to provide a confining pressure of 0.25 psi.

Place the top of the sample chamber 808 in place and seal the chamber. Apply the appropriate air pressure to the cell (connection 814) to achieve a 5 µm effective pore radius. Close the liquid valve 815. Open the sample chamber, place the specimen 805, cover plate 804 and confining weight 803 into the chamber onto the membrane 806 and seal the camber. Open the liquid valve 815 to allow free movement of liquid to the balance.

Progress the system through a sequence of pore sizes (pressures) as follows (effective pore radius in µm): 5, 10, 20, 30, 40, 50, 60, 70, 80, 90, 100, 120, 140, 160, 180, 200, 250, 300, 350, 400, 450, 500, 500, 550, 600, 700, 800, 1000, 800, 700, 600, 550, 500, 450, 400, 350, 300, 250, 200, 180, 160, 140, 120, 100, 90, 80, 70, 60, 50, 40, 30, 20, 10, 5, 10, 20, 30, 40, 50, 60, 70, 80, 90, 100, 120, 140, 160, 180, 200, 250, 300, 350, 400, 450, 500, 500, 550, 600, 700, 800, 1000. The sequence is progressed to the next radius when an equilibrium rate of less than 25 mg/min is measured at the balance.

In like fashion, measure the acquisition/drainage/acquisition cycle blank without a sample. Based on the incremental volume values, calculate the blank-corrected values for cumulative volume.

Cumulative Volume (mm³/mg)=[Specimen Fluid Uptake (mg)−Blank Fluid Uptake (mg)]/Density of Hexadecane (g/cm³)/Sample Mass (mg)

The Capillary Work Potential (CWP) is the work done by the sample normalized by the area of the specimen. The trapezoidal rule is used to integrate the ith pressure as a function of cumulative volume over n data points:

$$CWP\left[\frac{mJ}{m^2}\right] = \frac{W}{A_w} = \sum_{i=1}^{n} \frac{1}{2} \frac{m_w(CV_{i+1} - CV_i)(P_i + P_{i+1})}{A_w} \left(10^3 \left[\frac{mJ}{J}\right]\right)$$

where
$m_w$=mass of web (mg)
CV=Cumulative Volume (m³/mg)
P=Air Pressure (Pa)
$A_w$=Area (m²)

Record the CWP to the nearest 0.1 mJ/m². In like fashion, repeat the measure on a total of three (3) replicate specimens. Calculate the arithmetic mean of the replicates and report to the nearest 0.1 mJ/m².

Kinetics and 1D Liquid Distribution by NMR-MOUSE

The NMR-MOUSE (Mobile Universal Surface Explorer) is a portable open NMR sensor equipped with a permanent magnet geometry that generates a highly uniform gradient perpendicular to the scanner surface. A frame 1007 with horizontal plane 1006 supports the specimen and remains stationary during the test. A flat sensitive volume of the specimen is excited and detected by a surface rf coil 1012 placed on top of the magnet 1010 at a position that defines the maximum penetration depth into the specimen. By repositioning the sensitive slice across the specimen by means of a high precision lift 1008, the scanner can produce one-dimensional profiles of the specimen's structure with high spatial resolution.

An exemplary instrument is the Profile NMR-MOUSE model PM25 with High-Precision Lift available from Magritek Inc., San Diego, Calif. Requirements for the NMR-MOUSE are a 100 µm resolution in the z-direction, a measuring frequency of 13.5 MHz, a maximum measuring depth of 25 mm, a static gradient of 8 T/m, and a sensitive volume (x-y dimension) of 40 by 40 mm². Before the instrument can be used, perform phasing adjustment, check resonance frequency and check external noise level as per the manufacturer's instruction. A syringe pump capable of delivering test fluid in the range of 1 mL/min to 5 mL/min±0.01 mL/min is used to dose the specimen. All measurements are conducted in a room controlled at 23° C.±0.5° C. and 50%±2% relative humidity.

The test solution is Paper Industry Fluid (PIF) prepared as 15 g carboxymethylcellulose, 10 g NaCl, 4 g $NaHCO_3$, 80 g glycerol (all available from SigmaAldrich) in 1000 g distilled water. 2 mM/L of Diethylenetriaminepentaacetic acid gadolinium (III) dihydrogen salt (available from SigmaAldrich) is added to each. After addition the solutions are stirred using an shaker at 160 rpm for one hour. Afterwards the solutions are checked to assure no visible undissolved crystals remain. The solution is prepared 10 hours prior to use.

Products for testing are conditioned at 23° C.±0.5° C. and 50%±2% relative humidity for two hours prior to testing. Identify the intersection of the lateral and longitudinal center line of the product. Cut a 40.0 mm by 40.0 mm specimen from the product, centered at that intersection, with the cut edges parallel and perpendicular to the longitudinal axis of the product. The garment facing side of the specimen 1003 is mounted on a 50 mm×50 mm×0.30 mm glass slide 1001 using a 40.0 mm by 40.0 mm piece of double-sided tape 1002 (tape must be suitable to provide NMR Amplitude signal). A top cap 1004 is prepared by adhering two 50 mm×50 mm×0.30 mm glass slides 1001 together using a 40 mm by 40 mm piece of two-sided tape 1002. The cap is then placed on top of the specimen. The two tape layers are used as functional markers to define the dimension of the specimen by the instrument.

Figure 36A:
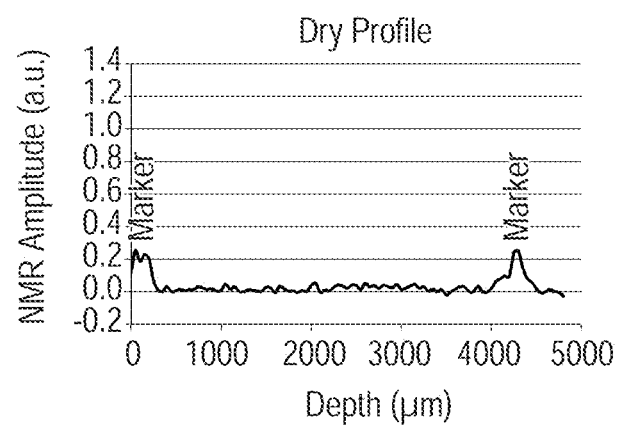
FIG. 36a shows a plot of an NMR profile.

First a 1-D Dry Distribution Profile of the specimen is collected. Place the prepared specimen onto the instrument aligned over top the coils. Program the NMR-MOUSE for a Carr-Purcell-Meiboom-Gill (CPMG) pulse sequence consisting of a 90° x-pulse follow by a refocusing pulse of 180° y-pulse using the following conditions:

Repetition Time=500 ms
Number of Scans=8
Number of Echoes=8
Resolution=100 µm
Step Size=–100 µm Collect NMR Amplitude data (in arbitrary units, a.u.) versus depth (µm) as the high precision lift steps through the specimen's depth. A representative graph is shown in FIG. 36a.

The second measure is the Kinetic Experiment of the test fluid moving though the sensitive NMR volume as test fluid is slowly added to the top of the specimen. The "trickle" dose is followed by a "gush" dose added using a calibrated dispenser pipet. Program the NMR-MOUSE for a CPMG pulse sequence using the following conditions:

Measurement Depth=5 mm
Repetition Time=200 ms
90° Amplitude=–7 dB
180° Amplitude=0 dB
Pulse Length=5 µs Echo Time=90 µs
Number of Echoes=128
Echo Shift=1 µs
Experiments before trigger=50
Experiments after trigger=2000
Rx Gain=31 dB
Acquisition Time=8 µs
Number of Scans=1

Rx Phase is determined during the phase adjustment as described by the vendor. A value of 230° was typical for our experiments. Pulse length depends on measurement depth which here is 5 mm. If necessary the depth can be adjusted using the spacer 1011.

Figure 37:
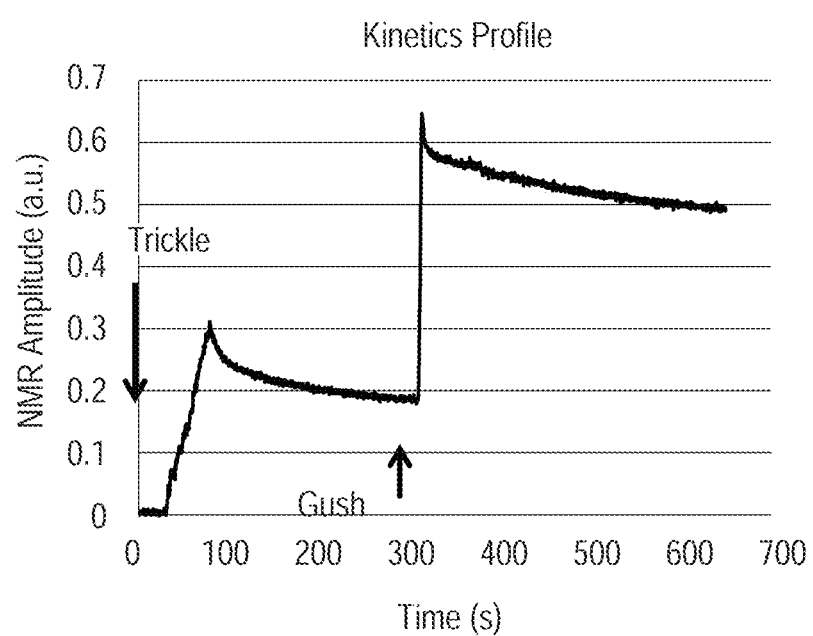
FIG. 37 shows a kinetic plot of an NMR profile.

Using the precision lift adjust the height of the specimen so that the desired target region is aligned with the instruments sensitive volume. Target regions can be chosen based on SEM cross sections. Program the syringe pump to deliver 1.00 mL/min±0.01 mL for 1.00 min for PIF test fluid or 5.00 mL/min±0.01 mL for 1.00 min for 0.9% Saline test fluid. Start the measurement and collect NMR Amplitude (a.u.) for 50 experiments before initiating fluid flow to provide a signal baseline. Position the outlet tube from the syringe pump over the center of the specimen and move during applying liquid over the total sample surface, but do not touch the borders of the sample. Trigger the system to continue collection of NMR amplitude data while simultaneously initiating fluid flow for 1 mL over 60 sec. At 300 sec after the trigger, add 0.50 mL of test fluid at approximately 0.5 mL/sec to the center of the specimen via a calibrated Eppendorf pipet. A representative example of the NMR Amplitude versus time graph is shown in FIG. 37.

Figure 36B:
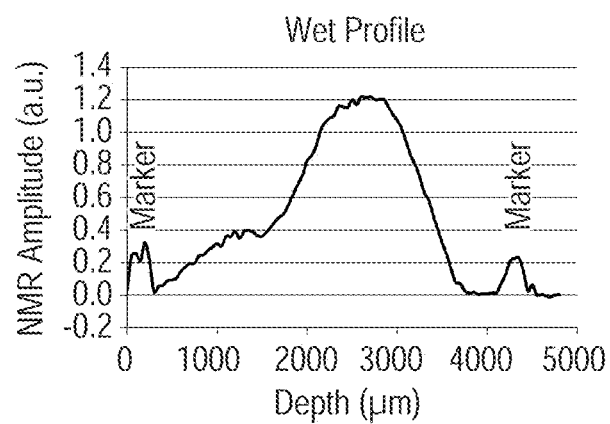
FIG. 36b shows a plot of an NMR profile.

The third measurement is a 1-D Wet Distribution Profile Immediately after the Kinetic measurement is complete, replace the cap on the specimen. The Wet Distribution is run under the same experimental conditions as the previous Dry Distribution, described above. A representative graph is shown in FIG. 36b.

Calibration of the NMR Amplitude for the Kinetic signal can be performed by filling glass vials (8 mm outer diameter and a defined inner diameter by at least 50 mm tall) with the appropriate fluid. Set the instrument conditions as described for the kinetics experiment. A calibration curve is constructed by placing an increasing number of vials onto the instrument (vials should be distributed equally over the 40 mm×40 mm measurement region) and perform the kinetic measurements. The volumes are calculated as the summed cross sectional area of the vials present multiplied by the z-resolution where Resolution (mm) is calculated as 1/Acquisition Time (s) divided by the instruments Gradient Strength (Hz/mm). The Calibration of the NMR Amplitude for the Distribution Profile is performed as an internal calibration based on the dry and wet profiles. In this procedure the area beneath wet and dry profile were calculated and after subtracting them the total area (excluding markers) was obtained. This total area is correlated to the amount of applied liquid (here 1.5 mL). The liquid amount (µL) per 100 µm step can then be calculated.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Values disclosed herein as ends of ranges are not to be understood as being strictly limited to the exact numerical values recited. Instead, unless otherwise specified, each numerical range is intended to mean both the recited values and any integers within the range. For example, a range disclosed as "1 to 10" is intended to mean "1, 2, 3, 4, 5, 6, 7, 8, 9, and 10."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent feminine hygiene pad comprising a topsheet, a secondary topsheet, a backsheet, and an absorbent core structure comprising one or more layers wherein at least one layer is a heterogeneous mass layer comprising a body of open celled HIPE foam formed about and enrobing fibers of a nonwoven web, wherein a portion of the topsheet, a portion of the secondary topsheet, and the heterogeneous mass layer are integrated such that they all reside in the same X-Y plane.

2. The feminine hygiene pad of claim 1, wherein the integrated portion of the topsheet and heterogeneous mass layer comprise one or more wells.

3. The feminine hygiene pad of claim 1, wherein a grouping of fibers of the topsheet is physically inserted into the heterogeneous mass layer.

4. The feminine hygiene pad of claim 3, wherein at least a portion of the grouping of fibers forms a portion of a well outer surface.

5. The feminine hygiene pad of claim 1, wherein the absorbent article exhibits a capillarity cascade in an X-Y plane.

6. The feminine hygiene pad of claim 1, wherein the absorbent core structure comprises a lower layer wherein the lower layer comprises a substrate comprising superabsorbent materials.

7. The feminine hygiene pad of claim 1, wherein the topsheet comprises more than one layer.

* * * * *